US010350290B2

(12) United States Patent
Ott et al.

(10) Patent No.: US 10,350,290 B2
(45) Date of Patent: *Jul. 16, 2019

(54) LINEAR CHIMERIC COMPOUNDS AND METHODS OF USE THEREOF

(71) Applicant: Dynavax Technologies Corporation, Berkeley, CA (US)

(72) Inventors: Gary S. Ott, Oakland, CA (US); Robert J. Milley, Oakland, CA (US); Robert L. Coffman, Portola Valley, CA (US); Radwan Kiwan, Albany, CA (US); Holger Kanzler, Gaithersburg, MD (US)

(73) Assignee: DYNAVAX TECHNOLOGIES CORPORATION, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/958,292

(22) Filed: Apr. 20, 2018

(65) Prior Publication Data

US 2018/0360954 A1 Dec. 20, 2018

Related U.S. Application Data

(63) Continuation of application No. 15/004,860, filed on Jan. 22, 2016, now Pat. No. 9,950,064.

(60) Provisional application No. 62/107,291, filed on Jan. 23, 2015.

(51) Int. Cl.

| | |
|---|---|
| *C12N 15/117* | (2010.01) |
| *C07H 21/00* | (2006.01) |
| *C07H 21/02* | (2006.01) |
| *C07H 21/04* | (2006.01) |
| *A61K 45/06* | (2006.01) |
| *A61K 39/39* | (2006.01) |
| *A61K 31/7125* | (2006.01) |
| *A61K 39/07* | (2006.01) |
| *A61K 39/12* | (2006.01) |
| *A61K 47/60* | (2017.01) |
| *A61K 47/61* | (2017.01) |
| *A61K 39/00* | (2006.01) |

(52) U.S. Cl.
CPC .......... *A61K 39/39* (2013.01); *A61K 31/7125* (2013.01); *A61K 39/07* (2013.01); *A61K 39/12* (2013.01); *A61K 47/60* (2017.08); *A61K 47/61* (2017.08); *C07H 21/00* (2013.01); *C07H 21/04* (2013.01); *A61K 2039/545* (2013.01); *A61K 2039/55511* (2013.01); *A61K 2039/55561* (2013.01); *A61K 2039/572* (2013.01); *A61K 2039/575* (2013.01); *C12N 2730/10134* (2013.01)

(58) Field of Classification Search
None
See application file for complete search history.

(56) References Cited

U.S. PATENT DOCUMENTS

| | | | |
|---|---|---|---|
| 7,255,868 B2 | 8/2007 | Fearon et al. | |
| 7,785,610 B2 | 8/2010 | Fearon et al. | |
| 8,003,115 B2 | 8/2011 | Fearon et al. | |
| 8,114,418 B2 | 2/2012 | Fearon et al. | |
| 8,222,398 B2 | 7/2012 | Fearon et al. | |
| 8,597,665 B2 | 12/2013 | Fearon et al. | |
| 9,028,845 B2 | 5/2015 | Fearon et al. | |
| 9,950,064 B2 | 4/2018 | Ott et al. | |

FOREIGN PATENT DOCUMENTS

| | | |
|---|---|---|
| WO | WO-2003/000922 A2 | 1/2003 |
| WO | WO-2016/118932 A1 | 7/2016 |

OTHER PUBLICATIONS

Cheever et al. (2009). "The prioritization of cancer antigens: a national cancer institute pilot project for the acceleration of translational research," *Clin Cancer Res*, 15:5323-5337.
Gosu et al. (2012). "Therapeutic applications of nucleic acids and their analogues in Toll-like receptor signaling," *Molecules*, 17:13503-13529.
Guiducci et al. (2006). "Properties Regulating the Nature of the Plasmacytoid Dendritic Cell Response to Toll-like Receptor 9 Activation," *J Exp Med*, 203(8):1999-2008.
Hickle et al. (2014). "A Toll-like receptor 9 ligand nanoparticle formulation for prophylactic vaccination against *Bacillus anthracis* (anthrax) enhances in vivo uptake of TLR9-ligand and induction of maturation markers on antigen-presenting cell populations in mice," abstract of poster presentation made at *The 53rd Midwinter Conference of Immunologists*, Pacific Grove, CA, 1 page.
Hickle et al. (2014). "A Toll-like receptor 9 ligand nanoparticle formulation for prophylactic vaccination against *Bacillus anthracis* (anthrax) enhances in vivo uptake of TLR9-ligand and induction of maturation markers on antigen-presenting cell populations in mice," poster presentation made at *The 53rd Midwinter Conference of Immunologists*, Pacific Grove, CA, 1 page.
Inman. (1975). "Thymus-independent antigens: the preparation of covalent, hapten-ficoll conjugates," *J Immunol*, 114:704-709.
Kachura et al. (2014) "A Toll-like receptor 9 ligand nanoparticle formulation for prophylactic vaccination against *Bacillus anthracis* (anthrax) enhances in vivo induction of interferon and chemoattractant-associated genes," abstract of poster presentation made at *The 53rd Midwinter Conference of Immunologists*, Pacific Grove, CA, 1 page.
Kachura et al. (2014) "A Toll-like receptor 9 ligand nanoparticle formulation for prophylactic vaccination against Bacillus anthracis (anthrax) enhances in vivo induction of interferon and chemoattractant-associated genes," poster presentation made at The 53rd Midwinter Conference of Immunologists, Pacific Grove, CA, 1 page.

(Continued)

*Primary Examiner* — Jennifer Pitrak McDonald
(74) *Attorney, Agent, or Firm* — Morrison & Foerster LLP

(57) ABSTRACT

The present disclosure relates to branched and linear chimeric compounds containing both nucleic acid and non-nucleic acid moieties, as well as to polynucleotides. The present disclosure also relates to uses thereof for stimulating an immune response, and to methods for preparation of the branched chimeric compounds.

18 Claims, 22 Drawing Sheets

Specification includes a Sequence Listing.

(56) References Cited

OTHER PUBLICATIONS

Kachura et al. (2016, e-pub. Nov. 25, 2015) "A CpG-Ficoll Nanoparticle Adjuvant for Anthrax Protective Antigen Enhances Immunogenicity and Provides Single-Immunization Protection Against Inhaled Anthrax in Monkeys" *J Immunol*, 196:284-297.

Kanzler et al. (2012) "A polyvalent Toll-like receptor nanoparticle ligand as adjuvant for a prophylactic vaccine against *Bacillus anthracis* (anthrax)," poster presentation made at the *Keystone Symposia Global Health Series: Immunological Mechanisms of Vaccination*, Ottawa, Ontario, Canada, 1 page.

Kell et al. (2014) "Toll-like receptor 9 ligand-ficoll nanoparticles are more potent than free TLR9 ligands in inducing lymph node germinal center B and T cell responses following immunization with anthrax protective antigen in mice," abstract of poster presentation made at *The 53rd Midwinter Conference of Immunologists*, Pacific Grove, CA, 1 page.

Kell et al. (2014) "Toll-like receptor 9 ligand-ficoll nanoparticles are more potent than free TLR9 ligands in inducing lymph node germinal center B and T cell responses following immunization with anthrax protective antigen in mice," poster presentation made at *The 53rd Midwinter Conference of Immunologists*, Pacific Grove, CA, 1 page.

Lee et al. (1980). "A method for preparing beta-hCG COOH peptide-carrier conjugates of predictable composition," *Mol Immunol*, 17:749-56.

Marshall et al. (2003). "Novel chimeric immunomodulatory compounds containing short CpG oligodeoxyribonucleotides have differential activities in human cells," *Nucleic Acids Res*, 31:5122-5133.

Milley et al. (2016, e-pub. Apr. 13, 2016) "Optimization, Production and Characterization of a CpG-Oligonucleotide-Ficoll Conjugate Nanoparticle Adjuvant for Enhanced Immunogenicity of Anthrax Protective Antigen" *Bioconjugate Chemistry*, 27:1293-1304.

Moore et al. (1988). "Introduction of soluble protein into the class I pathway of antigen processing and presentation." *Cell*, 54:777-85.

Pramanick et al. (2013). "Excipient Selection in Parenteral Formulation Development." *Pharma Times*, 45(3):65-77.

Roy et al. (2013). "Synthesis of DNA/RNA and Their Analogs via Phosphoramidite and H-Phosphonate Chemistries," *Molecules*, 18(11):14268-14284.

International Search Report and Written Opinion dated May 9, 2016, for PCT Patent Application No. PCT/US2016/014635, 13 pages.

International Preliminary Report on Patentability dated Aug. 3, 2017 for PCT Application No. PCT/US2016/014635, filed on Jan. 22, 2016, 8 pages.

U.S. Appl. No. 15/958,295, filed Apr. 20, 2018 by Ott et al.

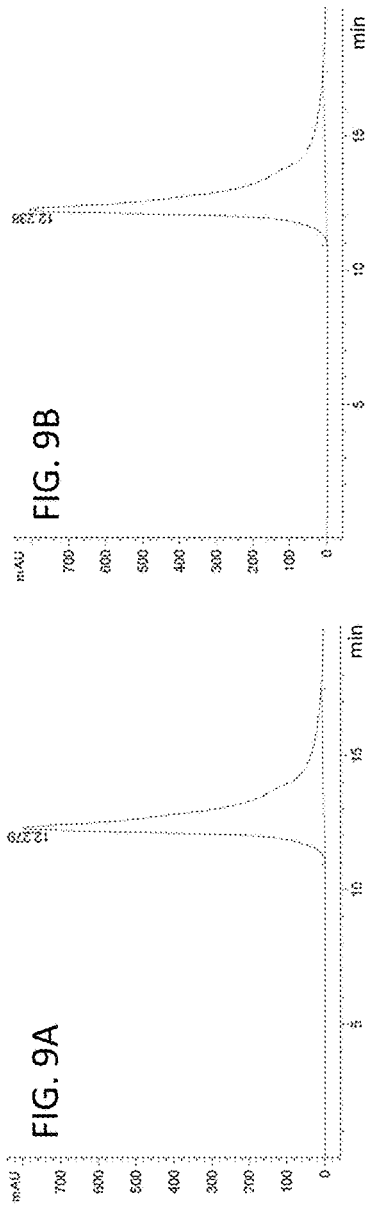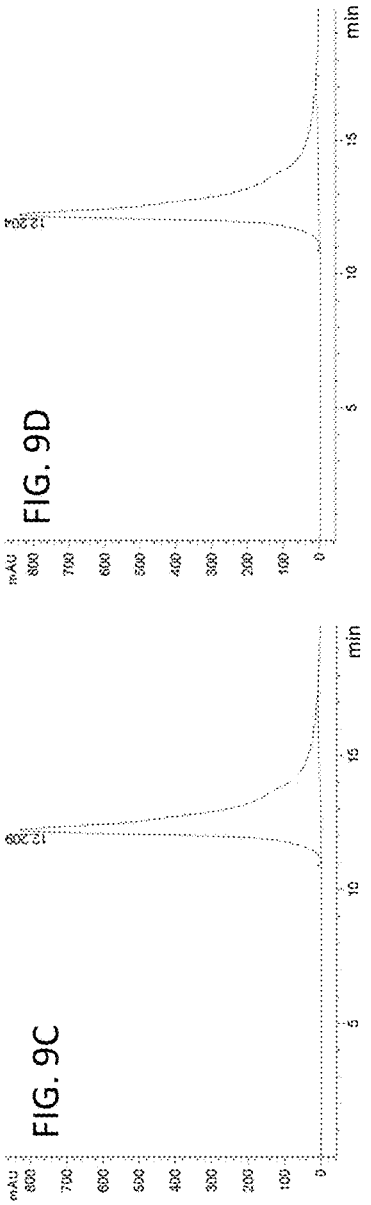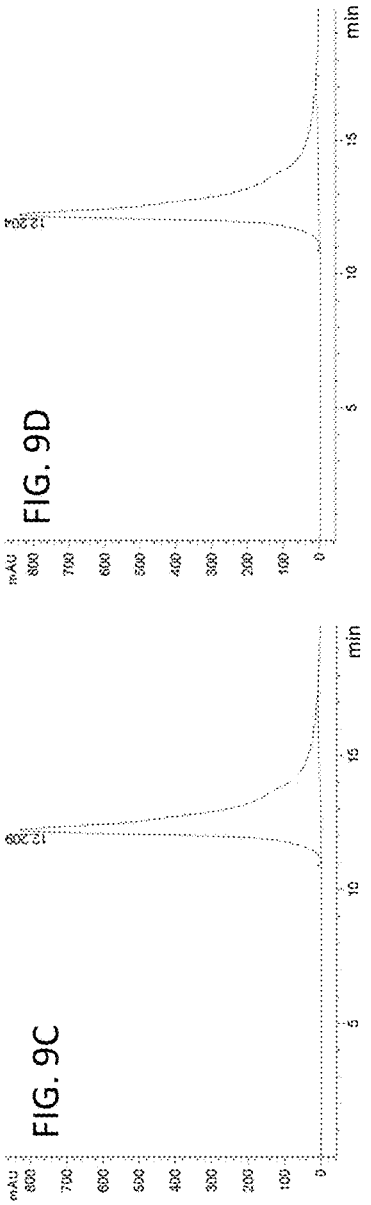

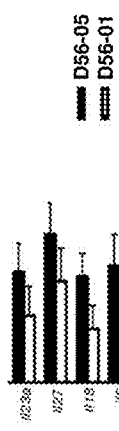
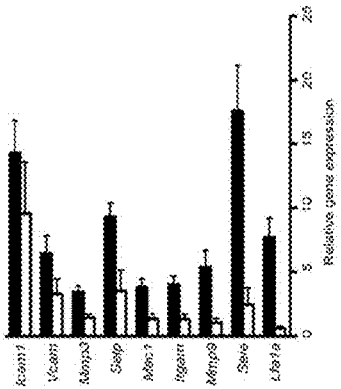
FIG. 11A
FIG. 11C
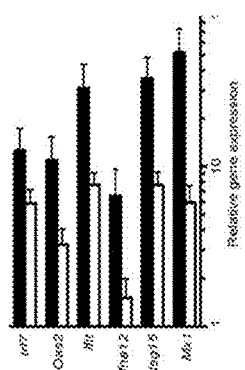
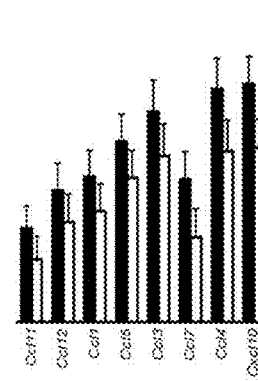
FIG. 11B
FIG. 11D

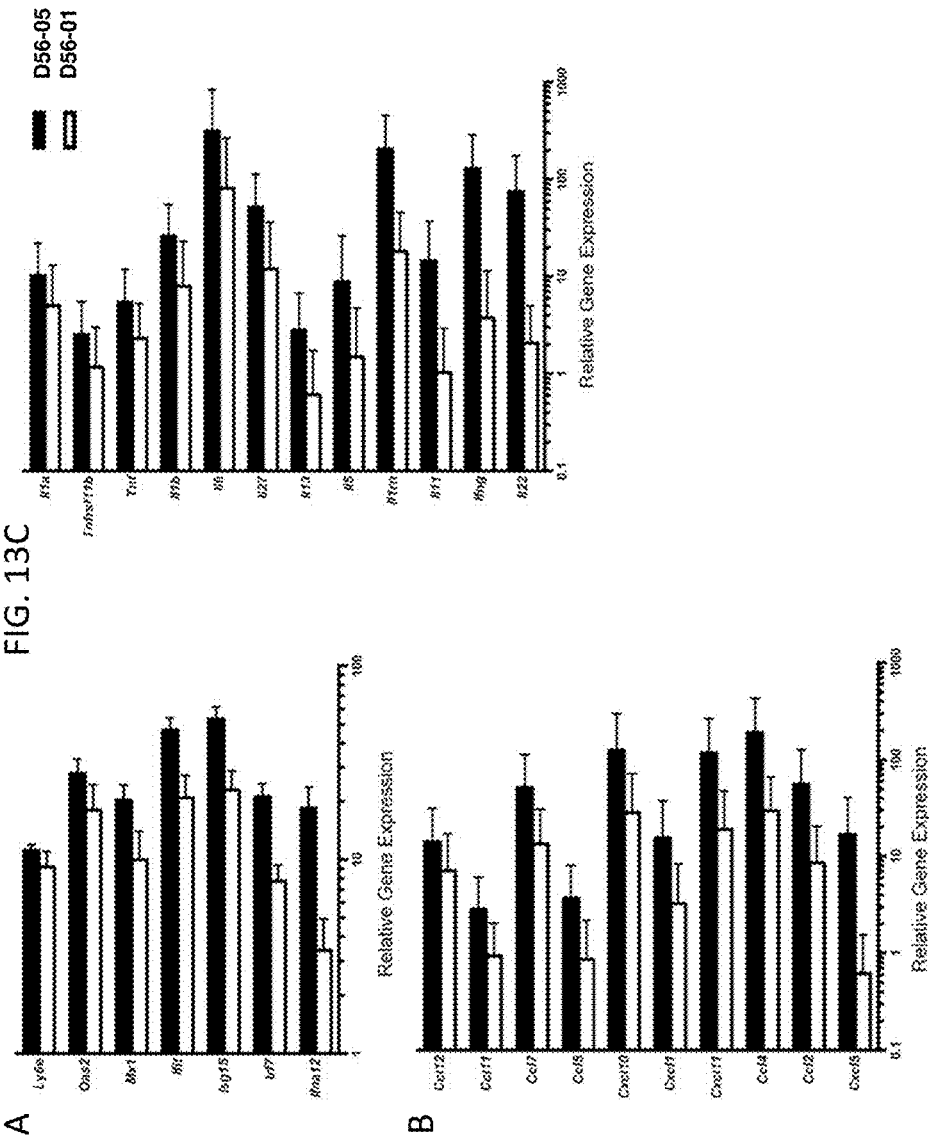

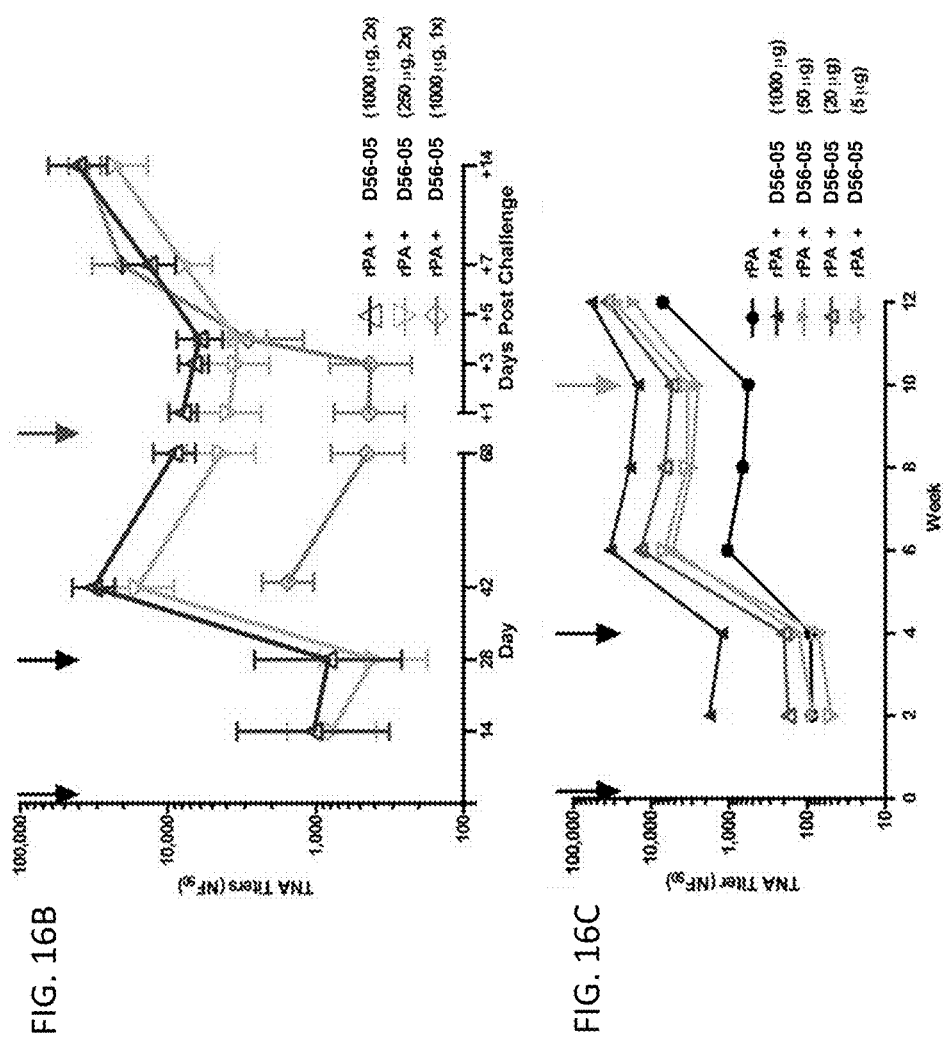

LINEAR CHIMERIC COMPOUNDS AND METHODS OF USE THEREOF

CROSS-REFERENCE TO RELATED APPLICATIONS

This application is a continuation of U.S. application Ser. No. 15/004,860, filed Jan. 22, 2016, now U.S. Pat. No. 9,950,064, which claims the benefit of U.S. Provisional Application No. 62/107,291, filed Jan. 23, 2015, each of which is incorporated herein by reference in its entirety for all purposes.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 377882005601SEQLIST.txt, date recorded: Mar. 22, 2018, size: 7 KB).

FIELD

The present invention relates to branched and linear chimeric compounds containing both nucleic acid and non-nucleic acid moieties, as well as to polynucleotides. The present invention also relates to uses thereof for stimulating an immune response, and to methods for preparation of the branched chimeric compounds.

BACKGROUND

Toll-like receptors (TLRs) are a family of transmembrane proteins that recognize conserved microbial molecules, referred to as pathogen-associated molecular patterns, which are distinguishable from host molecules. As such TLRs play important roles in innate immune responses. TLR3, TLR7, TLR8, TLR9 and TLR13 are nucleic acid sensing TLRs.

Agonists and antagonists of TLRs find use in modulating immune responses. TLR agonists are typically employed to stimulate immune responses, whereas TLR antagonists are typically employed to inhibit immune responses (Gosu et al., *Molecules*, 17:13503-13529, 2012). TLR9, which is expressed by various antigen presenting cells, recognizes unmethylated CpG dinucleotides within nucleic acids. Thus polynucleotides containing an unmethylated CpG dinucleotide can make effective adjuvants through their ability to activate TLR9. Additionally, chimeric compounds containing both a non-nucleic acid moiety and an unmethylated-CpG containing nucleic acid moiety are capable of stimulating immune responses.

The potency of a TLR9 agonist is dependent upon the length of the nucleic acid moiety, the residues flanking the unmethylated-CpG dinucleotide, and the efficacy of antigen presenting cell uptake (Marshall et al., *Nucleic Acids Research*, 31:5122-5133, 2003). Certain branched chimeric compounds, in which multiple polynucleotides or linear chimeric compounds are attached to a multivalent carrier moiety (e.g., a polysaccharide), have elicited enhanced immune responses relative to the unconjugated polynucleotides or linear chimeric compounds (Marshall et al., supra). A highly branched hydrophilic polysaccharide, marketed as FICOLL® by GE Healthcare, can be used as a multivalent carrier moiety for branched chimeric compounds. However, traditional linker moieties used in conjugation of FICOLL® are hydrophobic, which can cause precipitation of the synthetic intermediates containing FICOLL®. This negatively impacts the processes used to manufacture the branched chimeric compounds and subsequent ability to store the final products. Moreover, the therapeutic utility of a synthetic TLR agonist is influenced by its toxicity.

There remains a need for polynucleotides and chimeric compounds with potent immunostimulatory activity. Additionally, there remains a need for potent chimeric compounds that can be reproducibly manufactured. Polynucleotides and chimeric compounds with acceptable toxicity profiles are particularly desirable.

SUMMARY

The present disclosure relates to branched and linear chimeric compounds containing both nucleic acid and non-nucleic acid moieties, as well as to polynucleotides. The present disclosure also relates to uses thereof for stimulating an immune response, and to methods for preparation of the branched chimeric compounds.

In one aspect, the present disclosure provides branched chimeric compounds of formula (I): $[D-L^1-L^2-(PEG)-L^3]_x$-F (I), wherein: D is a polynucleotide or a linear chimeric compound; $L^1$ is a first linker comprising an alkylthio group; $L^2$ is a second linker comprising a succinimide group; $L^3$ is a third linker comprising an amide group; PEG is of the formula —$(OCH_2CH_2)_n$—, where n is an integer from 2 to 80; x is an integer from 3 to 300; and F is a branched copolymer of sucrose and epichlorohydrin having a molecular weight of about 100,000 to about 700,000 daltons and is connected to $L^3$ via an ether group, wherein the polynucleotide of D comprises the nucleotide sequence: 5'-TCG-GCGC AACGTTC TCGGCGC-3' (SEQ ID NO: 1), wherein the polynucleotide is less than 50 nucleotides in length, and wherein one or more linkages between the nucleotides and between the 3'-terminal nucleotide and $L^1$ are phosphorothioate ester linkages; and wherein the linear chimeric compound of D comprises three nucleic acid moieties and two hexaethylene glycol (HEG) spacers as 5'-TCGGCGC-3'-HEG-5'-AACGTTC-3'-HEG-5'-TCGGCGC-3' (SEQ ID NO:2), wherein the linear chimeric compound contains less than 50 nucleotides, and wherein one or more linkages between the nucleotides, between the nucleotides and the HEG spacers and between the 3'-terminal nucleotide and $L^1$ are phosphorothioate ester linkages. In some embodiments, x is 20-300, 90-150, or 100-140. In some embodiments, $L^2$ is

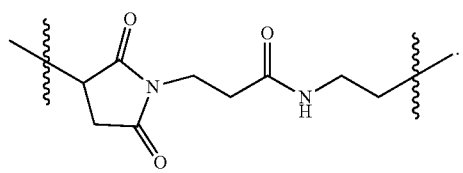 [SMILES: *CCNC(=O)CCN1C(=O)CC(*)C1=O]

In some embodiments, $L^3$ is:

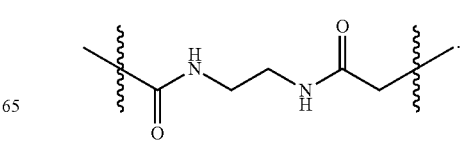

In some embodiments, wherein $L^3$ is

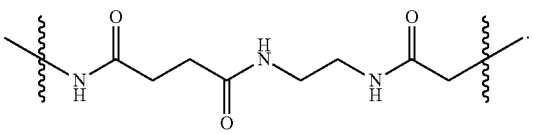 [SMILES: *CC(=O)NCCNC(=O)CCC(=O)N*]

In some embodiments, n of the formula —(OCH$_2$CH$_2$)$_n$— is 6, 24, 45 or 70. In some embodiments, F has a molecular weight of about 300,000 to about 500,000 daltons. In some embodiments, F is FICOLL® PM 400 (polymer marketed by GE Healthcare). In some embodiments, D is the polynucleotide consisting of the nucleotide sequence 5'-TCG-GCGC AACGTTC TCGGCGC-3' (SEQ ID NO:1). In some embodiments, D is the linear chimeric compound consisting of 5'-TCGGCGC-3'-HEG-5'-AACGTTC-3'-HEG-5'-TCG-GCGC-3' (SEQ ID NO:2). In some embodiments, $L^1$ is —(CH$_2$)$_m$—S—, wherein m is an integer from 2 to 9. In some embodiments, x is from 20 to 200. In some embodiments, x is from 90 to 150, n is 6 and m is 3 or 6. In some embodiments, all of the linkages between the nucleotides, where present the linkages between the nucleotides and the HEG spacers, and the linkage between the 3'-terminal nucleotide and $L^1$ are phosphorothioate ester linkages. The CpG dinucleotides of the polynucleotides or the nucleic acid moieties of the linear chimeric compounds are unmethylated.

In another aspect the present disclosure provides isolated polynucleotides comprising the nucleotide sequence 5'-TCGGCGC AACGTTC-3' (SEQ ID NO:3), wherein the polynucleotide is less than 50 nucleotides in length, and wherein one or more linkages between the nucleotides are phosphorothioate ester linkages. In a related aspect, the present disclosure provides isolated polynucleotides comprising the nucleotide sequence 5'-TCGGCGC AACGTTC TCGGCGC-3' (SEQ ID NO:1), wherein the polynucleotide is less than 50 nucleotides in length, and one or more linkages between the nucleotides are phosphorothioate ester linkages. In some embodiments, the polynucleotide consists of the nucleotide sequence of 5'-TCGGCGC AACGTTC TCGGCGC-3' (SEQ ID NO:1). In some embodiments, the polynucleotide is single-stranded. In some embodiments, the polynucleotide is a 2'-deoxyribopolynucleotide. In some embodiments, all of the linkages are phosphorothioate ester linkages. The CpG dinucleotides of the polynucleotides are unmethylated.

In a further aspect, the present disclosure provides linear chimeric compounds comprising two nucleic acid moieties and a hexaethylene glycol (HEG) spacer as 5'-TCGGCGC-3'-HEG-5'-AACGTTC-3' (SEQ ID NO:4), wherein the linear chimeric compound contains fewer than 50 nucleotides, and wherein one or more linkages between the nucleotides and between the nucleotides and the HEG spacer are phosphorothioate ester linkages. In a related aspect, the present disclosure provides linear chimeric compounds comprising three nucleic acid moieties and two hexaethylene glycol (HEG) spacers as 5'-TCGGCGC-3'-HEG-5'-AACGTTC-3'-HEG-5'-TCGGCGC-3' (SEQ ID NO:2), wherein the linear chimeric compound contains fewer than 50 nucleotides, and wherein one or more linkages between the nucleotides and between the nucleotides and the HEG spacers are phosphorothioate ester linkages. In some embodiments, the linear chimeric compound consists of 5'-TCGGCGC-3'-HEG-5'-AACGTTC-3'-HEG-5'-TCGGCGC-3' (SEQ ID NO:2). In some embodiments, the nucleic acid moieties are 2'-deoxyribopolynucleotides. In some embodiments, all of the linkages are phosphorothioate ester linkages.

Moreover, the present disclosure provides pharmaceutical compositions comprising (i) a pharmaceutically acceptable excipient, and (ii) one of the group consisting of the branched chimeric compound, the polynucleotide, and the linear chimeric compound of any of the preceding paragraphs of the summary. In some embodiments, the branched chimeric compound, the polynucleotide and the linear chimeric compound are each capable of stimulating cytokine production by mammalian leukocytes, comprising one or more of the group consisting of: stimulating production of IFN-alpha by human peripheral blood mononuclear cells; stimulating production of IL-6 by human B lymphocytes; and stimulating production of one or both of IL-12p40 and IL-6 by mouse splenocytes. In some embodiments, the branched chimeric compound, the polynucleotide and the linear chimeric compound are each capable of stimulating proliferation of mammalian B lymphocytes. In some embodiments, the composition is a sterile solution. In other embodiments, the composition is a sterile lyophilized solid. In some embodiments, the composition further comprises an antigen that is not covalently-linked to the branched chimeric compound, the polynucleotide and the linear chimeric compound present in the composition (e.g., the antigen is mixed with rather than conjugated to the branched chimeric compound, the polynucleotide or the linear chimeric compound present in the composition). branched chimeric compound, the polynucleotide and the linear chimeric compound present in the composition. In some embodiments, the antigen is a microbial antigen, an allergen or a tumor antigen. In some embodiments, the antigen is an isolated or recombinant protein. In some embodiments, the composition is essentially endotoxin-free.

Additionally the present disclosure provides methods of stimulating an immune response in a mammalian subject, comprising administering to a mammalian subject a pharmaceutical composition as described above in an amount sufficient to stimulate an immune response in the mammalian subject. In some embodiments, stimulating an immune response comprises one or more of the group consisting of: stimulating IFN-alpha production; stimulating IL-6 production; stimulating B lymphocyte proliferation; stimulating interferon pathway-associated gene expression; stimulating chemoattractant-associated gene expression; and stimulating plasmacytoid dendritic cell (pDC) maturation. In some embodiments, when the pharmaceutical composition further comprises an antigen, stimulating an immune response comprises inducing an antigen-specific antibody response, wherein titer of the antigen-specific antibody response is higher when the antigen is administered in combination with the branched chimeric compound, the polynucleotide or the linear chimeric compound than when the antigen is administered without the branched chimeric compound, the polynucleotide or the linear chimeric compound. In some embodiments, titer of the antigen-specific antibody response is higher when the antigen is administered in combination with the branched chimeric compound than when the antigen is administered with the corresponding linear chimeric compound.

The present disclosure provides a plurality of methods for using a pharmaceutical composition described above in a mammalian subject, such as a human patient. In one aspect, methods are provided for inducing an antigen-specific antibody response in a mammalian subject, comprising administering to a mammalian subject the pharmaceutical composition in an amount sufficient to induce an antigen-specific antibody response in the mammalian subject. In one aspect, methods are provided for preventing an infectious disease in a mammalian subject, comprising administering to a mammalian subject the pharmaceutical composition in an amount sufficient to prevent an infectious disease in the mammalian subject. In one aspect, methods are provided for treating or preventing an infectious disease in a mammalian subject, comprising administering to a mammalian subject the pharmaceutical composition in an amount sufficient to treat or prevent an infectious disease in the mammalian subject. In one aspect, methods are provided for ameliorating a symptom of an infectious disease in a mammalian subject, comprising administering to a mammalian subject the pharmaceutical composition in an amount sufficient to ameliorate a symptom of an infectious disease in the mammalian subject. In one aspect, methods are provided for ameliorating a symptom of an IgE-related disorder in a mammalian subject, comprising administering to the mammalian subject the pharmaceutical composition in an amount sufficient to ameliorate a symptom of an IgE-related disorder in the mammalian subject. In one aspect, methods are provided for treating or preventing an IgE-related disorder in a mammalian subject, comprising administering to the mammalian subject the pharmaceutical composition in an amount sufficient to treat or prevent an IgE-related disorder in the mammalian subject. In one aspect, methods are provided for a treating cancer in a mammalian subject, comprising administering to a mammalian subject the pharmaceutical composition in an amount sufficient to treat cancer in the mammalian subject. In some embodiments, treating cancer comprises shrinking size of a solid tumor. In some embodiments, treating cancer comprises reducing viable cancer cell numbers. In some embodiments, treating cancer comprises prolonging survival of a cancer patient. In some embodiments, the cancer is a carcinoma (e.g., head and neck squamous cell carcinoma). In some embodiments, the cancer is a sarcoma. In some embodiments, the cancer is a melanoma. In some embodiments, the cancer is lymphoma.

Moreover the present disclosure provides methods for preparing a branched chimeric compound of formula (I): [D-$L^1$-$L^2$-(PEG)-$L^3$]$_x$-F (I), wherein: D is a polynucleotide or a linear chimeric compound; $L^1$ is a first linker comprising an alkylthio group; $L^2$ is a second linker comprising a succinimide group; $L^3$ is a third linker comprising an amide group; PEG is a polyethylene glycol; x is an integer from 3 to 300; and F is a branched copolymer of sucrose and epichlorohydrin having a molecular weight of about 100,000 to about 700,000 daltons and is connected to $L^3$ via an ether group, wherein the polynucleotide comprises the nucleotide sequence: 5'-TCGGCGC AACGTTC TCGGCGC-3' (SEQ ID NO:1), wherein the polynucleotide is less than 50 nucleotides in length, and wherein one or more linkages between the nucleotides and between the 3'-terminal nucleotide and $L^1$ are phosphorothioate ester linkages, and wherein the linear chimeric compound comprises three nucleic acid moieties and two hexaethylene glycol (HEG) spacers as 5'-TCGGCGC-3'-HEG-5'-AACGTTC-3'-HEG-5'-TCGGCGC-3' (SEQ ID NO:2), wherein the linear chimeric compound contains less than 50 nucleotides, and wherein one or more linkages between the nucleotides, between the nucleotides and the HEG spacers and between the 3'-terminal nucleotide and $L^1$ are phosphorothioate ester linkages, wherein the method comprises: reacting a compound of the formula D-$L^{1a}$-SH, where D is as defined for formula (I) and $L^{1a}$ is $(CH_2)_m$ where m is an integer from 2 to 9, with a compound of formula (II): [$L^{2a}$-(PEG)-$L^3$]$_y$-F (II), wherein $L^3$, PEG and F are as defined for formula (I); $L^{2a}$ is

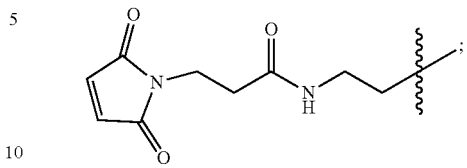

and y is an integer from 3 to 350. In some embodiments, x is 20-300, 90-150, or 100-140; y is 20-350, 30-300, 155-215, or 165-205. In some embodiments, the methods further comprise reacting a compound of the formula D-$L^{1a}$-SS-$L^{1a}$-OH with a reducing agent to produce the compound of the formula D-$L^{1a}$-SH. In some embodiments, the methods further comprise reacting a compound of the formula (III): [$NH_2CH_2CH_2NHC(O)CH_2$]$_z$—F (III), wherein F is as defined for formula (I) and z is an integer from 3 to 400, with a compound of the formula $L^{2a}$-(PEG)-$L^{3a}$-Lv, where $L^{2a}$ and PEG are as defined for formula (II); $L^{3a}$ is —NHC(O)$CH_2CH_2C(O)$— or —C(O)—; and Lv is a leaving group, to form the compound of the formula (II). In some embodiments, z is 20-400, 50-300, 190-250, or 200-240. In some embodiments, Lv is (2,5-dioxopyrrolidin-1-yl)oxy. In some embodiments, the methods D is 5'-TCGGCGC-3'-HEG-5'-AACGTTC-3'-HEG-5'-TCGGCGC-3' (SEQ ID NO:2). Variations in the polynucleotide and linear chimeric compound of D suitable for use in the methods of the present disclosure are more fully described in the preceding paragraphs.

BRIEF DESCRIPTION OF THE DRAWINGS

FIG. 9A-D provide results from the size exclusion chromatography-high performance liquid chromatography analysis of purified D56-03. FIG. 9A is from Pilot Lot 4, FIG. 9B is from Pilot Lot 5 Part 1, FIG. 9C is from Pilot Lot 5 Part 2, and FIG. 9D is from Pilot Lot 5 Combined. The D56-03 retention time was 12.2 min. TCEP ((tris(2-carboxyethyl)phosphine) was run as a control, and eluted as a single peak with a retention time of 14.6 min.

FIG. 11A-E show D56-05 nanoparticles, compared with monomeric D56-01, enhance expression of IFN-regulated, chemokine, cytokine, and transendothelial migration-related genes, leading to enhanced cell recruitment in injection site muscle. BALB/c mice (n=6/group) were injected i.m. with 10 mg D56-05 or D56-01 (CpG-ODN-based doses). Injection site muscle was collected 6 hours following injection to assess IFN-regulated (FIG. 11A), chemokine (FIG. 11B), cytokine (FIG. 11C), and transendothelial migration-related (FIG. 11D) gene expression. Gene expression relative to PBS-injected controls was determined by ΔΔCt evaluation ($2^{-\Delta\Delta Ct}$). Data are shown as mean of individual samples with 95% CI from a single experiment. (FIG. 11E) Relative proportions of various cell populations in muscle (normalized to total cells) of D56-05-injected versus D56-01-injected mice (10 mg) at 12-24 hours were evaluated by flow cytometry. Following light scatter gating and exclusion of lymphocytes (CD3/CD19/CD49b dump channel), cell populations were identified as follows: macrophages ($CD11b^+/CD11c^-/F4/80^+/Ly6C^+/Ly6G^-$), monocytes ($CD11b^+/CD11c^-/F4/80^-/Ly6C^+/Ly6G^-$), neutrophils ($CD11b^+/CD11c^-/Ly6G^+$), total $CD11b^+$ cells, and cDCs ($CD11b^-/CD11c^+$). Data, shown as means with SEM, are an average of two independent experiments.

In FIG. 12A wild-type (C57BL/6) or TLR92/2 mice (n=6) were injected i.m. with 10 mg D56-05, and injection site muscle was collected 6 hours following injection to determine gene expression. Individual gene fold induction was calculated relative to PBS-injected controls. Data are shown as means with SEM. In FIG. 12B C57BL/6 or TLR92/2 mice (n=8-10) were immunized i.m. with 5 mg rPA in combination with 10 mg D56-05, and. TNA titer levels at day 14 are shown as means. ***$p<0.001$ by Mann-Whitney U test.

FIG. 13A-C show D56-05 nanoparticles enhance IFN-regulated, chemokine, and cytokine genes. BALB/c mice (n=6) were immunized s.c. with 10 mg D56-05 or D56-01. Popliteal lymph nodes were collected 18 hours following immunization to assess IFN-regulated (FIG. 13A), chemokine (FIG. 13B), and cytokine (FIG. 13C) gene expression. Gene expression relative to PBS-injected controls was determined by ΔΔCt evaluation ($2^{-\Delta\Delta Ct}$). Data are shown as means of individual samples with 95% CI from a single experiment.

In FIG. 15A-B titers 2 wk following initial immunization are shown as the mean with 95% CI, and are representative of three independent experiments. *$p<0.05$, ** $p<0.01$ by Kruskal-Wallis with Dunn posttest. FIG. 15C illustrates the correlation between anti-rPA IgG and TNA titer levels 2 wk following initial immunization. Spearman rank correlation. FIG. 15D shows TNA titer data (means) monitored throughout the study.

FIG. 16A-C illustrate that rPA/D56-05 vaccination induces a potent memory response, mediating complete protection from challenge with aerosolized B. anthracis spores in a monkey prophylactic anthrax challenge model. Cynomolgus macaques (n=6-8/group) were immunized i.m. (↓) with 10 mg rPA in combination with 1000 or 250 mg D56-05 on day 0 and/or 29 (13 or 23). A group (n=6) of nonvaccinated animals was also included. All monkeys were exposed to a target dose of 200 LD50 equivalents of aerosolized B. anthracis spores on day 69, 70, or 71 (↓). In FIG. 16A survival was monitored twice daily for 28 days following challenge. In FIG. 16B TNA titer levels were monitored throughout the study and for 4 wk following challenge. Data are shown as mean with 95% CI. Cynomolgus macaques (n=4-6) were immunized with 10 mg rPA alone or in combination with 1000, 50, 20, or 5 mg D56-05 on days 0 and 28 (↓). All monkeys received 25 mg rPA alone 10 wk following initial immunization (↓). In FIG. 16C TNA titer levels were monitored for 12 wk with titers shown as means.

DETAILED DESCRIPTION

Figure 1:
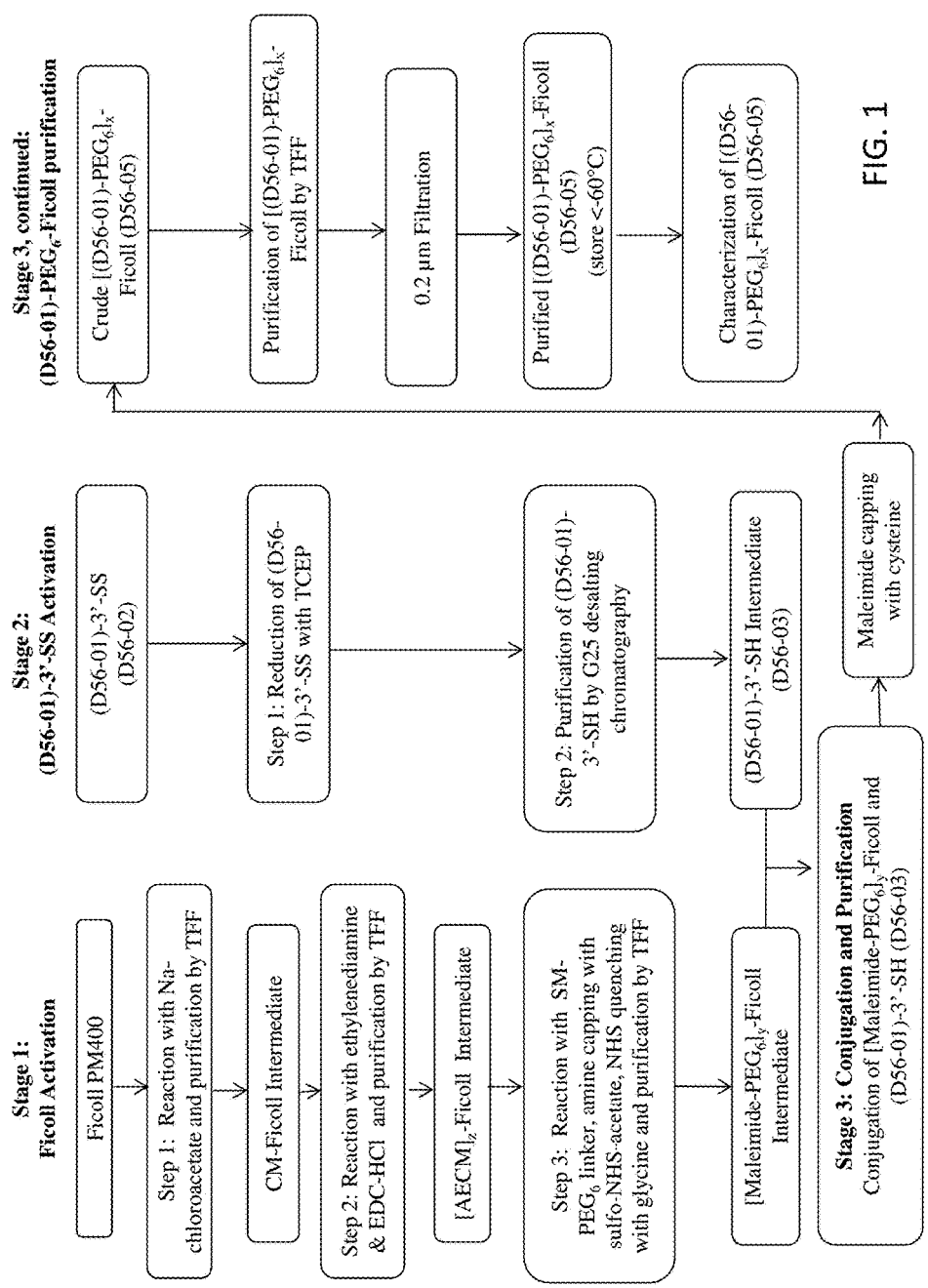
FIG. 1 provides a flow chart for the manufacturing scheme used to prepare an exemplary branched chimeric compound, D56-05, (aka [(D56-01)-$PEG_6$]$_x$-FICOLL).

The present invention relates to polynucleotides, as well as linear and branched chimeric compounds containing both nucleic acid and non-nucleic acid moieties. The present invention also relates to uses thereof for stimulating an immune response, and to methods for preparation of the branched chimeric compounds.

General Methods and Definitions

The practice of the present disclosure will employ, unless otherwise indicated, conventional techniques of molecular biology, microbiology, cell biology, biochemistry, nucleic acid chemistry, and immunology, which are within the skill of the art. Such techniques are fully described in the literature, see for example: *Animal Cell Culture*, sixth edition (Freshney, Wiley-Blackwell, 2010); *Antibodies, A Laboratory Manual*, second edition (Greenfield, ed., Cold Spring Harbor Publications, 2013); *Bioconjugate Techniques*, third edition (Hermanson, Academic Press, 1996); *Current Protocols in Cell Biology* (Bonifacino et al., ed., John Wiley & Sons, Inc., 1996, including supplements through 2014); *Current Protocols in Immunology* (Coligan et al., eds., John Wiley & Sons, Inc., 1991 including supplements through 2014); *Current Protocols in Molecular Biology* (Ausubel et al., eds., John Wiley & Sons, Inc., 1987, including supplements through 2014); *Current Protocols in Nucleic Acid Chemistry* (Egli et al., ed., John Wiley & Sons, Inc., 2000, including supplements through 2014); *Molecular Cloning: A Laboratory Manual*, third edition (Sambrook and Russell, Cold Spring Harbor Laboratory Press, 2001); *Molecular Cloning: A Laboratory Manual*, fourth edition (Green and Sambrook, Cold Spring Harbor Laboratory Press, 2012); *Oligonucleotide Synthesis: Methods and Applications* (Herdewijn, ed., Humana Press, 2004); *Protocols for Oligonucleotides and Analogs, Synthesis and Properties* (Agrawal, ed., Humana Press, 1993); and *Using Antibodies: A Laboratory Manual* (Harlow and Lane, Cold Spring Harbor Laboratory Press, 1998).

As used interchangeably herein, the terms "polynucleotide," "oligonucleotide" and "nucleic acid" include single-stranded DNA (ssDNA), double-stranded DNA (dsDNA), single-stranded RNA (ssRNA) and double-stranded RNA (dsRNA), modified oligonucleotides and oligonucleosides, or combinations thereof. The polynucleotide can be linear, branched, or circularly configured, or the polynucleotide can contain one or more linear, branched, and/or circular segments. Polynucleotides are polymers of nucleosides joined, generally, through phosphodiester linkages, although alternate linkages, such as phosphorothioate esters may also be used. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, thymidine, and deoxycytidine. The four nucleoside units (or bases) in RNA are called adenosine, guanosine, uridine and cytidine. A nucleotide is a phosphate ester of a nucleoside.

The polynucleotides, linear chimeric compounds and branched chimeric compounds of the present disclosure contain from 14 to 50 nucleotides. In some embodiments, the number of nucleotides is greater than (lower limit) 13, 14, 15, 16, 17, 18, 19, 20, 21, 22, 23, 24, 25, 30, 35, 40 or 45. In some embodiments, the number of nucleotides is less than (upper limit) 51, 50, 45, 40, 35, 30, 25 24, 23, 22, 21 or 20. That is, the number of nucleotides is in the range of about 14 to 50 in which the lower limit is less than the upper limit.

The term "3'" generally refers to a region or position in a polynucleotide 3' (downstream) from another region or position in the same polynucleotide.

The term "5'" generally refers to a region or position in a polynucleotide or oligonucleotide 5' (upstream) from another region or position in the same polynucleotide or oligonucleotide.

The terms "individual" and "subject" refer to mammals. "Mammals" include, but are not limited to, humans, non-human primates (e.g., monkeys), farm animals, sport animals, rodents (e.g., mice and rats) and pets (e.g., dogs and cats).

The term "antigen" refers to a substance that is recognized and bound specifically by an antibody or by a T cell antigen receptor. Antigens can include peptides, polypeptides, proteins, glycoproteins, polysaccharides, complex carbohydrates, sugars, gangliosides, lipids and phospholipids; portions thereof and combinations thereof. Antigens when present in the compositions of the present disclosure can be synthetic or isolated from nature. Antigens suitable for administration in the methods of the present disclosure include any molecule capable of eliciting an antigen-specific B cell or T cell response. Haptens are included within the scope of "antigen." A "hapten" is a low molecular weight compound that is not immunogenic by itself but is rendered immunogenic when conjugated with a generally larger immunogenic molecule (carrier).

"Polypeptide antigens" can include purified native peptides, synthetic peptides, recombinant peptides, crude peptide extracts, or peptides in a partially purified or unpurified active state (such as peptides that are part of attenuated or inactivated viruses, microorganisms or cells), or fragments of such peptides. Polypeptide antigens are preferably at least six amino acid residues in length.

As used herein, the term "immunogenic" refers to an agent (e.g., polypeptide antigen) that elicits an adaptive immune response upon administration under suitable conditions to a mammalian subject. The immune response may be B cell (humoral) and/or T cell (cellular) response.

"Adjuvant" refers to a substance which, when mixed with an immunogenic agent such as antigen, nonspecifically enhances or potentiates an immune response to the agent in the recipient upon exposure to the mixture.

The term "agonist" is used in the broadest sense and includes any molecule that activates signaling through a receptor. For instance, a TLR9 agonist binds a TLR9 receptor and activates a TLR9-signaling pathway.

The term "antagonist" is used in the broadest sense, and includes any molecule that blocks a biological activity of an agonist. For instance, a TLR9 antagonist blocks a TLR9-signaling pathway.

The terms "immunostimulatory sequence" and "ISS" refer to a nucleic acid sequence that stimulates a measurable immune response (e.g., measured in vitro, in vivo, and/or ex vivo). For the purpose of the present disclosure, the term ISS refers to a nucleic acid sequence comprising an unmethylated CG dinucleotide. Conversely, the terms "immunoinhibitory sequence" and "IIS" refer to a nucleic acid sequence that inhibits a measurable immune response (e.g., measured in vitro, in vivo, and/or ex vivo). Examples of measurable immune responses include, but are not limited to, antigen-specific antibody production, cytokine secretion, lymphocyte activation and lymphocyte proliferation.

The terms "CpG" and "CG" are used interchangeably herein to refer to a cytosine and guanine separate by a phosphate. These terms refer to a linear sequence as opposed to base-pairing of cytosine and guanine. The polynucleotides, linear chimeric compounds and branched chimeric compounds of the present disclosure contain at least one unmethylated CpG dinucleotide. That is the cytosine in the CpG dinucleotide is not methylated (i.e., is not 5-methyl-cytosine).

The terms "antisense" and "antisense sequence" as used herein refer to a non-coding strand of a polynucleotide having a sequence complementary to the coding strand of mRNA. In preferred embodiments, the polynucleotides of the present disclosure are not antisense sequences, or RNAi molecules (miRNA and siRNA). That is in preferred embodiments, the polynucleotides of the present disclosure do not have significant homology (or complementarity) to transcripts (or genes) of the mammalian subjects in which they will be used. For instance, a polynucleotide of the present disclosure for modulating an immune response in a human subject is preferably less than 80% identical over its length to nucleic acid sequences of the human genome (e.g., a polynucleotide that is 50 nucleotides in length would share no more than 40 of the 50 bases with a human transcript). That is, in preferred embodiments, the polynucleotides are less than 80%, 75%, 70%, 65%, 60%, 55%, 50%, 45%, 40%, 35%, 30%, 25% or 20%, identical to nucleic acid sequences of mammalian subjects (e.g., such as humans, nonhuman primates, farm animals, dogs, cats, rabbits, rats, mice, etc.) in which they are to be used.

"Stimulation" of a response or parameter includes eliciting and/or enhancing that response or parameter when compared to otherwise same conditions except for a parameter of interest, or alternatively, as compared to another condition (e.g., increase in TLR-signaling in the presence of a TLR agonist as compared to the absence of the TLR agonist). For example, "stimulation" of an immune response means an increase in the response.

"Inhibition" of a response or parameter includes blocking and/or suppressing that response or parameter when compared to otherwise same conditions except for a parameter of interest, or alternatively, as compared to another condition (e.g., decrease in TLR-signaling in the presence of a TLR agonist and a TLR antagonist as compared to the presence of the TLR agonist in the absence of the TLR antagonist). For example, "inhibition" of an immune response means a decrease in the response.

An "effective amount" of an agent disclosed herein is an amount sufficient to carry out a specifically stated purpose. An "effective amount" may be determined empirically and in a routine manner, in relation to the stated purpose. An "effective amount" or an "amount sufficient" of an agent is that amount adequate to effect a desired biological effect, such as a beneficial result, including a beneficial clinical result. The term "therapeutically effective amount" refers to an amount of an agent (e.g., TLR inhibitor) effective to "treat" a disease or disorder in a subject (e.g., a mammal such as a human). In the case of allergy, a therapeutically effective amount of the agent reduces a sign or symptom of the allergy.

The terms "treating" or "treatment" of a disease refer to executing a protocol, which may include administering one or more drugs to an individual (human or otherwise), in an effort to alleviate signs or symptoms of the disease. Thus, "treating" or "treatment" does not require complete alleviation of signs or symptoms, does not require a cure, and specifically includes protocols that have only a palliative effect on the individual. As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival of an individual not receiving treatment.

"Palliating" a disease or disorder means that the extent and/or undesirable clinical manifestations of the disease or disorder are lessened and/or time course of progression of the disease or disorder is slowed, as compared to the expected untreated outcome. Especially in the allergy context, palliation may occur upon stimulation of a Th1 immune response against an allergen(s). Further, palliation does not necessarily occur by administration of one dose, but often occurs upon administration of a series of doses. Thus, an amount sufficient to palliate a response or disorder may be administered in one or more doses.

As used herein and in the appended claims, the singular forms "a," "an" and "the" include plural referents unless otherwise indicated or clear from context. For example, "a polynucleotide" includes one or more polynucleotides.

Reference to "about" a value or parameter describes variations of that value or parameter. For example, description referring a molecular weight of about 400,000 daltons encompasses molecular weights of 360,000 to 440,000 daltons.

It is understood that aspects and embodiments described herein as "comprising" include "consisting of" and "consisting essentially of" embodiments.

I. Polynucleotides and Chimeric Compounds

The present disclosure provides polynucleotides, linear chimeric compounds and branched chimeric compounds useful, inter alia, for modulating an immune response in a mammalian subject, such as a human patient. The present disclosure is based, in part, on the discovery that some chimeric compounds containing nucleic acid moieties covalently bound to non-nucleic acid spacer moieties and/or a polymeric carrier have immunomodulatory activity (particularly in human cells), including in cases in which the nucleic acid moieties have a sequence that, if presented as an isolated polynucleotide, do not exhibit appreciable immunomodulatory activity (e.g., inferior or unmeasurable activity). In some embodiments, the immunomodulatory activity comprising immunostimulatory activity. In other embodiments, the immunomodulatory activity comprising immunoinhibitory activity.

A. Polynucleotides

In one aspect, polynucleotides comprising an unmethylated CpG dinucleotide are provided. The polynucleotides are capable of stimulating an immune response or constitute chimeric compounds for stimulating an immune response. In some embodiments, provided is a polynucleotide comprising the nucleotide sequence 5'-TCGGCGC AACGTTC-3' (SEQ ID NO:3). In some embodiments, provided is a polynucleotide comprising the nucleotide sequence 5'-TCG-GCGC AACGTTC TCGGCGC-3' (SEQ ID NO:1). In some embodiments, the polynucleotide is less than 50 nucleotides in length (i.e., the polynucleotide contains less than 50 nucleotides). In some embodiments, one or more linkages between the nucleotides are phosphorothioate ester linkages. In some embodiments, one or more linkages between the nucleotides are phosphodiester linkages. In preferred embodiments, 5'-TCGGCGC AACGTTC-3' (SEQ ID NO:3) or 5'-TCGGCGC AACGTTC TCGGCGC-3' (SEQ ID NO: 1) is located at the 5'-terminus of the polynucleotide (i.e., any additional nucleotides are added to the 3'-terminus). In some embodiments, the polynucleotide consists of the nucleotide sequence of 5'-TCGGCGC AACGTTC TCG-GCGC-3' (SEQ ID NO:1). In some embodiments, the polynucleotide is single-stranded. In some embodiments, the polynucleotide is a 2'-deoxyribopolynucleotide. In some embodiments, all of the linkages between the nucleotides are phosphorothioate ester linkages.

B. Linear Chimeric Compounds

In another aspect, linear chimeric compounds comprising a nucleic acid moiety comprising an unmethylated CpG dinucleotide are provided. The linear chimeric compounds are capable of stimulating an immune response or constitute branched chimeric compounds for stimulating an immune response. In some embodiments, provided is a linear chimeric compound comprising nucleic acid moieties and non-nucleic acid spacer moieties. In some embodiments, the linear chimeric compound comprises a core structure with the formula $N_1$-$Sp_1$-$N_2$ or $N_1$-$Sp_1$-$N_2$-$Sp_2$-$N_3$ (wherein $N_1$, $N_2$, and $N_3$ are nucleic acid moieties, $Sp_1$ and $Sp_2$ are non-nucleic acid spacer moieties, and $Sp_1$ and $Sp_2$ are covalently bound to exactly two nucleic acid moieties). In some of these embodiments, the linear chimeric compound comprises a core structure of the formula (5'-$N_1$-3')-$Sp_1$-(5'-$N_2$-3'). In some of these embodiments, the linear chimeric compound comprises a core structure of the formula (5'-$N_1$-3')-$Sp_1$-(5'-$N_2$-3')-$Sp_2$-(5'-$N_3$-3'). In some embodiments, the spacer moieties are a hexaethylene glycol (HEG). In some embodiments, the linear chimeric compound contains less than 50 nucleotides (i.e., sum of $N_1$, $N_2$, and optionally $N_3$ is less than 50). In some embodiments, each nucleic acid moiety N is less than 8 nucleotides in length, preferably 7 nucleotides in length.

In some embodiments, provided is linear chimeric compound comprising two nucleic acid moieties and a hexaethylene glycol spacer as 5'-TCGGCGC-3'-HEG-5'-AACGTTC-3' (SEQ ID NO:4), wherein the linear chimeric compound contains less than 50 nucleotides (i.e., sum of $N_1$ and $N_2$ is less than 50), and wherein one or more linkages between the nucleotides and between the nucleotides and the HEG spacer are phosphorothioate ester linkages. In some embodiments, provided is a linear chimeric compound comprising three nucleic acid moieties and two hexaethylene glycol spacers as 5'-TCGGCGC-3'-HEG-5'-AACGTTC-3'-HEG-5'-TCGGCGC-3' (SEQ ID NO:2), wherein the linear chimeric compound contains less than 50 nucleotides (i.e., sum of $N_1$, $N_2$, and $N_3$ is less than 50), and wherein one or more linkages between the nucleotides and between the nucleotides and the HEG spacers are phosphorothioate ester linkages. In some embodiments, 5'-TCGGCGC-3'-HEG-5'-AACGTTC-3' (SEQ ID NO:4) or 5'-TCGGCGC-3'-HEG-5'-AACGTTC-3'-HEG-5'-TCGGCGC-3' (SEQ ID NO:2) is located at the 5'-terminus of the linear chimeric compound (i.e., any additional nucleotides are added to the 3'-terminus). In some embodiments, provided is a linear chimeric compound consisting of 5'-TCGGCGC-3'-HEG-5'-AACGTTC-3'-HEG-5'-TCGGCGC-3' (SEQ ID NO:2). In some embodiments, one or more linkages between the nucleotides are phosphodiester linkages. In some embodiments, all of the internucleotide linkages and the linkages between nucleotides and the HEG spacers are phosphorothioate ester linkages. In some embodiments, the nucleic acid moieties of the linear chimeric compound are a 2'-deoxyribopolynucleotides. The CpG dinucleotides of the nucleic acid moieties of the linear chimeric compounds are unmethylated.

The present disclosure further provides linear chimeric compounds comprising one of the group consisting of:

```
                                        (SEQ ID NO: 9)
5'-TCGTTCG-3'-HEG-5'-TCGTTCG-3'-HEG-5'-AACGTTC-3'

(D56-16),
                                        (SEQ ID NO: 10)
5'-TCGTTCG-3'-HEG-5'-AACGTTC-3'-HEG-5'-TCGTTCG-3'

(D56-17),
                                        (SEQ ID NO: 11)
5'-TCGGCGC-3'-HEG-5'-TCGGCGC-3'-HEG-5'-AACGTTC-3'

(D56-18),
                                        (SEQ ID NO: 12)
5'-TCGCCGG-3'-HEG-5'-TCGCCGG-3'-HEG-5'-AACGTTC-3'

(D56-19),
                                        (SEQ ID NO: 13)
5'-TCGCCGG-3'-HEG-5'-AACGTTC-3'-HEG-5'-TCGCCGG-3'

(D56-20),
                                        (SEQ ID NO: 14)
5'-TCGATCG-3'-HEG-5'-TCGATCG-3'-HEG-5'-AACGTTC-3'

(D56-21),
                                        (SEQ ID NO: 15)
5'-TCGTCGT-3'-HEG-5'-TCGTCGT-3'-HEG-5'-AACGTTC-3'

(D56-22),
and
                                        (SEQ ID NO: 16)
5'-TCGTCGT-3'-HEG-5'-AACGTTC-3'-HEG-5'-TCGTCGT-3'

(D56-23).
```

In some of these embodiments, the linear chimeric compound contains less than 50 nucleotides, and 5'-TCG-3' of the nucleotide sequence is located at the 5'-terminus of the linear chimeric compound (i.e., any additional nucleotides are added to the 3'-terminus). In some embodiments, one or more linkages between the nucleotides and between the nucleotides and the HEG spacers are phosphorothioate ester linkages. In some embodiments, one or more linkages between the nucleotides are phosphodiester linkages. In some embodiments, all of the internucleotide linkages and the linkages between nucleotides and the HEG spacers are phosphorothioate ester linkages. In some embodiments, the nucleic acid moieties of the linear chimeric compound are a 2'-deoxyribopolynucleotides. The CpG dinucleotides of the nucleic acid moieties of the linear chimeric compounds are unmethylated.

C. Branched Chimeric Compounds

The branched chimeric compounds of the present disclosure comprise a polynucleotide or a linear chimeric compound that is covalently linked to a branched copolymer of sucrose and epichlorohydrin via a polyethylene glycol. The maleimide-activated FICOLL intermediate of the branched chimeric compounds of the present disclosure containing a polyethylene glycol have improved solubility and stability as compared to the intermediates of the previously disclosed branched chimeric compounds. Thus, the branched chimeric compounds of the present disclosure have improved manufacturability and storability as compared to the branched chimeric compounds C-137 and C-138 of U.S. Pat. Nos. 8,597,665, 8,114,418, and 7,785,610 of Dynavax Technologies Corporation. The branched chimeric compounds of the present disclosure also possess potent immunomodulatory activity (e.g., immunostimulatory or immunoinhibitory activity) and low toxicity in vitro and in vivo.

In some embodiments, this disclosure provides a branched chimeric compound of formula (I):

[D-L$^1$-L$^2$-(PEG)-L$^3$]$_x$-F    (I)

wherein:
D is a polynucleotide or a linear chimeric compound;
L$^1$ is a first linker comprising an alkylthio group;
L$^2$ is a second linker comprising a succinimide group;
L$^3$ is a third linker comprising an amide group;
PEG is a polyethylene glycol;
x is an integer from 3 to 300; and
F is a branched copolymer of sucrose and epichlorohydrin.

The branched chimeric compound of formula (I) comprises three or more polynucleotides or linear chimeric compounds D linked to a multivalent moiety F via a polyethylene glycol (PEG) and various linkers L$^1$, L$^2$ and L$^3$. The polynucleotide or nucleic acid moiety of the linear chimeric compound of D comprises an unmethylated CpG dinucleotide.

In some embodiments, D is a polynucleotide comprising the nucleotide sequence 5'-TCGGCGC-3'. In some embodiments, D is a polynucleotide comprising the nucleotide sequence 5'-TCGGCGC AACGTTC-3' (SEQ ID NO:3). In some embodiments, D is a polynucleotide comprising the nucleotide sequence 5'-TCGGCGC AACGTTC TCG-GCGC-3' (SEQ ID NO:1). In some embodiments, the polynucleotide of D is less than 50 nucleotides in length (i.e., the polynucleotide of D contains less than 50 nucleotides). In some embodiments, one or more linkages between the nucleotides and between the 3'-terminal nucleotide of D and L$^1$ are phosphorothioate ester linkages. In some embodiments, 5'-TCGGCGC AACGTTC-3' (SEQ ID NO:3) or 5'-TCGGCGC AACGTTC TCGGCGC-3' (SEQ ID NO:1) of D is located at the 5' terminus of the polynucleotide (i.e., any additional nucleotides are added to the 3'-terminus). In some embodiments, D is a polynucleotide consisting of the nucleotide sequence of 5'-TCGGCGC AACGTTC TCG-GCGC-3' (SEQ ID NO:1). In some embodiments, the polynucleotide of D is single-stranded. In some embodiments, the polynucleotide of D is a 2'-deoxyribopolynucleotide. In some embodiments, one or more linkages between the nucleotides are phosphodiester linkages. In some embodiments, all of the linkages between the nucleotides and the linkage between the 3'-terminal nucleotide of D and L$^1$ are phosphorothioate ester linkages. The CpG dinucleotides of the polynucleotide of D are unmethylated.

In some embodiments, D is a linear chimeric compound comprising nucleic acid moieties and non-nucleic acid spacer moieties. In some embodiments, the linear chimeric compound comprises a core structure with the formula $N_1$-$Sp_1$-$N_2$ or $N_1$-$Sp_1$-$N_2$-$Sp_2$-$N_3$ (wherein $N_1$, $N_2$, and $N_3$ are nucleic acid moieties, $Sp_1$ and $Sp_2$ are non-nucleic acid spacer moieties, and $Sp_1$ and $Sp_2$ are covalently bound to exactly two nucleic acid moieties). In some of these embodiments, the linear chimeric compound comprises a core structure of the formula (5'-$N_1$-3')-$Sp_1$-(5'-$N_2$-3'). In some of these embodiments, the linear chimeric compound comprises a core structure of the formula (5'-$N_1$-3')-$Sp_1$-(5'-$N_2$-3')-$Sp_2$-(5'-$N_3$-3'). In some embodiments, $N_1$ has the sequence 5'-TCGGCGC-3'. In some embodiments, $N_2$ has the sequence 5'-AACGTTC-3'. In some embodiments, $N_3$ has the sequence 5'-TCGGCGC-3'. In some embodiments, $N_1$ has the sequence 5'-TCGGCGC-3' and $N_2$ has the sequence 5'-AACGTTC-3'. In some embodiments, $N_1$ has the sequence 5'-TCGGCGC-3', $N_2$ has the sequence 5'-AACGTTC-3', and $N_3$ has the sequence 5'-TCGGCGC-3'. In some of these embodiments, the spacer moieties are hexaethylene glycol (HEG). In some embodiments, $Sp_1$ is hexaethylene glycol (HEG). In some embodiments, $Sp_2$ is hexaethylene glycol (HEG). In some embodiments, the linear chimeric compound of D contains less than 50 nucleotides (i.e., sum of $N_1$, $N_2$, and optionally $N_3$ is less than 50). In some embodiments, 5'-TCGGCGC-3' is located at the 5'-terminus of the linear chimeric compound (i.e., any additional nucleotides are added to the 3'-terminus). In some embodiments, each nucleic acid moiety N is less than 8 nucleotides in length, preferably 7 nucleotides in length. In some embodiments, each nucleic acid moiety N is from 4 to 7, preferably 5 to 7, or 6 or 7 nucleotides in length. The CpG dinucleotides of the nucleic acid moieties of the linear chimeric compound of D are unmethylated.

In some embodiments, D is linear chimeric compound comprising two nucleic acid moieties and a hexaethylene glycol spacer as 5'-TCGGCGC-3'-HEG-5'-AACGTTC-3' (SEQ ID NO:4), wherein the linear chimeric compound contains less than 50 nucleotides (i.e., sum of $N_1$ and $N_2$ is less than 50), and wherein one or more linkages between the nucleotides, between the nucleotides and the HEG, and between the 3'-terminal nucleotide and L$^1$ are phosphorothioate ester linkages. In some embodiments, D is a linear chimeric compound comprising three nucleic acid moieties and two hexaethylene glycol spacers as 5'-TCGGCGC-3'-HEG-5'-AACGTTC-3'-HEG-5'-TCGGCGC-3' (SEQ ID NO:2), wherein the linear chimeric compound contains less than 50 nucleotides (i.e., sum of $N_1$, $N_2$, and $N_3$ is less than 50), and wherein one or more linkages between the nucleotides and between the nucleotides and the HEG spacer are phosphorothioate ester linkages. In some embodiments, 5'-TCGGCGC-3'-HEG-5'-AACGTTC-3' (SEQ ID NO:4) or 5'-TCGGCGC-3'-HEG-5'-AACGTTC-3'-HEG-5'-TCG-GCGC-3' (SEQ ID NO:2) of D is located at the 5' terminus of the linear chimeric compound (i.e., any additional nucleotides are added to the 3'-terminus). In some embodiments, D is linear chimeric compound consisting of 5'-TCGGCGC-3'-HEG-5'-AACGTTC-3'-HEG-5'-TCGGCGC-3' (SEQ ID NO:2). In some embodiments, one or more linkages between the nucleotides are phosphodiester linkages. In some embodiments, all of the internucleotide linkages, the linkages between nucleotides and the HEG spacers, and the linkage between the 3'-terminal nucleotide and L$^1$ in the linear chimeric compound of D are phosphorothioate ester linkages. In some embodiments, the nucleic acid moieties of the linear chimeric compound of D are 2'-deoxyribopolynucleotides. The CpG dinucleotides of the nucleic acid moieties of the linear chimeric compound of D are unmethylated.

Polysaccharides derivatized to allow linking to nucleic acid moieties can be used as a multivalent carrier moiety serving as the branching unit for the branched chimeric compounds of the present disclosure. Suitable polysaccharides may be naturally occurring polysaccharides or synthetic polysaccharides. Exemplary polysaccharides include, e.g., dextran, mannin, chitosan, agarose, and starch. Mannin may be used, for example, because there are mannin (mannose) receptors on immunologically relevant cell types, such as monocytes and alveolar macrophages, and so the polysaccharide spacer moiety may be used for targeting particular cell types. In some embodiments, the polysaccharide is cross-linked. A preferred multivalent carrier moiety is epichlorohydrin-crosslinked sucrose (e.g., branched copolymer of sucrose and epichlorohydrin branded as FICOLL® by GE Healthcare).

In some embodiments F of formula (I) is a branched copolymer of sucrose and epichlorohydrin having a molecular weight of about 100,000 to about 700,000 daltons, which is connected to $L^3$ via an ether group. The ether group is derived from a sucrose hydroxyl of the copolymer. In some embodiments, F is a branched copolymer of sucrose and epichlorohydrin having a molecular weight greater than (lower limit) about 100,000, 200,000, 300,000, 400,000, 500,000 or 600,000 daltons. In some embodiments, F is a branched copolymer of sucrose and epichlorohydrin having a molecular weight less than (upper limit) about 700,000, 600,000, 500,000, 400,000, 300,000, or 200,000 daltons. That is the molecular weight of F can be any of a range of sizes from about 100,000 to about 700,000 daltons in which the lower limit is less than the upper limit. In some embodiments, F has a molecular weight of from about 300,00 to 500,00 daltons (e.g., FICOLL® PM 400 of GE Healthcare).

It is intended and understood that each and every variation of F detailed herein for the branched chimeric compound of formula (I) can be combined with each and every variation of D detailed herein for the branched chimeric compound of formula (I) as if each and every combination is individually described. For example, in some embodiments, provided is a branched chimeric compound of the formula (I):

$$[D-L^1-L^2-(PEG)-L^3]_x-F \quad (I),$$

wherein:
D is a polynucleotide or a linear chimeric compound;
$L^1$ is a first linker comprising an alkylthio group;
$L^2$ is a second linker comprising a succinimide group;
$L^3$ is a third linker comprising an amide group;
PEG is a polyethylene glycol (e.g., $-(OCH_2CH_2)_n-$, where n is an integer from 2 to 80);
x is an integer from 3 to 300; and
F is a branched copolymer of sucrose and epichlorohydrin having a molecular weight of about 100,000 to about 700,000 daltons and is connected to $L^3$ via an ether group, wherein the polynucleotide comprises the nucleotide sequence: 5'-TCGGCGC AACGTTC TCGGCGC-3' (SEQ ID NO:1), wherein the polynucleotide of D is less than 50 nucleotides in length, and wherein one or more linkages between the nucleotides are phosphorothioate ester linkages, and
wherein the linear chimeric compound of D comprises three nucleic acid moieties and two hexaethylene glycol (HEG) spacers as 5'-TCGGCGC-3'-HEG-5'-AACGTTC-3'-HEG-5'-TCGGCGC-3' (SEQ ID NO:2), wherein one or more linkages between the nucleotides, between the nucleotides and the HEG spacers and between the 3'-nucleotide and $L^1$ are phosphorothioate ester linkages.

The present disclosure provides a branched chimeric compound of formula (I) comprising a polynucleotide or a liner chimeric compound D linked to a multivalent moiety F via a polyethylene glycol (PEG) and various linkers $L^1$, $L^2$ and $L^3$ as: $-L^1-L^2-(PEG)-L^3-$, wherein $L^1$ is a first linker comprising an alkylthio group; $L^2$ is a second linker comprising a succinimide group; $L^3$ is a third linker comprising an amide group; and PEG is $-(OCH_2CH_2)_n-$.

Polyethylene glycol has found wide use in conjugating/modifying biologically active molecules because it is non-toxic, nonimmunogenic, hydrophilic, water soluble and highly flexible. The PEG containing moiety unit of the chimeric compounds of this disclosure provides better solubility and stability for these compounds compared to conjugates that employ hydrophobic moieties such as the methylcyclohexyl (MC) moieties commonly used in bioconjugation. The number of ethylene glycol units in the PEG linker can be tailored so as to optimize the length, hydrophilicity, and particle size of the branched chimeric compound.

In some embodiments, the PEG of formula (I) is of the formula $-(OCH_2CH_2)_n-$, where n is an integer from 2 to 80. In some embodiments, n is an integer greater than (lower limit) 2, 4, 6, 8, 10, 12, 14, 16, 18 or 20. In some embodiments, n is an integer less than (upper limit) 80, 70, 60, 50 or 40. That is, n can be an integer in the range of from about 2 to 80 in which the lower limit is less than the upper limit. In some embodiments, n is 2, 4, 6, 24, 45, 48 or 70. In some embodiments, n is 6, 24, 45 or 70. In some embodiments, n is 2, 4, 6, 24, 28, 45, 48 or 70. In some embodiments, n is 6, 24, 28, 45 or 70. In a preferred embodiment, PEG is $-(OCH_2CH_2)_6-$.

The PEG in the branched chimeric compounds of the present disclosure, is attached at one end to a 3'-nucleotide of the polynucleotide or the linear chimeric compound of D via linkers comprising a succinimide group and is attached at the other end to the multivalent moiety F via a linker comprising an amide group. An alkylthio group is employed to facilitate the chemical coupling between the 3'-nucleotide of the polynucleotide or the linear chimeric compound of D and the succinimide group. Thus, the first linker $L^1$ is a linker comprising an alkylthio group, which is capable of linking a 3'-terminal phosphate moiety of a nucleic acid to a succinimide group of the second linker $L^2$ by way of a terminal sulfhydryl group (—SH) of a precursor comprising L reacting with a maleimide group in a precursor comprising $L^2$ to form the a thiosuccinimdo linkage between $L^1$ and $L^2$. In some embodiments, $L^1$ is of the formula $-L^{1a}-S-$, where $L^{1a}$ is an alkylene group, for example, a group of formula $(CH_2)_m$ where m is an integer from 2 to 9. In some embodiments, $L^1$ is an alkylthio group of the formula $-(CH_2)_mS-$, where m is an integer from 2 to 9. In some of the embodiments, m is 2, 3, 4, 5, 6, 7, 8 or 9. In some embodiments, m is from 3 to 6. In some embodiments, m is 3 or 6. In a preferred embodiment, m is 6. In another preferred embodiment, m is 3. In some embodiments, $L^1$ is $-(CH_2)_6S-$ or $-(CH_2)_3S-$.

The second linker $L^2$ is a linker comprising a succinimide group. In some embodiments, $L^2$ further comprises an alkyl spacer group (e.g., $-CH_2CH_2-$) and/or an alkyl amide spacer group (e.g., $-CH_2CH_2C(O)NH-$). In some embodiments, $L^2$ is

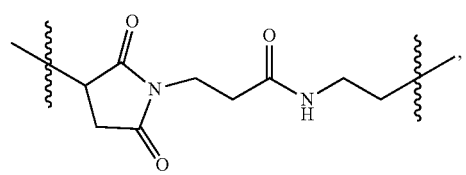

-continued

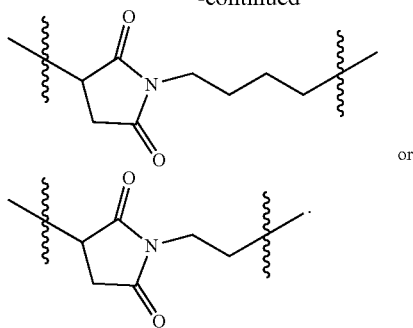

In some embodiments, L² is

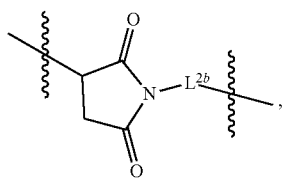

In some embodiments, L² is of the formula

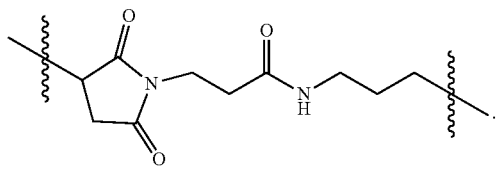

wherein L²ᵇ is an alkyl spacer group (e.g., —CH₂CH₂— or —CH₂CH₂CH₂CH₂—) and/or an alkyl amide spacer group (e.g., —CH₂CH₂C(O)NH—). In some embodiments, L²ᵇ is —CH₂CH₂C(O)NHCH₂CH₂—. In some embodiments, L²ᵇ is —CH₂CH₂C(O)NH CH₂CH₂CH₂—.

In some embodiments, the -L¹-L²- moiety is

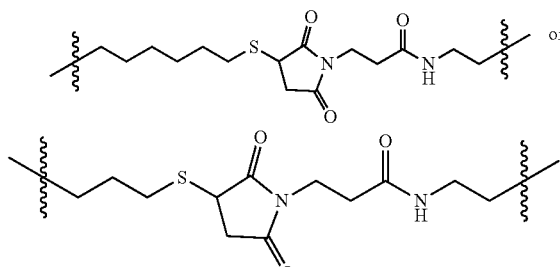

The third linker L³ is a linker comprising an amide group, which covalently links the PEG via an ether group to the multivalent moiety F. In some embodiments, L³ further comprises one or more alkyl spacer groups (e.g., —CH₂CH₂—), one or more amide spacer groups (e.g., —C(O)NH— or —NHC(O)—), or a combination thereof. In some embodiments, L³ is of the formula

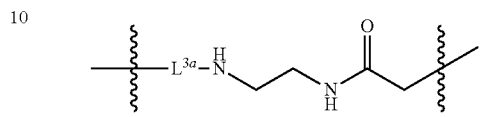

wherein L³ᵃ is a spacer capable of linking an alkyl group and an amine, such as a spacer of the formula —NHC(O)CH₂CH₂C(O)—, —OC(O)— or —C(O)—. The (2-aminoethyl)aminocarbonylmethyl moiety of L³ may be attached to F by reacting hydroxyl groups on F with chloroacetate and then coupling with ethylene diamine.

In some embodiments, L³ is

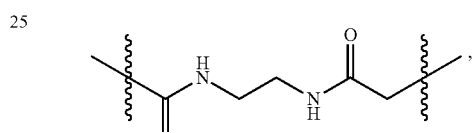

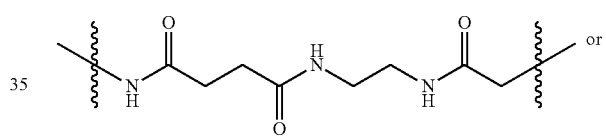

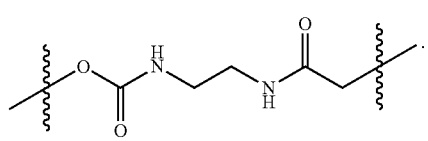

It is intended and understood that each and every variation of L¹, L², L³ and PEG detailed herein for the branched chimeric compound of formula (I) may be combined with each other, and may be combined further with each and every variation of D and F detailed herein for the branched chimeric compound of formula (I), as if each and every combination is individually described. For example, in some embodiments, the -L²-(PEG)-L³- moiety is of the formula (A), (B), (C), (D), (E), (F) or (G):

(A)

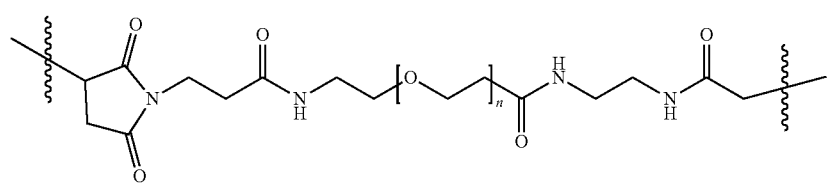

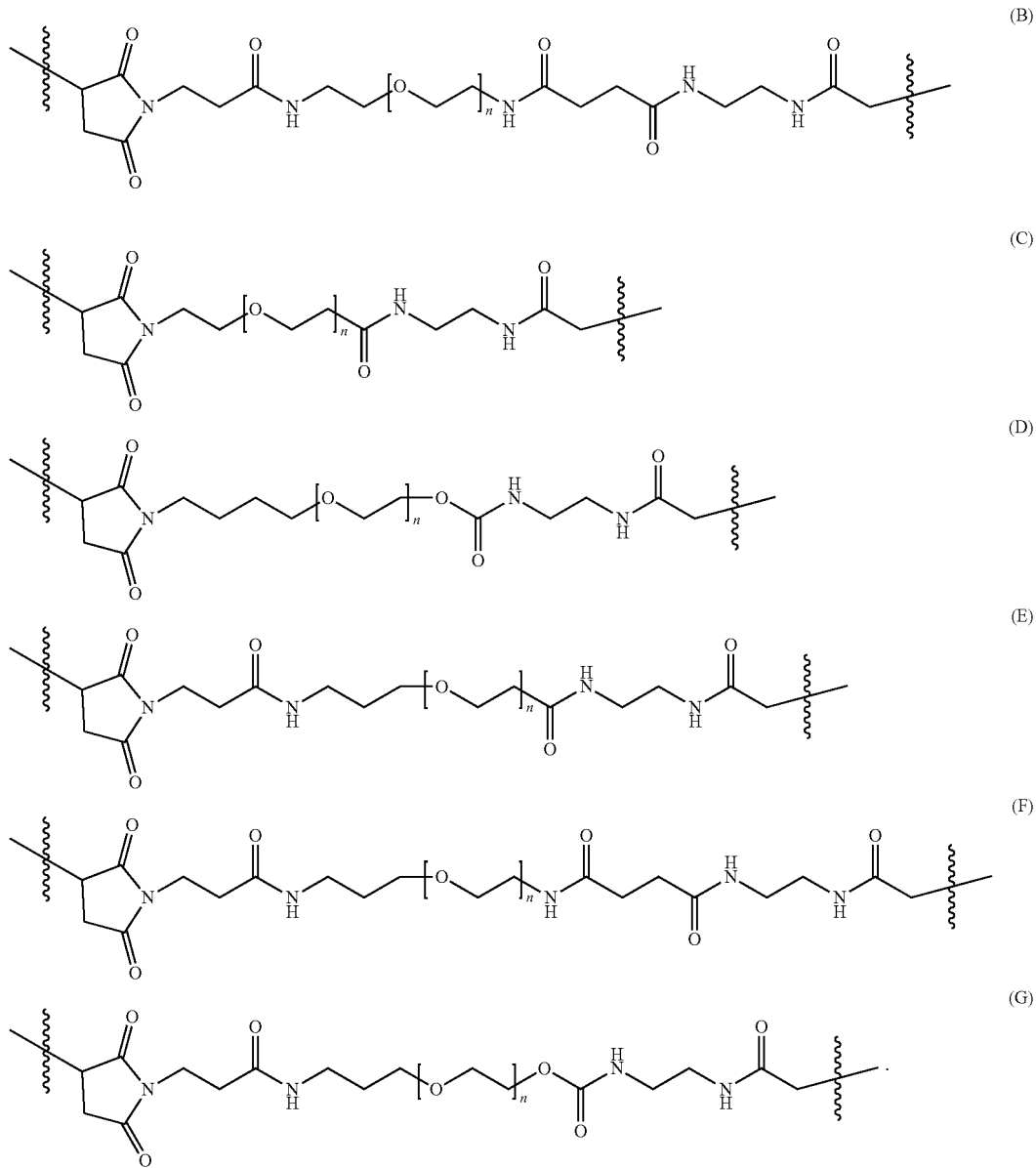
In some embodiments, the -L$^1$-L$^2$-(PEG)-L$^3$- moiety is
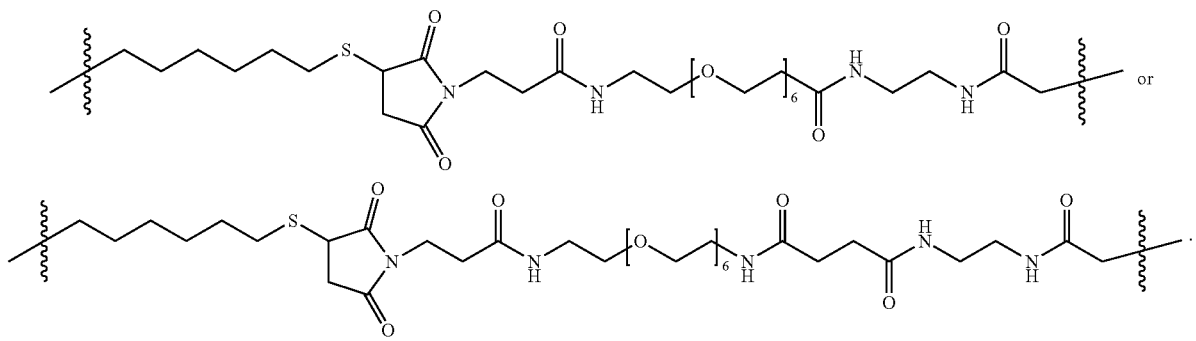

In some embodiments, the branched chimeric compound is of the formula

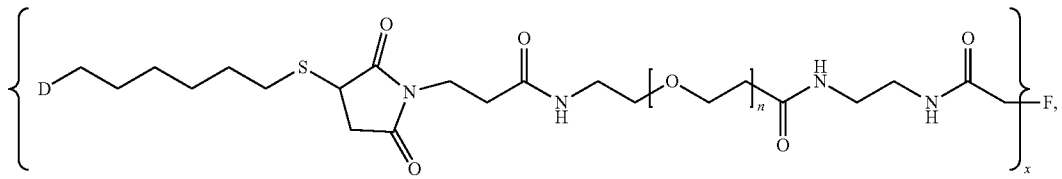

wherein D is linear chimeric compound consisting of 5'-TCGGCGC-3'-HEG-5'-AACGTTC-3'-HEG-5'-TCG-GCGC-3' (SEQ ID NO:2) wherein one or more linkages between the nucleotides, between the nucleotides and the HEG spacers and between the 3'-terminal nucleotide and $L^1$ are phosphorothioate ester linkages, F is a branched copolymer of sucrose and epichlorohydrin having a molecular weight of about 400,000, n is 6, 24, 45 or 70, and x is an integer from 3 to 300, wherein F is connected to the methylene group via an ether linkage. In some embodiments, n is 6 and x is from 90 to 150.

In some embodiments, the branched chimeric compound is of the formula

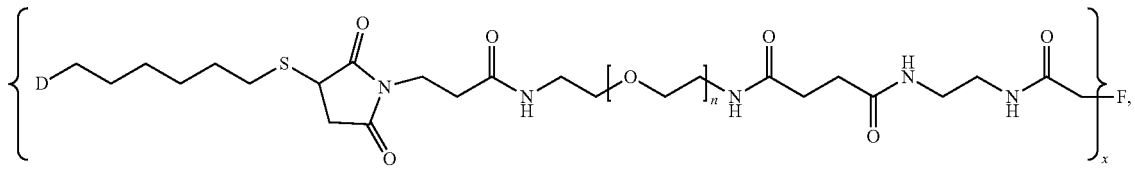

wherein D is linear chimeric compound consisting of 5'-TCGGCGC-3'-HEG-5'-AACGTTC-3'-HEG-5'-TCG-GCGC-3' (SEQ ID NO:2) wherein one or more linkages between the nucleotides, between the nucleotides and the HEG spacers and between the 3'-terminal nucleotide and $L^1$ are phosphorothioate ester linkages, F is a branched copolymer of sucrose and epichlorohydrin having a molecular weight of about 400,000, n is 6, 24, 45 or 70, and x is an integer from 3 to 300, wherein F is connected to the methylene group via an ether linkage. In some embodiments, n is 6 and x is from 90 to 150. In some embodiments, n is 45 and x is from 90 to 150.

The number of polynucleotides or linear chimeric compounds of D in the branched chimeric compound of formula (I) can range from 3 to about 300. That is, x is an integer from 3 to 300. In some embodiments, x is an integer greater than (lower limit) 3, 6, 9, 12, 20, 30, 40, 50, 60, 70, 80, 90, 100, 110, 120, 130, 140, 150, 155, 165, 190 or 200. In some embodiments, x is an integer less than (upper limit) 300, 275, 250, 225, 215, 210, 205, 200, 190, 180, 160, 150, 140, 130, 120, 110, 100, 90, 80, 70, 60 or 50. That x can be an integer in the range of from about 3 to 300 in which the lower limit is less than the upper limit. For instance in some embodiments, x is from 20 to 300, from 20 to 200, from 60 to 180, from 90 to 150, from 100 to 140, or from 110 to 130. In some embodiments, x is about 120±30. In a preferred embodiment, x is about 120.

Typical preparations of chimeric compounds of the disclosure are a heterogeneous mixture composed of chimeric compounds having a distribution of loading ratio with a specified average molecular weight or approximate number of D moieties per multivalent carrier moiety F, although reagents and reaction conditions may be controlled to achieve reproducibly desired loading ratio. In one aspect, a composition is provided comprising one or more branched chimeric compounds of formula (I) or variations thereof described herein. In some embodiments, the composition comprises a plurality of branched chimeric compounds of defined loading ratio and average molecular weight. In some embodiments, the composition comprises a heterogeneous mixture of compounds of formula (I), wherein D, PEG, $L^1$, $L^2$, $L^3$, F and x are independently as described herein for formula (I), wherein the F moieties of the chimeric compounds of the mixture have an average molecular weight between about 200,000 and about 600,000 Daltons, and wherein the chimeric compounds of the mixture have an average loading ratio (x) between about 60 and about 180.

In some embodiments, the composition comprises a heterogeneous mixture of compounds of formula (I), wherein D, PEG, $L^1$, $L^2$, $L^3$, F and x are independently as described herein for formula (I), wherein the F moieties of the chimeric compounds of the mixture having an average molecular weight between about 300,000 and about 500,000 (e.g., about 400,000) in Daltons. In some embodiments, the F moieties of the chimeric compounds of the mixture have a molecular weight between about 400,000±100,000 Daltons. In some embodiments, the composition comprises a heterogeneous mixture of compounds of formula (I), wherein D, PEG, $L^1$, $L^2$, $L^3$, F and x are independently as described herein for formula (I), wherein the chimeric compounds of the mixture having an average loading ratio (x) between about 90 and about 150 or between about 100 and about 140 (e.g., about 120). In some embodiments, the chimeric compounds of the mixture have a loading ratio (x) of about 120±30 or about 120±20). In some embodiments, the composition comprises a heterogeneous mixture of branched chimeric compounds of formula (I), wherein D, PEG, $L^1$, $L^2$, $L^3$, F and x are independently as described herein for formula (I), wherein the F moieties of the branched chimeric compounds of the mixture have a molecular weight of about 400,000±100,000 daltons, and wherein the branched chimeric compounds of the mixture have an average loading ratio of about 120±30).

The polynucleotides, linear chimeric compounds and branched chimeric compounds of the present disclosure have appreciable immunomodulatory activity (e.g., at least 3-fold higher than a non-immunomodulatory control). In some embodiments, the immunomodulatory activity comprises immunostimulatory activity. In other embodiments, the immunomodulatory activity comprises immunoinhibitory activity. The polynucleotides may be single stranded or double stranded. The polynucleotides may be RNA, DNA or a RNA/DNA hybrid. The internucleotide linkages, the linkages between nucleotides and the HEG spacers, and the linkage between the 3'-terminal nucleotide and the linker $L^1$ may be phosphate or thiophosphate esters.

In some embodiments, the polynucleotides, linear chimeric compounds and branched chimeric compounds of the present disclosure possess immunostimulatory activity. In these embodiments, D comprises SEQ ID NO:1, SEQ ID NO:2, SEQ ID NO:3 or SEQ ID NO:4. In some embodiments, D comprises one of the group consisting of SEQ ID NOS:9-16. The CpG dinucleotides of the polynucleotides or nucleic acid moieties of D are unmethylated. In some embodiments, 5'-TCG-3' of the polynucleotides or nucleic acid moieties of D are located at the 5'-terminus (e.g., any additional nucleotides are added to the 3'-terminus). In preferred embodiments, the polynucleotide does not comprise a Toll-like receptor (TLR) inhibitory motif. In preferred embodiments, the polynucleotides do not comprise TLR7, TLR8 and/or TLR9 inhibitory motifs. Exemplary TLR7 inhibitory motifs include 5'-$Q_zTGC$-3', 5'-$Q_zUGC$-3', 5'-$Q_zTIC$-3', and 5'-$Q_zTTC$-3', wherein Q is a nucleotide or nucleotide analog, and z' is 0, 1 or 2. That is $Q_{z'}$ is at the 5'-end of the polynucleotide. An exemplary TLR8 inhibitory motif is 5'-$X_1X_2X_3$-$M_{y'}$-3', wherein $X_1$ is A, T or C, $X_2$ is G or I, $X_3$ is I or A, M is a nucleotide or nucleotide analog, and y' is 0 or 1. That is $M_{y'}$ is at the 3'-end of the polynucleotide. An exemplary TLR9 inhibitory motif is 5'-$S_1S_2S_3S_4$-3', wherein each of $S_1$, $S_2$, $S_3$, and $S_4$ are independently G or I (inosine or 2'-deoxyinosine). In some embodiments in which the TLR9 inhibitory motif is 5'-$S_1S_2S_3S_4$-3', each of $S_1$, $S_2$, $S_3$, and $S_4$ are independently G or a molecule that is capable of preventing G-tetrad formation and/or preventing Hoogsteen base pairing such as inosine, 7-deaza-guanosine, 7-deaza-2'-deoxyxanthosine, 7-deaza-8-aza-2'-deoxyguanosine, 2'-deoxynebularine, isodeoxyguanosine, and 8-oxo-2'-deoxyguanosine.

Assays for assessing immunostimulatory activity are known in the art, and described in Examples B1 and B2. For the purpose of the present disclosure, immunostimulatory activity can be determined by measuring interferon-alpha production by human peripheral blood mononuclear cells after incubation in the present and absence of a test compound. A test compound is said to possess immunostimulatory activity when at least two-fold more interferon-alpha is produced in the presence of the test compound. It is understood that positive and negative controls are useful in assays for immunostimulatory activity. A suitable negative control for immunostimulatory activity is a medium alone. Another suitable negative control is a polynucleotide consisting of the nucleotide sequence 5'-TGACTGTGAA CCTTAGAGAT GA-3' (D56-30 set forth as SEQ ID NO:5). A suitable positive control for immunostimulatory activity is a polynucleotide consisting of the nucleotide sequence 5'-TGACTGTGAA CGTTCGAGAT GA-3' (D56-10 set forth as SEQ ID NO:6).

II. Synthesis of Chimeric Compounds

The disclosure further provides methods for preparing the chimeric compounds (such as the branched chimeric compounds) detailed herein, as well as compositions and intermediates useful therein.

In one aspect, the disclosure provides a method for making a branched chimeric compound of formula (I):

[D-$L^1$-$L^2$-(PEG)-$L^3$]$_x$-F    (I), wherein:

D is a polynucleotide or a linear chimeric compound;

$L^1$ is a first linker comprising an alkylthio group;

$L^2$ is a second linker comprising a succinimide group;

$L^3$ is a third linker comprising an amide group;

PEG is a polyethylene glycol (e.g., —(OCH$_2$CH$_2$)$_n$—, where n is an integer from 2 to 80);

x is an integer from 3 to 300; and

F is a branched copolymer of sucrose and epichlorohydrin having a molecular weight of about 100,000 to about 700,000 daltons and is connected to $L^3$ via an ether group, wherein the polynucleotide comprises the nucleotide sequence: 5'-TCGGCGC AACGTTC TCGGCGC-3' (SEQ ID NO:1), wherein the polynucleotide is less than 50 nucleotides in length, and wherein one or more linkages between the nucleotides and the linkage between the 3'-terminal nucleotide and $L^1$ are phosphorothioate ester linkages, and wherein the linear chimeric compound comprises three polynucleotides and two hexaethylene glycol (HEG) spacers as 5'-TCGGCGC-3'-HEG-5'-AACGTTC-3'-HEG-5'-TCGGCGC-3' (SEQ ID NO:2), wherein one or more of the linkages between the nucleotides, the linkages between the nucleotides and the HEG spacers and the linkage between the 3'-terminal nucleotide and $L^1$ are phosphorothioate ester linkages, wherein the method comprises:

reacting a compound of the formula D-$L^{1a}$-SH, where D is as defined for formula (I) and $L^{1a}$ is (CH$_2$)$_m$ where m is an integer from 2 to 9, with a compound of formula (II):

[$L^{2a}$-(PEG)-$L^3$]$_y$-F    (II)

wherein $L^3$, PEG and F are as defined for formula (I); $L^{2a}$ is

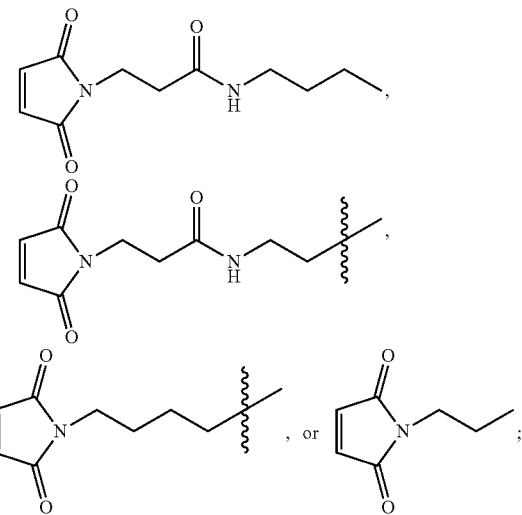

and y is an integer from 3 to 350.

In some embodiments, $L^{2a}$ is

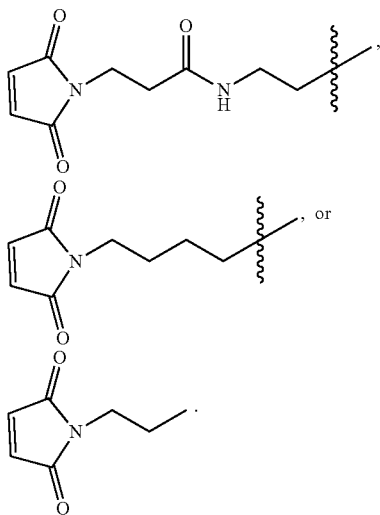

In some instances, every maleimide group in the compound of formula (II) is reacted with a nucleic acid moiety D. Thus in some embodiments, y equals to x. In other instances, only some of the maleimide groups in the compound of formula (II) are reacted with a nucleic acid moiety D, while some are not reacted with a nucleic acid moiety D. Thus in some embodiments, y is an integer greater than x. In some embodiments, y is an integer greater than (lower limit) 3, 6, 9, 12, 20, 30, 40, 50, 60, 70, 80, 90, 100, 110, 120, 130, 140, 150, 155, 165, 190 or 200. In some embodiments, y is an integer less than (upper limit) 350, 300, 275, 250, 225, 215, 210, 205, 200, 190, 180, 160, 150, 140, 130, 120, 110, 100, 90, 80, 70, 60 or 50. That y can be an integer in the range of from about 3 to 350 in which the lower limit is less than the upper limit. For example, in some embodiments, y is from 20 to 350, from 30 to 300, from 155 to 215, from 165 to 205, from 20 to 250, from 90 to 250, from 120 to 250, from 120 to 220, from 160 to 220, from 20 to 200, from 60 to 180, from 90 to 150, from 100 to 140, or from 110 to 130. In a preferred embodiment, y is about 190, about 185, about 150 or about 120. In some embodiments, y is about 190±30 or about 185±30. In some embodiments when y is an integer greater than x, the maleimide groups that are not reacted with a nucleic acid moiety D are capped and/or hydrolyzed. In some embodiments when y is an integer greater than x, the maleimide groups that are not reacted with a nucleic acid moiety D are capped with cysteine and/or are hydrolyzed by water.

The reactive thiol compound $D-L^{1a}-SH$ is often made from a more stable disulfide compound prior to use. In some embodiment, the method further comprises reacting a disulfide compound of the formula $D-L^{1a}-SS-L^{1a}-OH$ with a reducing agent (e.g., a phosphine compound). In some embodiments, D is as defined herein for formula (I) and $L^{1a}$ is $(CH_2)_m$ where m is an integer from 2 to 9. In some of the embodiments, m is 2, 3, 4, 5, 6, 7, 8 or 9. In some embodiments, m is from 3 to 6. In some of these embodiments, m is 3 or 6. In one embodiment, m is 6. In one embodiment, m is 3. One example of the reducing agent is tris(2-carboxyethyl)phosphine hydrochloride (TCEP).

The present invention also provides a compound of the formula $D-L^{1a}-SH$ or a compound of the formula $D-L^{1a}-SS-L^{1a}-OH$, wherein D is a polynucleotide or a linear chimeric compound, such as a polynucleotide detailed herein or a linear chimeric compound detailed herein, and $L^{1a}$ is $(CH_2)_m$ where m is an integer from 2 to 9. In some of these embodiments, D is a polynucleotide comprising the nucleotide sequence: 5'-TCGGCGC AACGTTC TCG-GCGC-3' (SEQ ID NO:1), wherein the polynucleotide of D is less than 50 nucleotides in length, and wherein one or more linkages between the nucleotides are phosphorothioate ester linkages. In some of these embodiments, D is a linear chimeric compound comprises three nucleic acid moieties and two hexaethylene glycol (HEG) spacers as 5'-TCG-GCGC-3'-HEG-5'-AACGTTC-3'-HEG-5'-TCGGCGC-3' (SEQ ID NO:2), wherein the linear chimeric compound contains less than 50 nucleotides, and wherein one or more linkages between the nucleotides, between the nucleotides and the HEG spacers and between the 3'-nucleotide and $L^1$ are phosphorothioate ester linkages. In some of these embodiments, D is a linear chimeric compound consisting of 5'-TCGGCGC-3'-HEG-5'-AACGTTC-3'-HEG-5'-TCG-GCGC-3' (SEQ ID NO:2). In some embodiments, all of the internucleotide linkages, the linkages between nucleotides and the HEG spacers, and the linkage between the 3'-terminal nucleotide and $L^1$ in the linear chimeric compound of D are phosphorothioate ester linkages. In some embodiments, the nucleic acid moieties of the linear chimeric compound of D are a 2'-deoxyribonucleotide. In some of the embodiments, m is 2, 3, 4, 5, 6, 7, 8 or 9. In some embodiments, m is from 3 to 6. In some of these embodiments, m is 3 or 6. In one embodiment, m is 6. In one embodiment, m is 3.

In some embodiments, $D-L^{1a}-SH$ is 5'-TCGGCGC-3'-HEG-5'-AACGTTC-3'-HEG-5'-TCGGCGC-3'-$(CH_2)_m$—SH (SEQ ID NO:2), where m is an integer from 2 to 9. In some embodiments, $D-L^{1a}-SS-L^{1a}-OH$ is 5'-TCGGCGC-3'-HEG-5'-AACGTTC-3'-HEG-5'-TCGGCGC-3'-$(CH_2)_m$—SS—$(CH_2)_m$—OH (SEQ ID NO:2), where m is an integer from 2 to 9. In some of these embodiments, m is 3 or 6. In one embodiment, m is 6. In one embodiment, m is 3.

The polynucleotides, linear chimeric compounds and disulfide modified nucleic acids described herein may be prepared using methods known in the art, such as methods descried in U.S. Pat. No. 8,114,418. For example, the polynucleotides can be manufactured by solid phase synthesis using phosphoramidite chemistry with oxidative sulfurization, purified and isolated according to the manufacturer's protocols (Molecules 2013, 18, 14268-14284). Examples of nucleoside monomers used were 5'-dimethoxytrityl-protected-2'-deoxynucleoside. The linear chimeric compounds are made by incorporating the HEG spacer (e.g., Space Phorphoramidite 18 from Glen Research, Sterling, Va.) in the polynucleotide. In some embodiments, the polynucleotides and/or the linear chimeric compounds are synthesized on a solid phase synthesizer programmed to add the nucleotide monomers, HEG spacers and linkers in the desired order, with the synthesis occurring in the 3' to 5' direction. The 3'-nucleoside or linker group (e.g., 3'-Thiol-Modifier C6 S-S CPG) is attached to the solid support. In some embodiments, the synthesis cycle consists of a detritylation step using acid (e.g., dichloroacetic acid in toluene), a coupling step using the phosphoramidite monomer plus a mildly acidic activator (e.g., saccharin 1-methylimidazole), an oxidative sulfurization step (e.g., 0.2 M Xanthane Hydride in pyridine), and a capping step for unreacted groups (e.g., isobutyric anhydride and N-methylimidazole). The synthesis cycle is repeated until the PN and CC sequence was fully assembled. The protected polynucleotide and chimeric compound can be cleaved and deprotected from the solid support (e.g., removal of cyanoethyl phosphate protecting groups using 20% t-butylamine in acetonitrile, followed by treatment with concentrated aqueous ammonia to cleave PN or CC from support, and holding the resulting solution for 72 hours at ambient temperature to remove the protecting groups on the nucleotides). The polynucleotides can be purified (e.g., using anion exchange chromatography), desalted (e.g., by ultrafiltration/diafiltration using a tangential flow filtration system), lyophilized, and stored frozen as lyophilized solids.

The PEG in the compound of the formula (II) can be introduced via an amine derivative of the multivalent polysaccharide F reacting with an activated ester compound comprising the PEG. In some embodiments, the method of making a compound of formula (I) further comprises reacting a compound of the formula (III):

wherein F is as defined for formula (I) and z is an integer from 3 to 400, with a compound of the formula $L^{2a}$-(PEG)-$L^{3a}$-Lv, where $L^{2a}$ and PEG are as defined for formula (II); $L^{3a}$ is —NHC(O)CH$_2$CH$_2$C(O)— or —C(O)—; and Lv is a leaving group, to form the compound of the formula (II).

In some embodiments, the activated ester compound comprising the PEG is an N-hydroxysuccinimide (NHS or HOSu) ester, and Lv is (2,5-dioxopyrrolidin-1-yl)oxy (i.e., OSu). Other activated carboxylic acid or esters known in the art can be used to react with the amine of formula (III) to form the compound of the formula (II).

In some embodiments, F is a branched copolymer of sucrose and epichlorohydrin having a molecular weight of about 100,000 to 700,000 in Daltons. In some embodiments, F is a branched copolymer of sucrose and epichlorohydrin having a molecular weight of about 400,000±100,000 Daltons (e.g., a FICOLL® PM 400), and the compound of formula (III) is a compound of AECM-FICOLL®400. Depending on the relative amounts of the activated ester $L^{2a}$-(PEG)-$L^{3a}$-Lv (e.g., an NHS ester $L^{2a}$-(PEG)-$L^{3a}$-OSu) to the compound of formula (III) (e.g., a compound of AECM-FICOLL®400) used, some or all of the amino groups in the compound of formula (III) may be PEGylated. Thus in some embodiments, z equals to y. In some embodiments, z is an integer greater than y. In some embodiments, z is an integer greater than (lower limit) 3, 6, 9, 12, 20, 30, 40, 50, 60, 70, 80, 90, 100, 110, 120, 130, 140, 150, 155, 165, 190 or 200. In some embodiments, z is an integer less than (upper limit) 400, 350, 300, 275, 250, 225, 215, 210, 205, 200, 190, 180, 160, 150, 140, 130, 120, 110, 100, 90, 80, 70, 60 or 50. That z can be an integer in the range of from about 3 to 400 in which the lower limit is less than the upper limit. For example, in some embodiments, z is from 20 to 400, from 50 to 300, from 190 to 250, from 200 to 240, from 20 to 350, from 30 to 300, from 155 to 215, from 165 to 205, from 20 to 250, from 90 to 250, from 120 to 250, from 120 to 220, from 160 to 220, from 20 to 200, from 60 to 180, from 90 to 150, from 100 to 140, or from 110 to 130. In a preferred embodiment, z is about 220, about 190, about 150 or about 120. In some embodiments, z is about 220±30 or about 220±20. In some embodiments when z is an integer greater than y, excess amines are capped. In some embodiments when z is an integer greater than y, excess amines are capped with sulfo-NHS-acetate or NHS-acetate.

FICOLL® is synthesized by cross-linking sucrose with epichlorohydrin which results in a highly branched structure. Aminoethylcarboxymethyl-FICOLL (AECM-FICOLL®) can be prepared by the method of Inman, 1975, *J. Imm.* 114:704-709. AECM-FICOLL can then be reacted with a heterobifunctional crosslinking reagent, such as 6-maleimido caproic acyl N-hydroxysuccinimide ester, and then conjugated to a thiol-derivatized nucleic acid moiety (see Lee et al., 1980, *Mol. Imm.* 17:749-56). Other polysaccharides may be modified similarly.

The NHS ester ($L^{2a}$-(PEG)-$L^{3a}$-OSu) used in the method may be obtained from commercial sources or made by methods known in the art.

In some embodiments, provided is a compound of formula (II):

wherein:
$L^{2a}$ is a moiety comprising a maleimide group;
$L^3$ is a linker comprising an amide group;
PEG is a polyethylene glycol;
y is an integer from 3 to 350; and
F is a branched copolymer of sucrose and epichlorohydrin and is connected to $L^3$ via an ether group.

In some embodiments of the compounds of formula (II), $L^3$, PEG and F are as defined for formula (I) or any variations detailed herein; $L^{2a}$ is

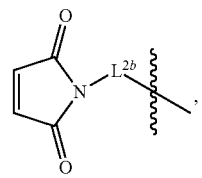

wherein $L^{2b}$ is as detailed herein for formula (I) or any variations thereof (e.g., —CH$_2$CH$_2$C(O)NHCH$_2$CH$_2$CH$_2$—, —CH$_2$CH$_2$C(O)NHCH$_2$CH$_2$—, —CH$_2$CH$_2$— or —CH$_2$CH$_2$CH$_2$CH$_2$—); and
y is as detailed herein for formula (II).

For example, in some embodiments of the compounds of formula (II), F has a molecular weight of from about 300,000 to 500,000 daltons (e.g., FICOLL® PM 400 of GE Healthcare). In some embodiments, y is an integer greater than (lower limit) 3, 6, 9, 12, 20, 30, 40, 50, 60, 70, 80, 90, 100, 110, 120, 130, 140 or 150. In some embodiments, y is an integer greater than (lower limit) 3, 6, 9, 12, 20, 30, 40, 50, 60, 70, 80, 90, 100, 110, 120, 130, 140, 150, 155, 165, 190 or 200. In some embodiments, y is an integer less than (upper limit) 350, 300, 275, 250, 225, 215, 210, 205, 200, 190, 180, 160, 150, 140, 130, 120, 110, 100, 90, 80, 70, 60 or 50. That y can be an integer in the range of from about 3 to 350 in which the lower limit is less than the upper limit. For example, in some embodiments, y is from 20 to 350, from 30 to 300, from 155 to 215, from 165 to 205, from 20 to 250, from 90 to 250, from 120 to 250, from 120 to 220, from 160 to 220, from 20 to 200, from 60 to 180, from 90 to 150, from 100 to 140, or from 110 to 130. In a preferred embodiment, y is about 190, about 185, about 150 or about 120. In some embodiments, y is about 190±30 or about 185±30. In some embodiments, PEG is of the formula —(OCH$_2$CH$_2$)$_n$—, where n is an integer from 2 to 80. In a preferred embodiment, PEG is —(OCH$_2$CH$_2$)$_6$—. In some embodiments, $L^{2a}$ is

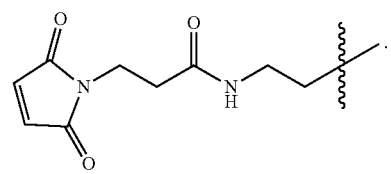 [SMILES: *CCNC(=O)CCN1C(=O)C=CC1=O]

In some embodiments, $L^3$ is of the formula

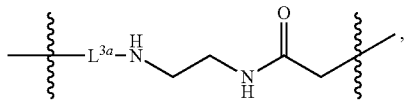

wherein $L^{3a}$ is a spacer capable of linking an alkyl group and an amine, such as a spacer of the formula —NHC(O)CH$_2$CH$_2$C(O)— or —C(O)—.

In some embodiments, provided is a method for making a compound of formula (II):

[L$^{2a}$-(PEG)-L$^3$]$_y$-F    (II)

wherein:
$L^{2a}$ is a moiety comprising a maleimide group;
$L^3$ is a linker comprising an amide group;
PEG is a polyethylene glycol (e.g., —(OCH$_2$CH$_2$)$_n$—, where n is an integer from 2 to 80);
y is an integer from 3 to 350; and
F is a branched copolymer of sucrose and epichlorohydrin and is connected to $L^3$ via an ether group,
the method comprising reacting a compound of the formula (III):

[NH$_2$CH$_2$CH$_2$NHC(O)CH$_2$]$_z$—F    (III)

wherein F is as defined for formula (II) and z is an integer from 3 to 400,
with a compound of the formula L$^{2a}$-(PEG)-L$^{3a}$-Lv, where L$^{2a}$ and PEG are as defined for formula (II); L$^{3a}$ is —NHC(O)CH$_2$CH$_2$C(O)—, —OC(O)— or —C(O)—; and Lv is a leaving group (e.g., (2,5-dioxopyrrolidin-1-yl)oxy).

In some embodiments, provided is composition comprising a heterogeneous mixture of compounds of formula (II), wherein L$^{2a}$, PEG, L$^3$, F and y are independently as described herein for formula (II), wherein the F moieties of the heterogeneous mixture of compounds of formula (II) have an average molecular weight between about 200,000 and about 600,000 in Daltons, and wherein the compounds of formula (II) in the heterogeneous mixture have an average loading ratio (y) between about 60 and about 250. In some embodiments, the F moieties of the heterogeneous mixture of compounds of formula (II) have an average molecular weight between about 300,000 and about 500,000 in Daltons. In some embodiments, the F moieties of the heterogeneous mixture of compounds of formula (II) have an average molecular weight of about 400,000±100,000 Daltons. In some embodiments, the compounds of formula (II) in the heterogeneous mixture have an average loading ratio (y) between about 60 and about 250, between about 90 and about 250, between about 120 and about 250, between about 120 and about 220, between about 160 and about 220, between about 60 and about 200, between about 60 and about 180, or between about 90 and about 150. In some embodiments, the compounds of formula (II) in the heterogeneous mixture have an average loading ratio (y) of about 120±30, about 150±30, about 185±30 or about 190±30. In some embodiments, the composition comprises a heterogeneous mixture of compounds of formula (II), wherein L$^{2a}$, PEG, L$^3$, F and y are independently as described herein for formula (II), wherein the F moieties of the heterogeneous mixture of compounds of formula (II) have an average molecular weight of about 400,000±100,000 Daltons, and wherein the compounds of formula (II) in the heterogeneous mixture have an average loading ratio (y) of about 120±30, about 150±30, about 185±30 or about 190±30.

The present invention also provides a method for making a mixture comprising a distribution of compounds of formula (I) detailed herein from a distribution of compounds of formula (II) detailed herein. In one aspect, provided is a method for making a heterogeneous mixture of branched chimeric compounds of formula (I):

[D-L$^1$-L$^2$-(PEG)-L$^3$]$_x$-F    (I)

wherein:
D is independently a polynucleotide or a linear chimeric compound;
$L^1$ is independently a first linker comprising an alkylthio group;
$L^2$ is independently a second linker comprising a succinimide group;
$L^3$ is independently a third linker comprising an amide group;
PEG is independently a polyethylene glycol (e.g., —(OCH$_2$CH$_2$)$_n$—, where n is an integer from 2 to 80);
x is independently an integer from 3 to 300; and
F is independently a branched copolymer of sucrose and epichlorohydrin having a molecular weight of about 100,000 to about 700,000 and is connected to $L^3$ via an ether group,
wherein the polynucleotide comprises the nucleotide sequence: 5'-TCGGCGC AACGTTC TCGGCGC-3' (SEQ ID NO:1), wherein the polynucleotide is independently less than 50 nucleotides in length, and wherein one or more linkages between the nucleotides and the linkage between the 3'-terminal nucleotide and $L^1$ are phosphorothioate ester linkages, and
wherein the linear chimeric compound independently comprises three polynucleotides and two hexaethylene glycol (HEG) spacers as 5'-TCGGCGC-3'-HEG-5'-AACGTTC-3'-HEG-5'-TCGGCGC-3' (SEQ ID NO:2), wherein one or more of the linkages between the nucleotides, the linkages between the nucleotides and the HEG spacers and the linkage between the 3'-terminal nucleotide and $L^1$ are phosphorothioate ester linkages,
the method comprises:
reacting a composition comprising compounds of the formula D-L$^{1a}$-SH, where D is independently as defined for formula (I) and L$^{1a}$ is (CH$_2$)$_m$ where m is independently an integer from 2 to 9, with a composition comprising a heterogeneous mixture of compounds of formula (II):

[L$^{2a}$-(PEG)-L$^3$]$_y$-F    (II)

wherein L$^3$, PEG and F are independently as defined for formula (I);
each L$^{2a}$ is independently

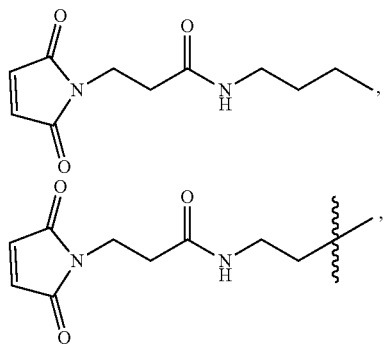

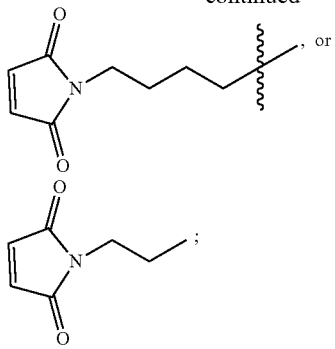

and y is independently an integer from 3 to 350;

and wherein the composition comprising compounds of formula (II) comprises a heterogeneous mixture of compounds of formula (II), wherein the F moieties of the heterogeneous mixture of compounds of formula (II) have an average molecular weight between about 200,000 and about 600,000 in Daltons, and wherein the compounds of formula (II) in the mixture have an average loading ratio (y) between about 60 and about 250. In some embodiments, the F moieties of the heterogeneous mixture of compounds of formula (II) have an average molecular weight of about 400,000±100,000 Daltons. In some embodiments, the compounds of formula (II) in the heterogeneous mixture have an average loading ratio (y) of about 120±30, about 150±30, about 185±30 or about 190±30.

In some embodiments, each $L^{2a}$ is independently

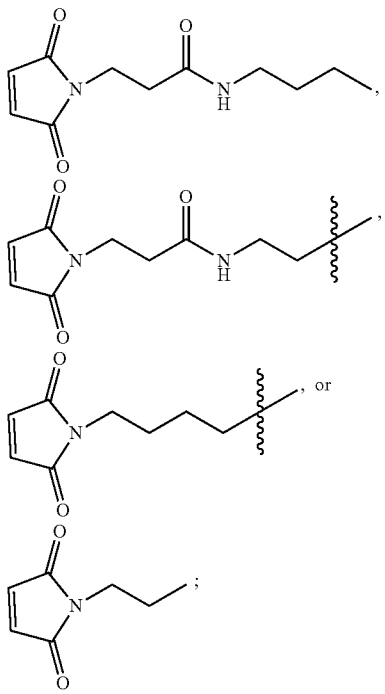

In some embodiments, provided is a method for making a composition comprising a heterogeneous mixture of compounds of formula (II):

$$[L^{2a}\text{-(PEG)-}L^3]_y\text{-F} \qquad (II)$$

wherein:

$L^{2a}$ is independently a moiety comprising a maleimide group;

$L^3$ is independently a linker comprising an amide group;

PEG is independently a polyethylene glycol (e.g., —(OCH$_2$CH$_2$)$_n$—, where n is an integer from 2 to 80);

y is independently an integer from 3 to 350; and

F is independently a branched copolymer of sucrose and epichlorohydrin and is connected to $L^3$ via an ether group, comprising reacting a composition comprising a mixture of compounds of the formula (III):

$$[\text{NH}_2\text{CH}_2\text{CH}_2\text{NHC(O)CH}_2]_z\text{—F} \qquad (III)$$

wherein F is as defined for formula (II) and z is independently an integer from 3 to 400, with a compound of the formula $L^{2a}$-(PEG)-$L^{3a}$-Lv, where $L^{2a}$ and PEG are as defined for formula (II); $L^{3a}$ is —NHC(O)CH$_2$CH$_2$C(O)—, —OC(O)— or —C(O)—; and Lv is a leaving group (e.g., (2,5-dioxopyrrolidin-1-yl)oxy), and wherein the F moieties of the mixture of compounds of formula (III) have an average molecular weight between about 200,000 and about 600,000 daltons, and the mixture of compounds of the formula (III) have an average loading ratio (z) between about 60 and about 280.

In some embodiments of the method for making a composition comprising a heterogeneous mixture of compounds of formula (II), $L^{2a}$, PEG, $L^{3a}$ and Lv are as detailed herein, and wherein the F moieties of the mixture of compounds of formula (III) have an average molecular weight between about 300,000 and about 500,000 in Daltons. In some embodiments, the F moieties of the mixture of compounds of formula (III) have an average molecular weight of about 400,000±100,000 Daltons. In some embodiments, the mixture of compounds of the formula (III) have an average loading ratio (z) between about 50 and about 350, between about 50 and about 280, between about 60 and about 250, between about 60 and about 180, between about 60 and about 150, between about 90 and about 280, between about 90 and about 250, between about 90 and about 200, between about 90 and about 150, between about 120 and about 280, between about 120 and about 250, between about 150 and about 280, between about 150 and about 250, between about 180 and about 280, between about 180 and about 250, between about 200 and about 250 or between about 210 and about 230. In some embodiments, the mixture of compounds of the formula (III) have an average loading ratio (z) of about 120±30, about 150±30, about 180±30, about 220±30 or about 220±20. In some embodiments, the mixture of compounds of formula (III) is AECM FICOLL® 400.

In some embodiments, the method for making a heterogeneous mixture of branched chimeric compounds of formula (I) further comprises reacting a composition comprising a mixture of compounds of the formula (III) as detailed herein with a compound of the formula $L^{2a}$-(PEG)-$L^{3a}$-Lv as detailed herein.

In some embodiments, the methods of making a compound of formula (I) or a composition comprising a heterogeneous mixture of compounds of formula (I) further comprise purifying the chimeric compounds of formula (I), and/or any of the intermediate compounds such as compounds of formula (II) and compounds of formula (III). In some embodiments, the method further comprises purifying the chimeric compounds of formula (I) by diafiltration. In some embodiments, the method further comprises purifying the chimeric compounds of formula (I) by diafiltration using a 100,000 molecular weight cut off (MWCO) membrane.

III. Pharmaceutical Compositions

Pharmaceutical compositions comprising a polynucleotide, linear chimeric compound or branched chimeric compound (e.g., active agent) of the present disclosure are also provided. The pharmaceutical compositions routinely contain a pharmaceutically acceptable excipient. In some embodiments, the pharmaceutical compositions further comprise an antigen. Pharmaceutical compositions of the present disclosure may be in the form of a solution or a freeze dried solid. The pharmaceutical compositions of the present disclosure are preferably sterile, and preferably essentially endotoxin-free.

A. Excipients

Pharmaceutically acceptable excipients of the present disclosure include for instance, solvents, bulking agents, buffering agents, tonicity adjusting agents, and preservatives (see, e.g., Pramanick et al., Pharma Times, 45:65-77, 2013). In some embodiments the pharmaceutical compositions may comprise an excipient that functions as one or more of a solvent, a bulking agent, a buffering agent, and a tonicity adjusting agent (e.g., sodium chloride in saline may serve as both an aqueous vehicle and a tonicity adjusting agent). The pharmaceutical compositions of the present disclosure are suitable for parenteral administration. That is the pharmaceutical compositions of the present disclosure are not intended for enteral administration.

In some embodiments, the pharmaceutical compositions comprise an aqueous vehicle as a solvent. Suitable vehicles include for instance sterile water, saline solution, phosphate buffered saline, and Ringer's solution. In some embodiments, the composition is isotonic or hypertonic.

The pharmaceutical compositions may comprise a bulking agent. Bulking agents are particularly useful when the pharmaceutical composition is to be lyophilized before administration. In some embodiments, the bulking agent is a lyoprotectant that aids in the stabilization and prevention of degradation of the active agents during freeze-drying and/or during storage. Suitable bulking agents are sugars (mono-, di- and polysaccharides) such as sucrose, lactose, trehalose, mannitol, sorbital, glucose and raffinose.

The pharmaceutical compositions may comprise a buffering agent. Buffering agents control pH to inhibit degradation of the active agent during processing, storage and optionally reconstitution. Suitable buffers include for instance salts comprising acetate, citrate, phosphate or sulfate. Other suitable buffers include for instance amino acids such as arginine, glycine, histidine, and lysine. The buffering agent may further comprise hydrochloric acid or sodium hydroxide. In some embodiments, the buffering agent maintains the pH of the composition within a range of 4 to 9. In some embodiments, the pH is greater than (lower limit) 4, 5, 6, 7 or 8. In some embodiments, the pH is less than (upper limit) 9, 8, 7, 6 or 5. That is, the pH is in the range of from about 4.0 to 9.0 in which the lower limit is less than the upper limit.

The pharmaceutical compositions may comprise a tonicity adjusting agent. Suitable tonicity adjusting agents include for instance dextrose, glycerol, sodium chloride, glycerin and mannitol.

The pharmaceutical compositions may comprise a preservative. Suitable preservatives include for instance antioxidants and antimicrobial agents. However, in preferred embodiments, the pharmaceutical composition is prepared under sterile conditions and is in a single use container, and thus does not necessitate inclusion of a preservative.

B. Antigens

The present disclosure further provides pharmaceutical compositions comprising an antigen and an excipient in addition to a polynucleotide, linear chimeric compound or branched chimeric compound. In the compositions of the present disclosure comprising an antigen, the antigen is not covalently-linked to the polynucleotide, the linear chimeric compound or the branched chimeric compound. In some preferred embodiments, the antigen is a protein antigen. In some preferred embodiments, the antigen is a polysaccharide antigen, which is preferably covalently attached to a carrier protein. In some embodiments, the antigen is a microbial antigen, an allergen or a tumor antigen.

The pharmaceutical compositions may comprise a microbial antigen selected from the group consisting of a viral antigen, a bacterial antigen, a fungal antigen and a parasite antigen. In some embodiments, the microbial antigen is from a microbe that causes an infectious disease in a nonhuman, mammalian subject. In some embodiments, the microbial antigen is from a microbe that causes an infectious disease in a human subject. In some embodiments, the infectious disease is caused by a virus, a bacterium, a fungus or a protozoan parasite. Suitable microbial antigens include for instance antigens of adenovirus type 4, adenovirus type 7, anthrax, *Mycobacterium tuberculosis*, *Corynebacterium diphtheriae* (e.g., diphtheria toxoid), *Clostridium tetani* (e.g., tetanus toxoid), *Bordetella pertussis*, *Haemophilus influenzae* type B, hepatitis A virus, hepatitis B virus (e.g., HBsAg), human papillomavirus (types 6, 11, 16, 18, 31, 33, 45, 52 and 58) influenza virus type A and B (e.g., haemagglutinin, neuraminadase), influenza virus type B, parainfluenza virus, Japanese encephalitis virus, measles virus, mumps virus, rubella virus, *Neisseria menigitidis* (Groups A, B, C, Y and W-135), *Streptococcus pneumoniae* (serotypes 1, 3, 4, 5, 6A, 6B, 7F, 9V, 14, 18C, 19A, 19F and 23F), poliovirus, rabies virus, rotavirus, vaccinia virus, *Salmonella typhi*, varicella zoster virus, and yellow fever virus (see, e.g., "www.fda.gov/BiologicsBloodVaccines/Vaccines"). In some embodiments, the microbial antigen is a viral antigen of Herpes simplex virus type 1 or 2, human herpes virus, human immunodeficiency virus type 1, and respiratory syncytial virus. In some embodiments, the microbial antigen is a fungal antigen of *Candida albicans*, *Aspergillus flavus*, *Cryptococcus neoformans*, *Histoplasma capsulatum*, and *Pneumocystis carinii*. In some embodiments, the microbial antigen is a parasite antigen of a *Leishmania* species, a *Plasmodium* species, a *Schistosoma* species. or a *Trypanosoma* species.

The pharmaceutical compositions may comprise an allergen. In some embodiments, the allergen is an environmental antigen such as mammalian, insect, plant and mold allergens. In some embodiments, the mammalian allergen includes fur and dander. Suitable mammalian allergens include for instance, cat Fel d 1, cow Bos d 2, dog Can f I and Can f II, horse Equ c1, and mouse MUP. In some embodiments, the insect allergen includes insect feces and venom. Exemplary insect allergens include ant Sol i2, bee PLA and Hya, cockroach Bla g Bd9OK, Bla g4, GST, and Per a3, dust mite Der p2, Der f2, Der p10, and Tyr p2, hornet Dol m V, mosquito Aed a 1, and yellow jacket hyaluronidase and phospholipase. In some embodiments, the plant allergen includes grass, weed and tree allergens (e.g., pollens). Suitable grass allergens include for instance, allergens of Kentucky bluegrass, meadow fescue, orchard grass, redtop grass, perennial ryegrass, sweet vernal grass and timothy. Exemplary plant allergens include barley Hor v 9, birch Bet v1 and v2, cherry Pru a 1, corn Zml3, grass Phl p 1, 2, 4, 5, 6, 7, 11 and 12, Hol l 5, Cyn d 7 and d12, cedar Jun a 2, Cry j 1 and j2, juniper Jun o2, latex Hev b7, yellow mustard Sin a I, rapeseed Bra r 1, ragweed Amb a 1, and rye Lol p1. In some embodiments, the mold allergen is an *Aspergillus fumigatus* allergen such as Asp f 1, 2, 3, 4 and 6. In some embodiments the allergen is a food allergen such as a shell fish allergen, a legume allergen, a nut allergen or a milk allergen. Exemplary food allergens include shrimp tropomyosin, peanut Ara h 1, 2, 3, 8 and 9, walnut Jug r 1 and 3, hazelnut Cor a 1, 14 and 8 LTP, cow's milk lactalbumin, casein and lactoferrin.

The pharmaceutical compositions may comprise a tumor antigen. In some embodiments, the tumor antigen is a mammalian antigen. Suitable tumor antigens have been described in the art (see, e.g., Cheever et al., Clinical Cancer Research, 15:5323-5337, 2009). For instance, suitable tumor antigens include WT1, MUC1, LMP2, HPV E6 E7, EGFRvIII, Her-2/neu, idiotype, MAGE A3, p53, NY-ESO-1, PSMA, GD2, CEA, MelanA/Mart1, Ras, gp100, proteinase3 (PR1), bcr-able, tyrosinase, survivin, PSA, hTERT, sarcoma translocation breakpoints, EphA2, PAP, MP-IAP, AFP, EpCAM, ERG, NA17, PAX3, ALK, androgen receptor, cyclin B1, polysialic acid, MYCN, PhoC, TRP-2, GD3, Fucosyl, GM1, mesothelin, PSCA, MAGE A1, sLe(a), CYP1B1, PLAC1, GM3, BORIS, Tn, GloboH, ETV6-AML, NY-BR-1, RGS5, SART3, STn, cabonic anhydrase IX, PAX5, OY-TES1, sperm protein 17, LCK, HMWMAA, AKAP-4, SSX2, XAGE 1, B7H3, legumain, Tie 2, Page4, VEGFR2, MAD-CT-1, FAP, PDGFR-beta, MAD-CT-2, and Fos-related antigen 1.

IV. Methods of Use

The pharmaceutical compositions of the present disclosure are suitable for a plurality of uses involving modulating an immune response in a mammalian subject in need thereof. Mammalian subjects include but are not limited to humans, nonhuman primates, rodents, pets, and farm animals. In some embodiments, modulating an immune response comprises stimulating an immune response. In some embodiments, modulating an immune response comprises inhibiting an immune response. In some embodiments, the pharmaceutical compositions may be administered to the subject in an amount effective to achieve a specific outcome.

A. Dosage and Mode of Administration

As with all pharmaceutical compositions, the effective amount and mode of administration may vary based on several factors evident to one skilled in the art. Factors to be considered include whether the pharmaceutical composition contains a polynucleotide, a linear chimeric compound or a branched chimeric compound (e.g., active agents), and whether the pharmaceutical composition further contains an antigen. In general, dosages of multivalent active agents such as branched chimeric compounds are lower than dosages of monovalent active agents such as polynucleotides and linear chimeric compounds. Other factors to be considered include the outcome to be achieved, and the number of doses to be administered.

A suitable dosage range is one that provides the desired effect. Dosage may be determined by the amount of polynucleotide, linear chimeric compound or branched chimeric compound administered to the subject. An exemplary dosage range of the polynucleotide, linear chimeric compound or branched chimeric compound given in amount to be delivered by subject weight is from about 1 to 1000 mcg/kg. In some embodiments, the dosage is greater than about (lower limit) 1, 5, 10, 50, 100, 150, 200, 250, 300, 350, 400, 450 or 500 mcg/kg. In some embodiments, the dosage is less than about (upper limit) 1000, 900, 800, 700, 600, 500, 450, 400, 350, 300, 250, 200, 150, or 100 mcg/kg. That is, the dosage is anywhere in the range of from about 1 to 1000 mcg/kg in which the lower limit is less than the upper limit. An exemplary dosage range of the polynucleotide, linear chimeric compound or branched chimeric compound given in amount to be delivered to a subject is from about 100 to 5000 mcg. In some embodiments, the dosage is greater than about (lower limit) 100, 500, 1000, 1500, 2000, 2500, 3000, 3500 or 4000 mcg. In some embodiments, the dosage is less than about (upper limit) 5000, 4500, 4000, 3500, 3000, 2500, 2000, 1500, or 1000 mcg. That is, the dosage is anywhere in the range of from about 100 to 5000 mcg in which the lower limit is less than the upper limit.

In some embodiments, when the pharmaceutical composition further comprises an antigen, the antigen dosage range given in amount to be delivered to a subject is from about 1 mcg to 50 mcg. In some embodiments, the antigen dosage is greater than about (lower limit) 1, 5, 10, 15, 20, 25, 30, 35 or 40 mcg. In some embodiments, the antigen dosage is less than about (upper limit) 50, 45, 40, 35, 30, 25, 20, 15, or 10 mcg. That is, the antigen dosage is anywhere in the range of from about 1 to 50 mcg in which the lower limit is less than the upper limit.

Likewise, a suitable route of administration is one that provides the desired effect. In general, the pharmaceutical compositions of the present disclosure are intended for parenteral administration (e.g., not oral or rectal administration). Suitable routes of administration include injection, topical and inhalation. In particular, the pharmaceutical compositions of the present disclosure may be administered by a route such as intramuscular, subcutaneous, intravenous epidermal (gene gun), transdermal, and inhalation. Devices suitable for administration by inhalation include, for instance atomizers, vaporizers, nebulizers, and dry powder inhalation delivery devices. In some embodiments, when the pharmaceutical compositions are intended to treat a solid tumor, the compositions are administered intratumorally.

A suitable dosing regimen is one that provides the desired effect in a prophylactic or therapeutic context. The number of doses administered by a chosen route may be one or more than one. Frequency of dosing may range from weekly, bi-weekly, monthly, bi-monthly, or 3 to 12 months between doses. In some embodiments, 2 doses are administered with the second dose being administered one to two months after the first dose. In some embodiments, 3 doses are administered with the second dose being administered one to two months after the first dose, and the third dose being administered one to five months after the second dose. In other embodiments, 3, or 4 doses may be administered on a bi-weekly or monthly basis. In other embodiments, a shorter or longer period of time may elapse in between doses. In certain embodiments, the interval between successive dosages may vary in terms of number of weeks or number of months. In one embodiment, a series of 2, 3, 4, 5, or 6 weekly doses may be administered followed by a second series of a number of weekly doses at a later time point. One of skill in the art will be able to adjust the dosage regiment by measuring biological outcomes as exemplified in the Examples, such as antigen-specific antibody responses or tumor regression.

B. Stimulation of an Immune Response

The pharmaceutical compositions of the present disclosure are suitable for a plurality of uses involving modulating an immune response in a mammalian subject in need thereof. In some embodiments, the mammalian subject is a human patient. In some embodiments, the pharmaceutical compositions are used to stimulate an immune response in a mammalian subject. In some embodiments, the pharmaceutical compositions are used to inhibit an immune response in a mammalian subject. In some embodiments, the pharmaceutical compositions are administered to the subject so as to achieve a specific outcome.

In brief, the present disclosure provides methods of stimulating an immune response in a mammalian subject, comprising administering to a mammalian subject a pharmaceutical composition in an amount sufficient to stimulate an immune response in the mammalian subject. "Stimulating" an immune response, means increasing the immune response, which can arise from eliciting a de novo immune response (e.g., as a consequence of an initial vaccination regimen) or enhancing an existing immune response (e.g., as a consequence of a booster vaccination regimen). In some embodiments, stimulating an immune response comprises one or more of the group consisting of: stimulating IFN-alpha production; stimulating IL-6 production; stimulating B lymphocyte proliferation; stimulating interferon pathway-associated gene expression; stimulating chemoattractant-associated gene expression; and stimulating plasmacytoid dendritic cell (pDC) maturation. Methods for measuring stimulation of an immune response are known in the art and described in the biological examples of the present disclosure. In embodiments in which the pharmaceutical composition further comprises an antigen, stimulating an immune response comprises inducing an antigen-specific antibody response.

For instance, in some embodiments in which the pharmaceutical composition further comprises an antigen, the present disclosure provides methods of inducing an antigen-specific antibody response in a mammalian subject by administering to a mammalian subject the pharmaceutical composition in an amount sufficient to induce an antigen-specific antibody response in the mammalian subject. "Inducing" an antigen-specific antibody response means increasing titer of the antigen-specific antibodies above a threshold level such as a pre-administration baseline titer or a seroprotective level.

The present disclosure further provides methods of preventing an infectious disease in a mammalian subject, comprising administering to a mammalian subject a pharmaceutical composition in an amount sufficient to prevent an infectious disease in the mammalian subject. That is, in some embodiments, the present disclosure provides prophylactic vaccines. In some embodiments, the mammalian subject is at risk of exposure to an infectious agent. "Preventing" an infectious disease means to protect a subject from developing an infectious disease. In some embodiments, preventing an infectious disease further comprises protecting a subject from being infected with an infectious agent (e.g., protecting a subject from developing an acute or a chronic infection). Additionally the present disclosure provides methods of ameliorating a symptom of an infectious disease in a mammalian subject, comprising administering to a mammalian subject a pharmaceutical composition in an amount sufficient to ameliorate a symptom of an infectious disease in the mammalian subject. That is, in some embodiments the present disclosure provides therapeutic vaccines. In some embodiments, the subject is acutely or chronically infected with an infectious agent. The infectious disease may be a viral, bacterial, fungal or parasitic disease. In some embodiments, the pharmaceutical composition may further comprise a viral, bacterial, fungal or parasitic antigen. "Ameliorating" a symptom of an infectious disease means to improve a symptom, preferably diminishing extent of the disease.

Moreover the present disclosure provides methods of ameliorating a symptom of an IgE-related disorder in a mammalian subject, comprising administering to the mammalian subject a pharmaceutical composition in an amount sufficient to ameliorate a symptom of an IgE-related disorder in the mammalian subject. In some preferred embodiments, the IgE-related disorder is an allergy. Allergies include but are not limited to allergic rhinitis (hay fever), sinusitis, eczema, and hives. In some embodiments, the pharmaceutical composition may further comprise an allergen. "Ameliorating" a symptom of an IgE-related disorder means to improve a symptom, preferably diminishing extent of the disorder. For instance, if the IgE-related disorder is allergic rhinitis, ameliorating a symptom means to reduce swelling of nasal mucosa, reduce rhinorrhea (runny nose), and/or reduce sneezing.

Furthermore, the present disclosure provides methods of treating cancer in a mammalian subject, comprising administering to a mammalian subject a pharmaceutical composition in an amount sufficient to treat cancer in the mammalian subject. "Treating" cancer means to bring about a beneficial clinical result such as causing remission or otherwise prolonging survival as compared to expected survival in the absence of treatment. In some embodiments, when the cancer is a solid tumor, "treating" cancer comprises shrinking the size of the solid tumor or otherwise reducing viable cancer cell numbers. In other embodiments, when the cancer is a solid tumor, "treating" cancer comprises delaying growth of the solid tumor.

Analysis (both qualitative and quantitative) of the immune response can be by any method known in the art, including, but not limited to, measuring antigen-specific antibody production (including measuring specific antibody subclasses), activation of specific populations of lymphocytes such as B cells and helper T cells, production of cytokines such as IFN-alpha, IL-6, IL-12 and/or release of histamine. Methods for measuring antigen-specific antibody responses include enzyme-linked immunosorbent assay (ELISA). Activation of specific populations of lymphocytes can be measured by proliferation assays, and with fluorescence-activated cell sorting (FACS). Production of cytokines can also be measured by ELISA.

Preferably, a Th1-type immune response is stimulated (i.e., elicited or enhanced). With reference to present disclosure, stimulating a Th1-type immune response can be determined in vitro or ex vivo by measuring cytokine production from cells treated with an active agent of the present disclosure (polynucleotide, linear chimeric compound or branched chimeric compound) as compared to control cells not treated with the active agent. Examples of "Th1-type cytokines" include, but are not limited to, IL-2, IL-12, IFN-gamma and IFN-alpha. In contrast, "Th2-type cytokines" include, but are not limited to, IL-4, IL-5, and IL-13. Cells useful for the determination of immunostimulatory activity include cells of the immune system, such as antigen presenting cells lymphocytes, preferably macrophages and T cells. Suitable immune cells include primary cells such as peripheral blood mononuclear cells, including plasmacytoid dendritic cells and B cells, or splenocytes isolated from a mammalian subject.

Stimulating a Th1-type immune response can also be determined in a mammalian subject treated with an active agent of the present disclosure (polynucleotide, linear chimeric compound or branched chimeric compound) by measuring levels of IL-2, IL-12, and interferon before and after administration or as compared to a control subject not treated with the active agent. Stimulating a Th1-type immune response can also be determined by measuring the ratio of Th1-type to Th2-type antibody titers. "Th1-type" antibodies include human IgG1 and IgG3, and murine IgG2a. In contrast, "Th2-type" antibodies include human IgG2, IgG4 and IgE and murine IgG1 and IgE.

In some embodiments, the present disclosure provides kits that comprise a pharmaceutical composition (comprising an excipient and a polynucleotide, a linear chimeric compound or a branched chimeric compound) and a set of instructions relating to the use of the composition for the methods describe herein. The pharmaceutical composition of the kits is packaged appropriately. For example, if the pharmaceutical composition is a freeze-dried power, a vial with a resilient stopper is normally used so that the powder may be easily resuspended by injecting fluid through the resilient stopper. In some embodiments, the kits further comprise a device for administration (e.g., syringe and needle) of the pharmaceutical composition. The instructions relating to the use of the pharmaceutical composition generally include information as to dosage, schedule and route of administration for the intended methods of use. In some embodiments, in which the kits comprise an antigen, the antigen may or may not be packaged in the same container as the polynucleotide, linear chimeric compound or branched chimeric compound.

EXAMPLES

Abbreviations

BCC (branched chimeric compound); CC (chimeric compound); HEG (hexaethylene glycol); LCC (linear chimeric compound); MWCO (molecular weight cut-off); PEG (polyethylene glycol); PN (polynucleotide); Sp (spacer); TFF (tangential flow filtration).

Although, the present disclosure has been described in some detail by way of illustration and example for purposes of clarity and understanding, it will be apparent to those skilled in the art that certain changes and modifications may be practiced. Therefore, the following synthetic and biological examples should not be construed as limiting the scope of the present disclosure, which is delineated by the appended claims.

Synthetic Examples

Example S1: Structure of Polynucleotides and Chimeric Compounds

Table S1-1 shows the structures of polynucleotides (PN) and chimeric compounds (CC) referred to in the Examples. The nucleotides in the polynucleotides and chimeric compounds are 2'-deoxyribopolynucleotides. HEG is a hexaethylene glycol spacer moiety. Other spacers are described in the specification and figures. Except where noted in Table S1-1 or in specific examples, all internucleotide linkages and linkages between nucleic acid moieties and spacer moieties are phosphorothioate ester linkages. Table S1-1 also shows CCs (e.g., D56-02, D56-03, D56-07, D56-08, D56-10, D56-11) with an end linking group (e.g., —(CH2)6-SS—(CH2)6-OH, —(CH2)6-SH, —(CH2)3SS—(CH2)3-OH, —(CH2)3SH, HO(CH2)6-SS—(CH2)6-, and HS(CH2)6-) used to link these molecules with a branched carrier moiety (e.g., [Maleimide-PEGn]y-FICOLL) to create branched CCs. These linking groups are connected to the polynucleotide or CC via a terminal nucleotide or spacer moiety with a phosphorothioate linkage. Branched CCs (e.g., [(D56-01)-PEGn]x-FICOLL) are prepared by conjugation strategies and have linking groups as described in the Examples.

TABLE S1-1

Polynucleotide (PN) and Chimeric Compound (CC) Structures^

| Cmpd. Number | Cmpd. Nickname | SEQ ID NO: | Structure |
|---|---|---|---|
| D56-01 | N/A | 2 | 5'-TCGGCGC-3'-HEG-5'-AACGTTC-3'-HEG-5'-TCGGCGC-3' |
| D56-02 | (D56-01)-3'-SS | 2 | 5'-TCGGCGC-3'-HEG-5'-AACGTTC-3'-HEG-5'-TCGGCGC-3'-$(CH_2)_6$-SS-$(CH_2)_6$-OH (see Example S2) |
| D56-03 | (D56-01) 3'-SH | 2 | 5'-TCGGCGC-3'-HEG-5'-AACGTTC-3'-HEG-5'-TCGGCGC-3'-$(CH_2)_6$-SH (see Example S3, Section F) |
| D56-04 | N/A | 1 | 5'-TCGGCGC AACGTTC TCGGCGC-3' |
| D56-05 | [(D56-01)-PEG$_6$]$_x$-FIC | 2 | [(5'-TCGGCGC-3'-HEG-5'-AACGTTC-3'-HEG-5'-TCGGCGC-3'-$(CH_2)_6$-S)-PEG$_6$-AECM]$_x$-FICOLL$_{400}$ (see Example S3 and S9) |
| D56-06 | N/A | NA | 5'-TCGACGT-3' |
| D56-07 | (D56-06)-3'-HEG-SS | NA | 5'-TCGACGT-3'-HEG-$(CH_2)_3$-SS-$(CH_2)_3$-OH (see Example S2) |
| D56-08 | (D56-06)-3'-HEG-SH | NA | 5'-TCGACGT-3'HEG-$(CH_2)_3$-SH (see Example S16) |
| D56-09 | [(D56-06)-HEG-MC]$_x$-FIC | NA | [(5'-TCGACGT-3'-HEG-$(CH_2)_3$-S)-MC-AECM]$_x$-FICOLL$_{400}$ (see Example S16) |
| D56-10 | 1018 ISS | 6 | 5'-TGACTGTGAA CGTTCGAGAT GA-3' |
| D56-11 | 5'-SS-(D56-10) | 6 | HO$(CH_2)_6$SS$(CH_2)_6$-5'-TGACTGTGAA CGTTCGAGAT GA-3' (see Example S2) |

TABLE S1-1-continued

Polynucleotide (PN) and Chimeric Compound (CC) Structures^

| Cmpd. Number | Cmpd. Nickname | SEQ ID NO: | Structure |
|---|---|---|---|
| D56-12 | 5'-HS-(D56-10) | 6 | HS(CH$_2$)$_6$-5'-TGACTGTGAA CGTTCGAGAT GA-3' (see Example S16) |
| D56-13 | [(D56-10)-MC]$_x$-FIC | 6 | FICOLL$_{400}$-[AECM-MC-S(CH$_2$)$_6$-5'-TGACTGTGAA CGTTCGAGAT GA-3')]$_x$ (see Example S16) |
| D56-14 | N/A | 7 | 5'-TCGTCGA-3'-HEG-5'-ACGTTCG-3'-HEG-5'-AGATGAT-3' |
| C56-15 | N/A | 8 | 5'-TCGACGT-3'-HEG-5'-TCGACGT-3'-HEG-5'-AACGTTC-3' |
| D56-16 | N/A | 9 | 5'-TCGTTCG-3'-HEG-5'-TCGTTCG-3'-HEG-5'-AACGTTC-3' |
| D56-17 | N/A | 10 | 5'-TCGTTCG-3'-HEG-5'-AACGTTC-3'-HEG-5'-TCGTTCG-3' |
| D56-18 | N/A | 11 | 5'-TCGGCGC-3'-HEG-5'-TCGGCGC-3'-HEG-5'-AACGTTC-3' |
| D56-19 | N/A | 12 | 5'-TCGCCGG-3'-HEG-5'-TCGCCGG-3'-HEG-5'-AACGTTC-3' |
| D56-20 | N/A | 13 | 5'-TCGCCGG-3'-HEG-5'-AACGTTC-3'-HEG-5'-TCGCCGG-3' |
| D56-21 | N/A | 14 | 5'-TCGATCG-3'-HEG-5'-TCGATCG-3'-HEG-5'-AACGTTC-3' |
| D56-22 | N/A | 15 | 5'-TCGTCGT-3'-HEG-5'-TCGTCGT-3'-HEG-5'-AACGTTC-3' |
| D56-23 | N/A | 16 | 5'-TCGTCGT-3'-HEG-5'-AACGTTC-3'-HEG-5'-TCGTCGT-3' |
| D56-24 | N/A | 17 | 5'-TCGACGT-3'-HEG-5'-AACGTTC-3'-HEG-5'-TCGACGT-3' |
| D56-25 | [(D56-01)-PEG$_{24}$]$_x$-FIC | 2 | [(5'-TCGGCGC-3'-HEG-5'-AACGTTC-3'-HEG-5'-TCGGCGC-3'-(CH$_2$)$_6$-S)-PEG$_{24}$-AECM]$_x$-FICOLL$_{400}$ (see Example S13) |
| D56-26 | [(D56-01)-PEG$_{45}$]$_x$-FIC | 2 | [(5'-TCGGCGC-3'-HEG-5'-AACGTTC-3'-HEG-5'-TCGGCGC-3'-(CH$_2$)$_6$-S)-PEG$_{45}$-AECM]$_x$-FICOLL$_{400}$ (see Example S13) |
| D56-27 | [(D56-01)-PEG$_{70}$]$_x$-FIC | 2 | [(5'-TCGGCGC-3'-HEG-5'-AACGTTC-3'-HEG-5'-TCGGCGC-3'-(CH$_2$)$_6$-S)-PEG$_{70}$-AECM]$_x$-FICOLL$_{400}$ (see Example S13) |
| D56-28 | N/A | 3 | 5'-TCGGCGC AACGTTC-3' |
| D56-29 | N/A | 4 | 5'-TCGGCGC-3'-HEG-5'-AACGTTC-3' |
| D56-30 | Negative Control | 5 | 5'-TGACTGTGAA CCTTAGAGAT GA-3' |

^Compounds are given the same SEQ ID NO when the only difference from a compound with a defined SEQ ID NO is in non-nucleic acid moieties linked to the 3' nucleotide of D. Additionally, compounds having a nucleic acid moiety containing fewer than 10 nucleotides are not assigned a SEQ ID NO and are therefore designated as NA (not applicable) above. FICOLL is abbreviated as FIC.

Example S2: Synthesis of Polynucleotides (PN) and Chimeric Compounds (CC)

Polynucleotides were manufactured by solid phase synthesis using phosphoramidite chemistry with oxidative sulfurization, purified and isolated according to the manufacturer's protocols (Molecules 2013, 18, 14268-14284). The nucleoside monomers used were 5'-dimethoxytrityl-protected-2'-deoxynucleoside, 3'-((2-cyanoethyl)-(N,N-diisopropyl))-phosphoramidites. For the CCs, the HEG spacer was incorporated using 18-O-dimethoxytritylhexaethyleneglycol, 1-((2-cyanoethyl)-(N,N-isopropyl))-phosphoramidite (e.g., Space Phorphoramidite 18 from Glen Research, Sterling, Va.). For D56-11, the 5'-C6-disulfide linker was incorporated using 1-O-dimethoxytrityl-hexyl-disulfide-1'-((2-cyanoethyl)-(N,N-diisopropyl))-phosphoramidite (e.g., Thiol-Modifier C6 S-S from Glen Research, Sterling, Va.). For D56-07, the 3'-C3-disulfide linker was incorporated using 1-O-dimethoxytrityl-propyl-disulfide, 1'-succinyl-solid support (e.g., 3'-Thiol-Modifier C3 S-S CPG from Glen Research, Sterling, Va.). For D56-02, the 3'-C6-disulfide linker was incorporated using 1-O-dimethoxytrityl-hexyl-disulfide, 1'-succinyl-solid support (e.g., 3'-Thiol-Modifier C6 S-S CPG from Glen Research, Sterling, Va. or as a custom order from Prime Synthesis).

PN and CC were synthesized on a solid phase synthesizer programmed to add the nucleotide monomers, HEG spacers and linkers in the desired order, with the synthesis occurring in the 3' to 5' direction. The 3'-nucleoside or linker group (e.g., 3'-Thiol-Modifier C6 S-S CPG) was attached to the solid support. The synthesis cycle consisted of a detrytilation step using acid (e.g., dichloroacetic acid in toluene), a coupling step using the phosphoramidite monomer plus a mildly acidic activator (e.g., saccharin 1-methylimidazole), an oxidative sulfurization step (e.g., 0.2 M Xanthane Hydride in pyridine), and a capping step for unreacted groups (e.g., isobutyric anhydride and N-methylimidazole). The synthesis cycle was repeated until the PN and CC sequence was fully assembled. The protected PN and CC were cleaved and deprotected from the solid support (e.g., removal of cyanoethyl phosphate protecting groups using 20% t-butylamine in acetonitrile, followed by treatment with concentrated aqueous ammonia to cleave PN or CC from support, and holding the resulting solution for 72 hours at ambient temperature to remove the protecting groups on the nucleotides). The polynucleotides were purified using anion exchange chromatography, desalted by ultrafiltration/diafiltration using a tangential flow filtration (TFF) system and lyophilized. PN and CC are stored frozen as lyophilized solids.

D56-02 was manufactured at the 10 mmol scale. The appearance was a white powder, the found molecular weight was 7780 (theoretical 7785 Da), the purity by reverse phase HPLC was 85% and the purity by ion exchange HPLC was 86%.

Alexa Fluor® 555-(D56-01) (aka fluorescently labeled D56-01) was prepared by TriLink Biotechnologies (San Diego, Calif.). Alexa Fluor® brand fluorescent dyes are marketed by Molecular Probes, Inc. (Eugene, Oreg.).

Example S3: Manufacture of D56-05 (aka [(D56-01)-PEG$_6$]$_x$-FICOLL

The D56-05 (aka [(D56-01)-PEG$_6$]$_x$-FICOLL) manufacturing scheme is comprised of three stages, as shown in FIG. 1. Other PN or CC conjugates to FICOLL can be prepared by the same manufacturing route by changing the PN or CC sequence, the thiol linker to the PN or CC, and/or the thiol to amine crosslinker.

In Stage 1, FICOLL is modified in several steps to include a reactive maleimide group, resulting in [Maleimide-PEG$_6$]$_y$-FICOLL. In Stage 2, the disulfide in D56-02 (aka (D56-01)-3'-SS) is reduced to a thiol, forming D56-03 (aka (D56-01)-3'-SH). In Stage 3, [Maleimide-PEG$_6$]$_y$-FICOLL and D56-03 react to form D56-05 (aka [(D56-01)-PEG$_6$]$_x$-FICOLL). Purification occurs at each step in the process. The final D56-05 solution is sterile filtered and characterized. The D56-05 solution is stored at <-60° C.

Figure 2:
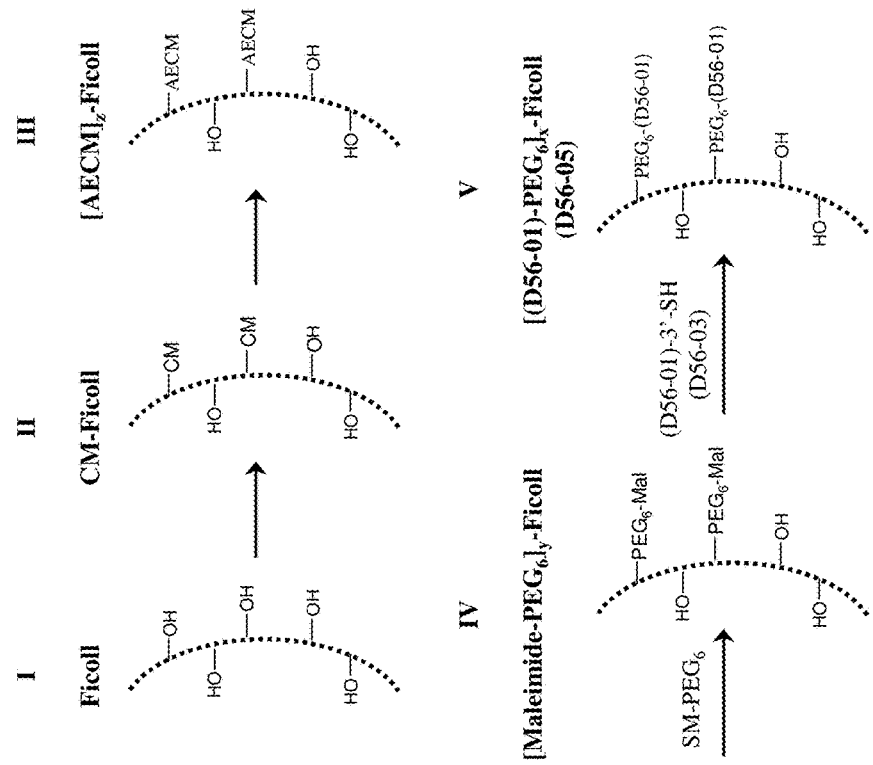
FIG. 2 illustrates preparation of an exemplary branched chimeric compound, D56-05, (aka [(D56-01)-$PEG_6$]$_x$-FICOLL).

FIG. 2 outlines the process for manufacture of the FICOLL intermediates carboxymethylated (CM)-FICOLL, aminoethylcarbamylmethylated [AECM]$_z$-FICOLL, and [Maleimide (Mal)-PEG$_6$]$_y$-FICOLL, and the final product D56-05, aka [(D56-01)-PEG$_6$]$_x$-FICOLL.

I. Composition of FICOLL PM400. FICOLL PM400 (FICOLL$_{400}$) is a synthetic neutral, highly-branched polymer of sucrose with a reported molecular weight of 400,000+/−100,000 that exists as a suspension of nanoparticles. It is formed by copolymerization of sucrose with epichlorohydrin. FICOLL PM400 was purchased as a spray dried powder from GE Healthcare (Pittsburgh, Pa.).

II. Stage 1, Step 1: Preparation of Carboxymethylated-FICOLL (CM-FICOLL)

CM-FICOLL was prepared from FICOLL PM400 by the method of Inman, *J. Immunology*, 1975, 114: 704-709) except that instead of using a standard desalting procedure (e.g., dialysis using a 5 kDa molecular weight cut-off (MWCO) membrane), a purification using tangential flow fractionation (TFF) with a 100 kDa MWCO membrane was performed. The TFF purification removed the small molecules and excess reagents similarly to the standard desalting procedure.

Figure 3:
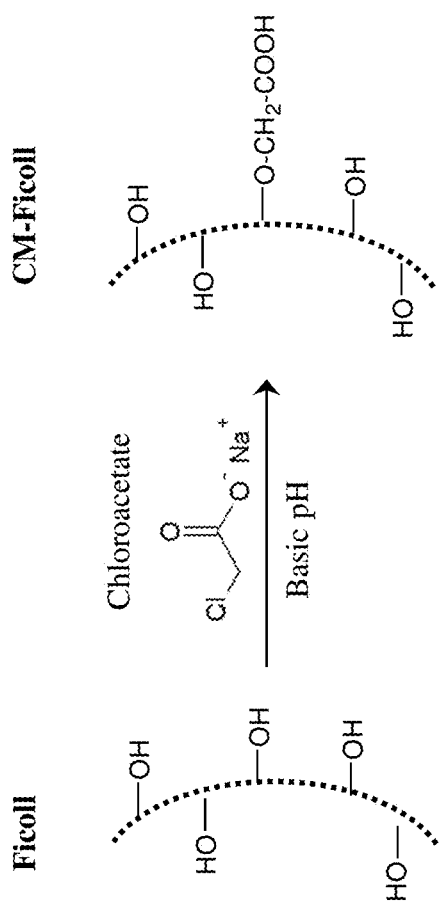
FIG. 3 shows the reaction scheme for the preparation of carboxymethylated-FICOLL.

CM-FICOLL is produced by reacting FICOLL PM400 with sodium chloroacetate under basic conditions. The reaction scheme is shown FIG. 3. A solution of FICOLL PM400 (13 g) was prepared at 130 mg/mL in Milli-Q deionized water. The solution was transferred to a jacketed reaction vessel connected to a 40° C. circulating water bath, for 40-45 min. To this FICOLL solution, 92.5 mL of 2.7 M sodium chloroacetate solution, 50 mL of 10 N sodium hydroxide solution, and 7.5 mL Milli-Q deionized water were added. The reaction proceeded for 2.5 hours at 40° C. while stirring. Then, the reaction solution was transferred to a chilled glass bottle and placed on ice. Immediately thereafter, 10 mL of 2 M sodium phosphate buffer pH 4 were added to the reaction solution, and the pH was adjusted to 7.0 by addition of 20% chloroacetic acid solution. The crude CM-FICOLL was kept at low temperature (on ice) until ready for purification. The crude CM-FICOLL was purified by diafiltration using a system setup with a tangential flow fractionation (TFF) membrane having a 100 kDa MWCO. The crude CM-FICOLL was diafiltered against 0.2 M aqueous sodium chloride for a total of approximately 15-18 volume exchanges. The absorbance of each permeate diavolume was measured at 215 nm and the diafiltration was stopped when the permeate absorbance reached 0.1 AU. The purified CM-FICOLL solution was concentrated to about 30 mg/mL and stored at −80° C. Three lots of CM-FICOLL were prepared by this process, each starting with 13 g of FICOLL PM400. The yields of CM-FICOLL were 6.7 g, 7.1 g and 7.7 g.

III. Stage 1, Step 2: Preparation of N-(2-aminoethyl)carbamylmethylated-FICOLL (aka [AECM]$_z$-FICOLL). [AECM]$_z$-FICOLL was prepared from CM-FICOLL by the method of Inman (J. Immunology, 1975, 114: 704-709) except that instead of using a standard desalting procedure (e.g., dialysis using a 5 kDa molecular weight cut-off (MWCO) membrane), a purification using tangential flow fractionation (TFF) with a 100 kDa MWCO membrane was performed (as described for CM-FICOLL in Section B).

Figure 4:
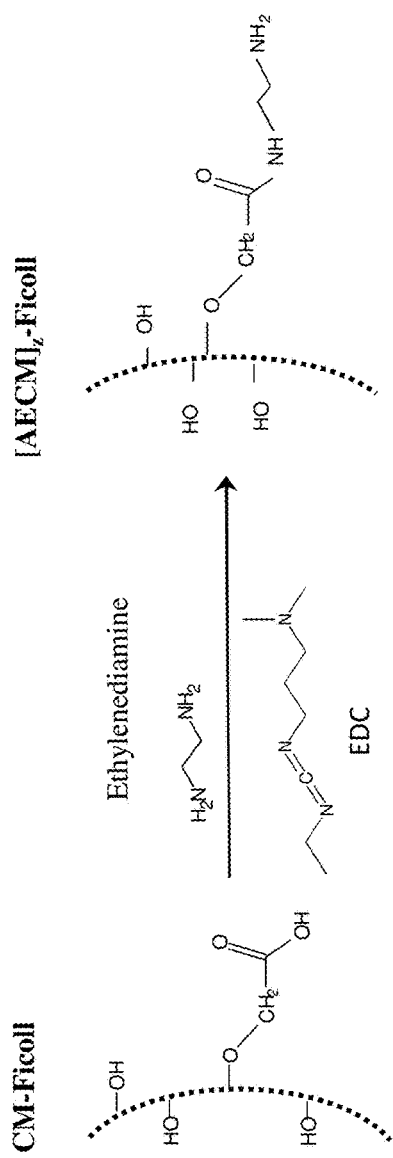
FIG. 4 shows the reaction scheme for the preparation of N-(2-aminoethyl)carbamylmethylated-FICOLL.

[AECM]$_z$-FICOLL is produced by reacting CM-FICOLL with a large excess of ethylenediamine and a water soluble carbodiimide. The reaction scheme is shown FIG. 4. The CM-FICOLL solution (about 30 mg/mL in 0.2 M aqueous sodium chloride) was transferred to a jacketed reaction vessel connected to a 22° C. circulating water bath for 20-30 min. To this CM-FICOLL solution, ethylenediamine di-hydrochloride (approximately 13800 molar equivalent per FICOLL) was added, and completely dissolved. The pH of the solution was adjusted to 4.7 with 1 N aqueous sodium hydroxide. Then, N-(3-dimethylaminopropyl)-N'-ethylcarbodiimide hydrochloride (EDC-HCl, approximately 835 molar equivalent per FICOLL) was added to the mixture over a period of 10 min while stirring. The pH of the solution was checked and if necessary adjusted to 4.7 with 1 N aqueous sodium hydroxide or 1 N aqueous hydrogen chloride. The reaction proceeded for 3.5 hours at 22° C. and during this time, the pH was adjusted to 4.7, as required. The crude [AECM]$_z$-FICOLL was purified by diafiltration using a system setup with a tangential flow fractionation (TFF) membrane having a 100 kDa MWCO. The crude [AECM]$_z$-FICOLL was diafiltered against 100 mM sodium phosphate and 150 mM sodium chloride, pH 7.5 buffer for a total of approximately 15-20 volume exchanges. The absorbance of each permeate diavolume was measured at 215 nm and the diafiltration was stopped when the permeate absorbance reached 0.1 AU. The purified [AECM]$_z$-FICOLL solution was concentrated to about 33 mg/mL, filtered using 0.22 μm pore size filter, aliquoted, and stored at −80° C. Three lots of [AECM]$_z$-FICOLL were prepared by this process, starting with 6.5 g, 7.0 g and 7.5 g of CM-FICOLL. The yields of [AECM]$_z$-FICOLL were 5.4 g, 5.9 g and 6.9 g, respectively. The amine to FICOLL molar ratios (z), determined using the procedures described in Example S4 and Example S5, were 221, 218 and 224, respectively.

Figure 5A:
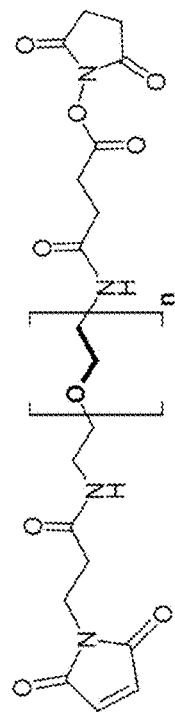
FIG. 5A-5E show the chemical structures of the succinimidyl-((N-maleimidopropionamido)-polyethyleneglycol) ester and succinimidyl-((N-maleimidoalkyl)-polyethyleneglycol) ester heterobifunctional linkers (SM-$PEG_n$).
Figure 5B:
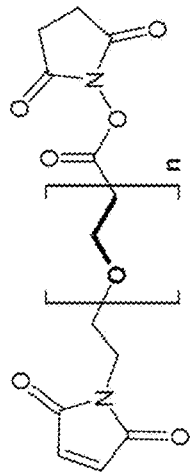
Figure 5C:
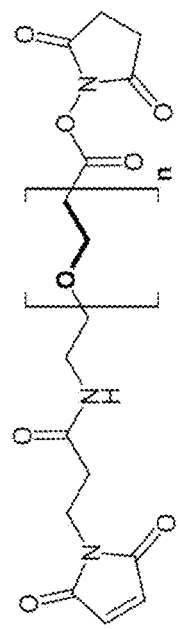
Figure 5D:
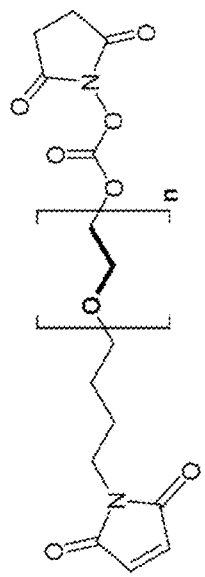
Figure 5E:
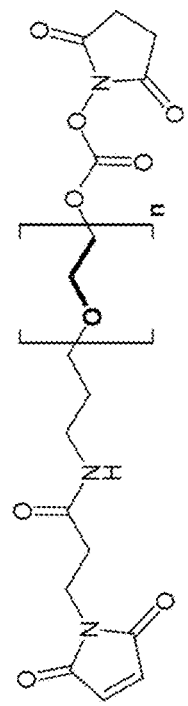

IV. Composition of SM-PEG$_6$ Heterobifunctional Linker. SM-PEG$_6$ (succinimidyl-((N-maleimidopropionamidol)-hexethyleneglycol) ester) was obtained from Thermo Scientific (Catalog #22105 Rockford, Ill.). SM-PEG$_6$ is an amine-to-sulfhydryl crosslinker with a molecular weight of 601.6 containing a hydrophilic polyethylene glycol (PEG) spacer arm of six ethylene glycol units. The spacer arm length is about 32 angstroms. The general chemical structures of SM-PEG$_n$ are shown in FIG. 5. For SM-PEG$_6$, n=6 and the structure of the compound used was as shown in FIG. 5A. For the preparation of D56-25, D56-26, and D56-27 in Example S13, SM-PEG$_n$ with n=24, 45, and 70 were used, respectively.

Figure 6:
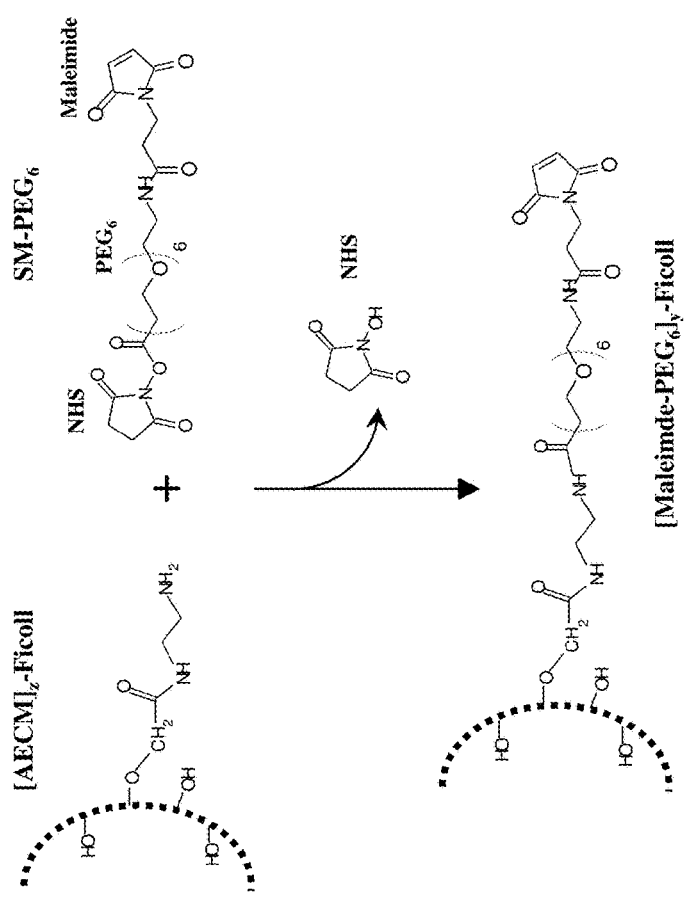
FIG. 6 shows the reaction scheme for preparation of [maleimide-$PEG_6$]$_y$-FICOLL.

V. Stage 1, Step 3: Preparation of [Maleimide-PEG$_6$]$_y$-FICOLL using SM-PEG$_6$. [Maleimide-PEG$_6$]$_y$-FICOLL was prepared by reaction of [AECM]$_z$-FICOLL with SM-PEG$_6$. The reaction scheme is shown in FIG. 6. [AECM]$_z$-FICOLL solution (20 mg/mL in 100 mM sodium phosphate and 150 mM sodium chloride, pH 7.5 buffer, amine to FICOLL molar ratio (z)=218-224) was transferred to a plastic bottle containing a stir bar. In a separate glass vial, SM-PEG$_6$ was dissolved in dimethylsulfoxide (DMSO) to a final concentration of 100 mg/mL solution. The SM-PEG$_6$ solution (5 equivalents per amine) was added slowly to the [AECM]$_z$-FICOLL, while stirring. The reaction bottle was transferred to a 25° C. dry air incubator, and the reaction proceeded for 40 min with gentle stirring. The reaction bottle was then transferred to room temperature (22-24° C.).

Unreacted amines on the FICOLL were capped using sulfo-N-hydroxysuccinimidyl-acetate (Su-NHS-Ac, Thermo Scientific, Rockford, Ill.). Su-NHS-Ac was dissolved in DMSO in a glass vial to a concentration of 100 mg/mL. The Su-NHS-Ac solution (5 equivalents per amine) was added to the [Maleimide-PEG$_6$]-FICOLL solution and was stirred for 15 min at room temperature. This capping reaction converts the unreacted amines on the FICOLL to acetamides, which may be important for the physicochemical properties of the resulting FICOLL product.

Unreacted SM-PEG$_6$ and Su-NHS-Ac were quenched with glycine. Glycine was dissolved in 100 mM sodium phosphate and 150 mM sodium chloride, pH 7.5 buffer to a concentration of 100 mg/mL and the solution was filtered using 0.22 μm pore size filter. The glycine solution (10 equivalents per total of SM-PEG$_6$ and Su-NHS-Ac) was added to the [Maleimide-PEG$_6$]$_y$-FICOLL solution and was stirred for 15 min at room temperature.

The [Maleimide-PEG$_6$]$_y$-FICOLL crude preparation was kept at low temperature (on wet ice) until ready for purification, which was performed on the same day as the conjugation reaction. The crude [Maleimide-PEG$_6$]$_y$-FICOLL was purified by diafiltration using a system setup with a tangential flow fractionation (TFF) membrane having a 100 kDa MWCO. The crude [Maleimide-PEG$_6$]$_y$-FICOLL was diluted to about 5.8 mg/mL using 100 mM sodium phosphate, 150 mM sodium chloride, pH 7.5 buffer, and was diafiltered against 100 mM sodium phosphate, 150 mM sodium chloride, pH 7.5 buffer for a total of approximately 24-29 volume exchanges. The absorbance of each permeate diavolume was measured at 215 nm and the diafiltration was stopped when the permeate absorbance reached 0.1 AU. The purified [Maleimide-PEG$_6$]$_y$-FICOLL was aliquoted into sterile polypropylene vials and stored at −80° C. The concentration was about 5.3 mg/mL. For the two largest scale reactions (Pilot Lots 4 and 5), 655 mg and 1900 mg of [AECM]$_z$-FICOLL were used and 444 mg and 1288 mg of purified [Maleimide-PEG$_6$]$_y$-FICOLL were isolated.

The maleimide to FICOLL molar ratio (y) of [Maleimide-PEG$_6$]$_y$-FICOLL was determined by the procedures outlined in Example S4 and Example S6. Table S3-1 shows the consistency of the [Maleimide-PEG$_6$]$_y$-FICOLL produced using three different lots of [AECM]$_z$-FICOLL, two different lots of SM-PEG$_6$ linker, and two different scales of production. Production of [Maleimide-PEG$_6$]$_y$-FICOLL having a specified range of maleimide:FICOLL molar ratios (y about 162-221) requires control of the following reagents and process parameters: 1) preparation of [AECM]$_z$-FICOLL with an amine:FICOLL molar ratio (z) of about 218-224, 2) having highly pure SM-PEG$_6$ linker, 3) and defined reaction conditions for reagent concentrations, stoichiometry, ionic strength, pH, time and temperature.

TABLE S3-1

Consistent Production of [Maleimide-PEG$_6$]$_y$-FICOLL at Bench and Pilot Scales Using Three Different Lots of [AECM]$_z$-FICOLL and Two Different Lots of SM-PEG$_6$

| [Maleimide-PEG$_6$]$_y$-FICOLL Lot No. | SM-PEG$_6$ linker Lot No. | Amine:FICOLL molar ratio (z) | Maleimide:FICOLL molar ratio (y) |
|---|---|---|---|
| Bench Lot 1 | Lot A | 218 (Lot 2) | 174 |
| Bench Lot 2 | Lot A | 218 (Lot 2) | 162 |
| Bench Lot 3 | Lot A | 218 (Lot 2) | 176 |
| Bench Lot 4 | Lot A | 218 (Lot 2) | 181 |
| Pilot Lot 1 | Lot A | 221 (Lot 1) | 163 |
| Pilot Lot 2 | Lot A | 218 (Lot 2) | 182 |
| Pilot Lot 3 | Lot A | 224 (Lot 3) | 187 |
| Pilot Lot 4 | Lot B | 224 (Lot 3) | 221 |
| Pilot Lot 5 | Lot B | 224 (Lot 3) | 206 |

Figure 7:
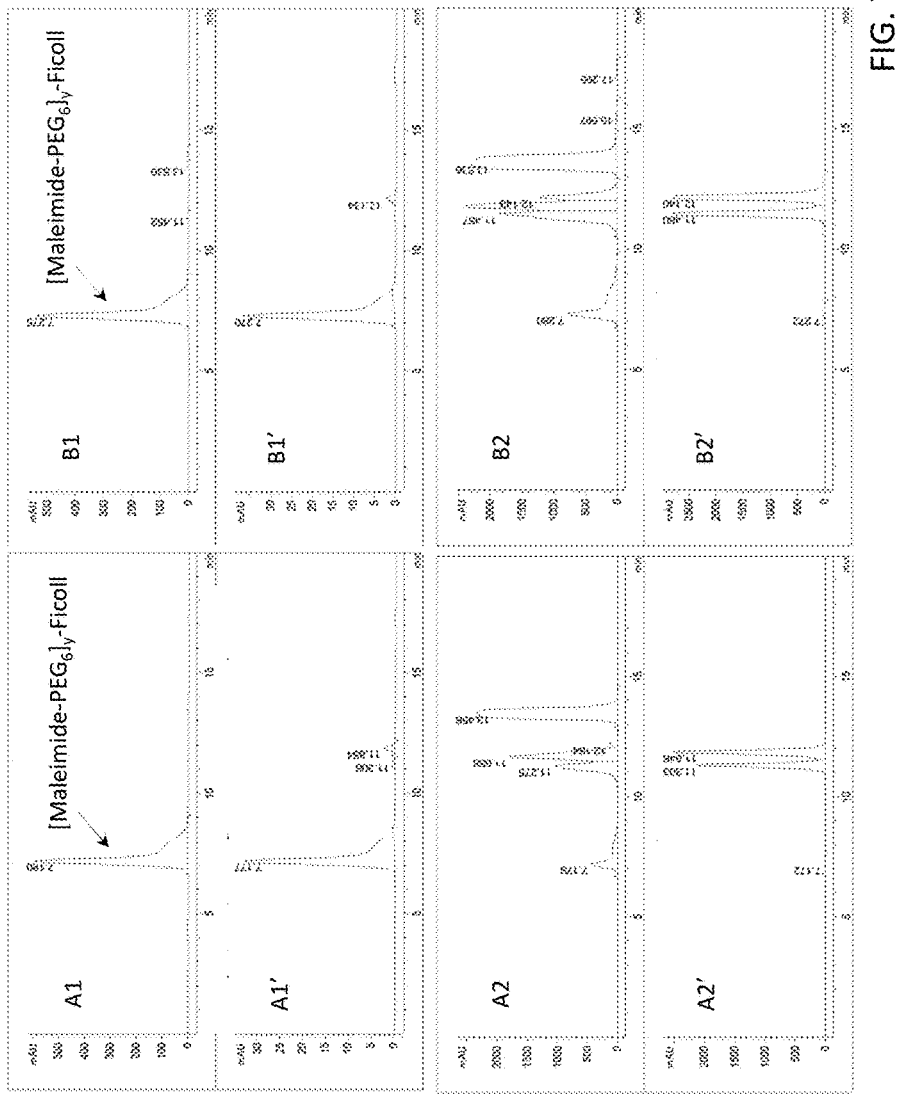
FIG. 7 provides results from the size exclusion chromatography-high performance liquid chromatography analysis of [maleimide-$PEG_6$]$_y$-FICOLL Pilot Lots 4 and 5. A1 is from purified Pilot Lot 4, A2 is from crude Pilot Lot 4, B1 is from purified Pilot Lot 5, and B2 is from crude Pilot Lot 5. Upper and lower chromatograms in each quadrant represent detection at 215 nm and 260 nm, respectively. [Maleimide-$PEG_6$]$_y$-FICOLL eluted at about 7.2 min. Unreacted reagents and small molecules eluted from about 11.2 to 17.3 min.

The purity of [Maleimide-PEG$_6$]$_y$-FICOLL Pilots Lots 4 and 5 was assessed by size exclusion chromatography—high performance liquid chromatography (SEC-HPLC) using the parameters shown in Table S3-2. The chromatograms for crude and purified Pilot Lots 4 and 5 are shown in FIG. 7. Purified Pilot Lots 4 and 5 were 100% and 99.6% pure, respectively.

TABLE S3-2

SEC-HPLC Method For Purity Determination

| | |
|---|---|
| Column | TOSOH TSK-Gel G3000 PW$_{XL}$ |
| Dimensions | 7.8 mm × 30 cm |
| Bed Volume | 14.3 ml |
| Flow Rate | 0.75 ml/min |
| Mobile Phase | 10 mM sodium phosphate, 141.7 mM sodium chloride, pH 7.2 buffer |
| Run Time | 20 min |
| Detection | UV at 215 and 260 nm |
| Injection Volume | 20 μl |

The [Maleimide-PEG$_6$]$_y$-FICOLL manufactured using the SM-PEG$_6$ linker was significantly more soluble in aqueous buffers than [Maleimide-MC]$_y$-FICOLL manufactured using the sulfosuccinimidyl 4-(N-maleimidomethyl)cyclohexane-1-carboxylate (sulfo-SMCC) linker, which was previously described in U.S. Pat. No. 8,597,665. The sulfo-SMCC linker results in a hydrophobic methylcyclohexyl (MC) linking group, which causes the [Maleimide-MC]$_y$-FICOLL to oil out and/or precipitate in aqueous buffers after freeze/thaw cycle(s), and results in unreliable reaction with the thiol-activated polynucleotide (PN) or chimeric compound (CC). If the [Maleimide-PEG$_6$]$_y$-FICOLL or [Maleimide-MC]$_y$-FICOLL are not used on the day they are prepared, they must be stored frozen so that the maleimide group remains active. The heterogeneous mixtures of [Maleimide- MC]$_y$-FICOLL were not used in conjugation reactions with D56-03 (aka (D56-01)-3'-SH) due to their poor stability. Refer to Example S14 for the synthesis of [Maleimide-MC]$_y$-FICOLL.

Figure 8:
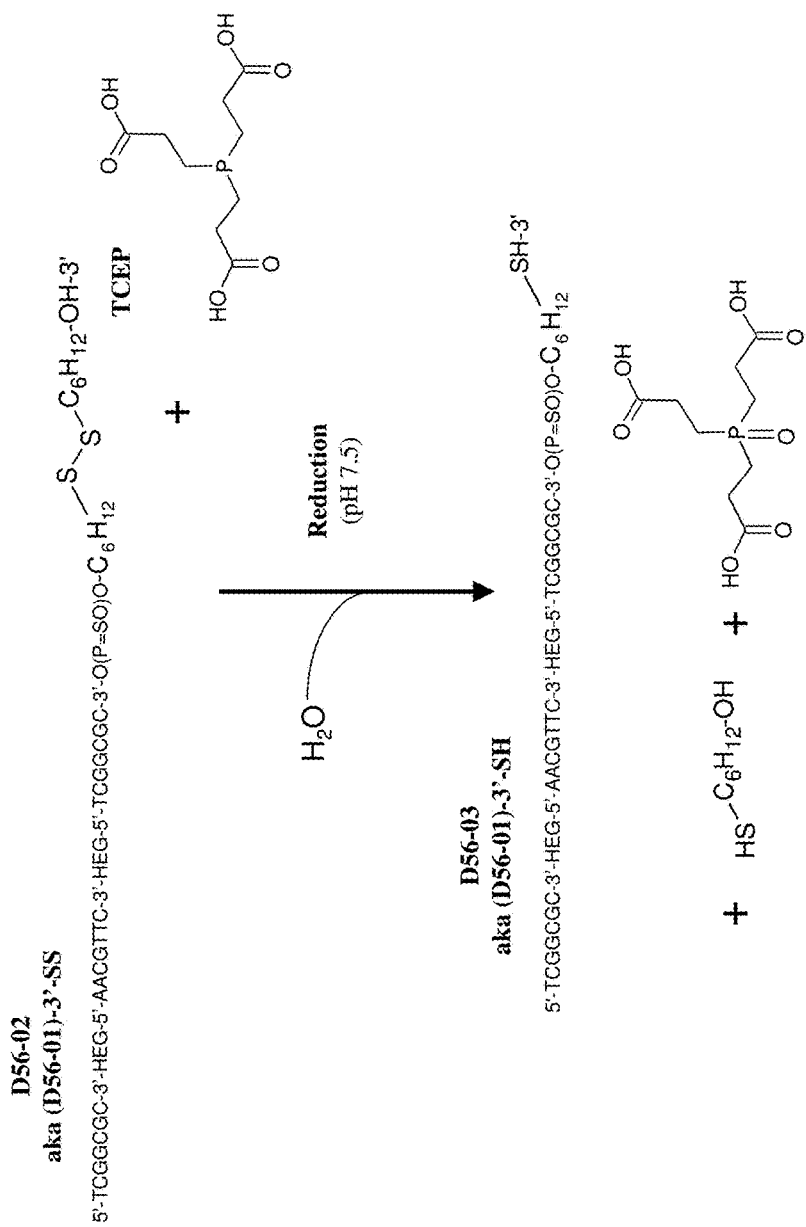
FIG. 8 shows the reaction scheme for preparation of D56-03 (SEQ ID NO:2) from D56-02 (SEQ ID NO:2), which differ in non-nucleotide moieties at their 3' ends.

F. Stage 2, Step 1: Preparation of D56-03 (aka (D56-01)-3'-SH). D56-03 (thiol) was prepared by reaction of D56-02 (disulfide) with excess tris(2-carboxyethyl)phosphine hydrochloride (TCEP). The reaction scheme is shown in FIG. 8. On the day of production, D56-02 (aka (D56-01)-3'-SS) was removed from the freezer and allowed to equilibrate to room temperature for at least 1-2 hours before opening the bottle to minimize water uptake in the hygroscopic lyophilized solid. D56-02 was dissolved in activation buffer (100 mM sodium phosphate, 150 mM sodium chloride, 1 mM ethylenediaminetetraacetic acid (EDTA), pH 7.5) to a nominal concentration of about 56 mg/mL. The actual concentration of the solution was determined by absorbance at 260 nm using an extinction coefficient of 22.65 mg/mL$^{-1}$ cm$^{-1}$. The concentration was adjusted to approximately 25 mg/ml with activation buffer, and verified by absorbance at 260 nm.

TCEP-HCl was obtained from Thermo Scientific (Catalog #20490, Rockford, Ill.). On the day of production, TCEP-HCl was dissolved in activation buffer to a concentration of 48±1 mg/mL. The TCEP solution was kept at ambient lab temperature and used within 3 hours.

To the D56-02 solution, TCEP solution (5 equivalents) was added at room temperature with stirring. The reaction vessel was transferred to a 40±2° C. water bath, and the reduction step proceeded for 120±10 min. The resulting crude D56-03 solution was allowed to cool to room temperature for about 10-15 min prior to purification. This reaction was performed on 989 mg of D56-02 for Pilot Lot 4 and in two parts on 1814 mg and 1836 mg of D56-02 for Pilot Lot 5.

Purification of D56-03 was achieved by gel filtration using Sephadex G-25 Fine (Catalog #17-0032, GE Healthcare, Pittsburgh, Pa.) packed into XK50/30 columns (GE Healthcare) according to the manufacturer's recommended procedures. The G25 desalting chromatography columns were controlled by an AKTA purifier chromatography system, (GE Healthcare, formerly Amersham Pharmacia Biotech). The crude D56-03 solution was loaded onto the G25 column at a ratio of 15-16% of sample volume to column volume. The mobile phase was applied to the column at a flow rate of 30 cm/hr. The eluent from the column was monitored at 215 nm and 260 nm, and sample collection started when eluent absorbance rose above approximately 100 mAU. A total volume of about 1.6 to 1.7 times the sample volume loaded on the column was collected. The purified D56-03 solutions were aliquoted and stored at −80° C. Details of the purification of Pilot Lots 4 and 5 are detailed in Table S3-3.

TABLE S3-3

Purification of D56-03 Pilot Lots 4 and 5

|  | Step | D56-03 Pilot Lot 4 | D56-03 Pilot Lot 5 Part 1 | D56-03 Pilot Lot 5 Part 2 |
|---|---|---|---|---|
| Crude D56-03 Gel Filtration | Sample volume | 41 mL | 77 mL | 78 mL |
|  | Sample amount | 984 mg | 1874 mg | 1833 mg |
|  | Sephadex G-25 bed size (Diameter × Height) | 5 × 13 cm | 5 × 26 cm | 5 × 26 cm |
|  | Sephadex G-25 column volume | 255 mL | 510 mL | 510 mL |
|  | Mobile phase | 100 mM sodium phosphate, 150 mM sodium chloride, 1 mM EDTA, pH 7.5 buffer | | |
|  | Operating flow rate | 30 cm/hr 9.8 ml/min | 30 cm/hr 9.8 ml/min | 30 cm/hr 9.8 ml/min |
|  | Sample volume to column volume ratio | 16% | 15% | 15% |
|  | Temperature | RT (22-24° C.) | RT (22-24° C.) | RT (22-24° C.) |
|  | Column back pressure | Not recorded | 0.16 MPa | 0.19 MPa |
| Purified D56-03 | D56-03 pool volume collected | 70 mL | 127 mL | 128 mL |
|  | Pool volume to sample volume ratio | 1.7 | 1.6 | 1.6 |

The purity of D56-03 was determined by SEC-HPLC using the procedure outlined in Table S3-2 and was 100% for Pilot Lots 4 and 5 (FIG. 9). For Pilot Lots 4 and 5, 802 mg and 2904 mg of D56-03 were isolated, respectively.

Figure 10:
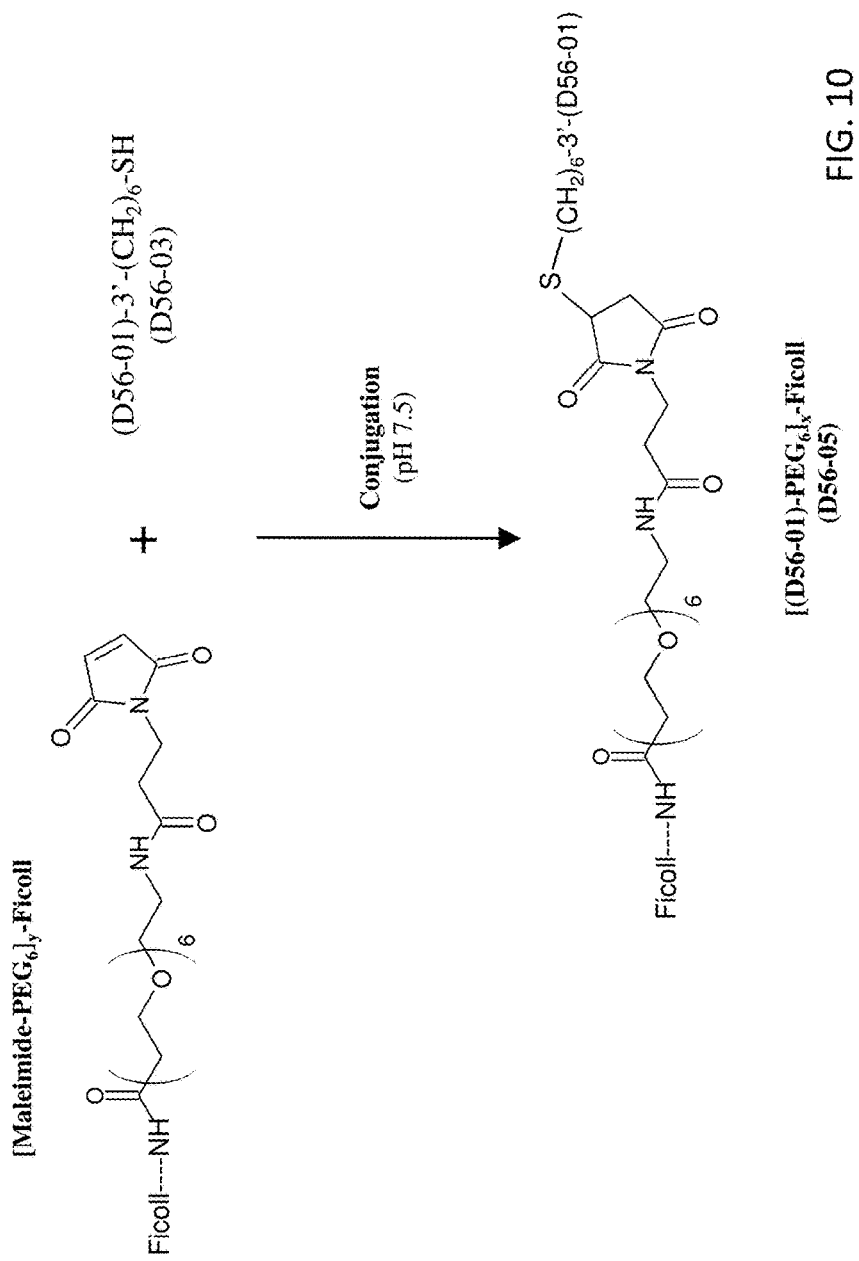
FIG. 10 shows the reaction scheme for preparation of D56-05.
Figure 11E:
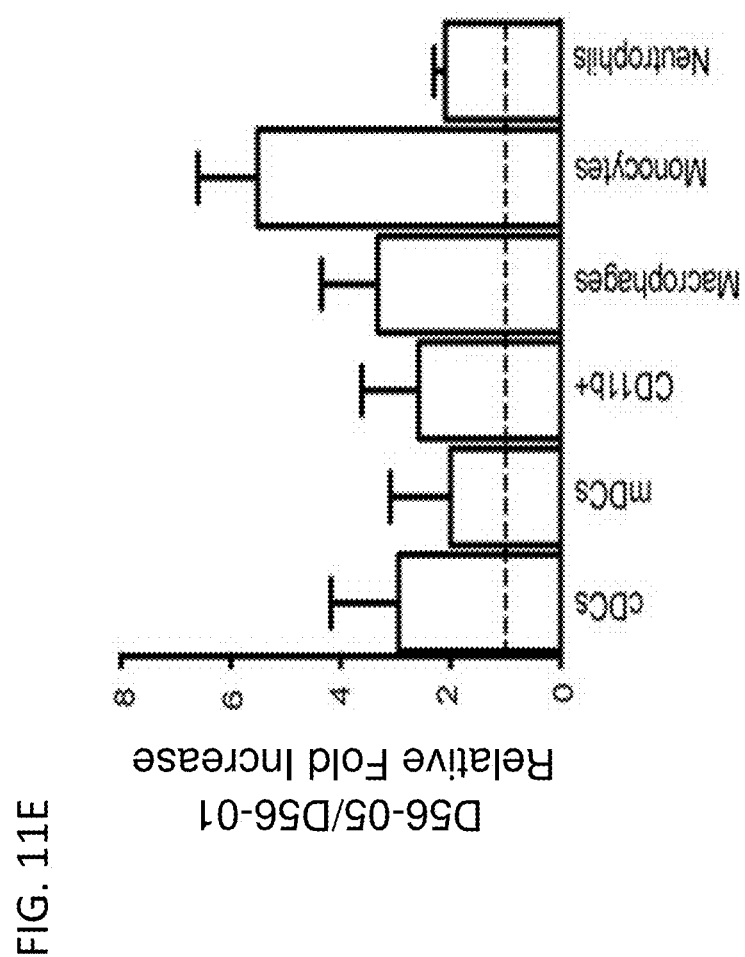
Figure 12A:
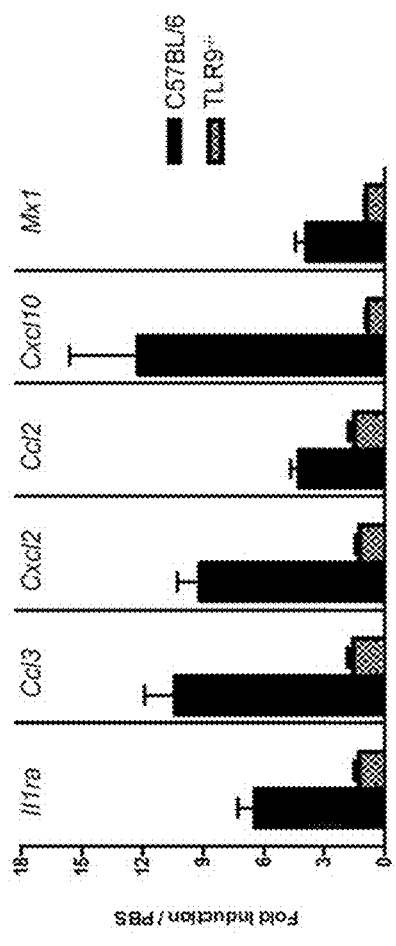
FIG. 12A-B show adjuvant effects of D56-05 are dependent on TLR9 expression.
Figure 12B:
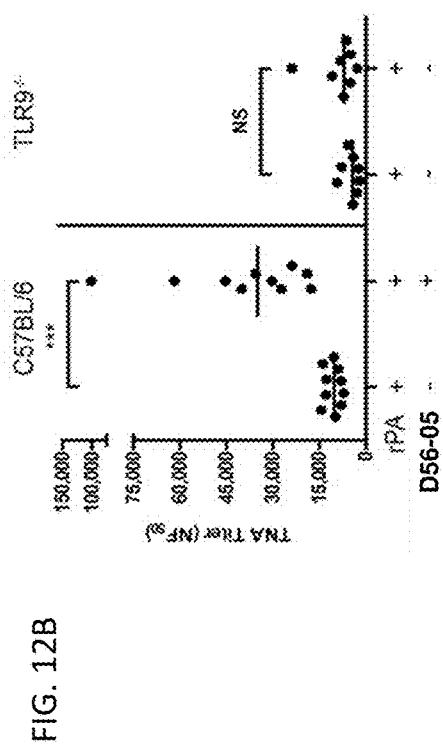
Figure 14:
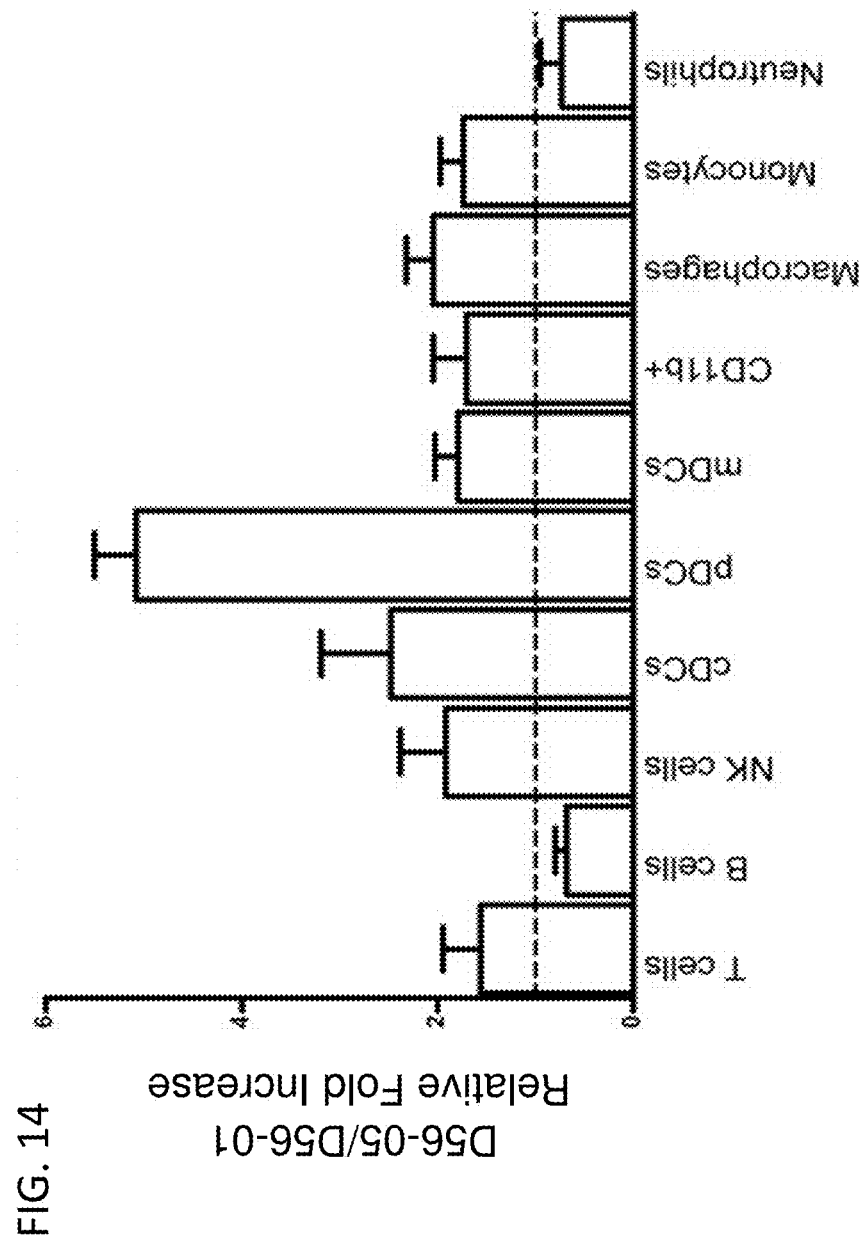
FIG. 14 shows D56-05 nanoparticles enhance cell recruitment in draining lymph nodes. The relative proportions of different cell populations in popliteal lymph nodes of BALB/c mice (n=4-6) immunized s.c. in footpads 48 hours earlier with 10 mg D56-05 or D56-01 in combination with 10 or 2 mg rPA were analyzed by flow cytometry. Following light scatter gating, cell populations were identified as follows: T cells ($CD3^+/CD19^-$), B cells ($CD3^-/CD19^+$), NK cells ($CD3^-/CD19^-/CD49b^+$), and the following $CD3^-/CD19^-/CD49b^-$ cell populations: cDCs ($CD11b^-/CD11c^+/MHC\ II^+$), pDCs ($CD11b^-/CD11c^+/MHC\ II^+/PDCA1^+$ or $B220^+$), mDCs ($CD11b^+/CD11c^+/MHC\ II^+$), myeloid cells ($CD11b^+/CD11c^-/MHC\ II^+$), macrophages ($CD11b^+/CD11c^-/MHC\ II^+/F4/80^+/Ly6C^+/Ly6G^-$), monocytes ($CD11b^+/CD11c^-/MHC\ II^+/F4/80^-/Ly6C^+/Ly6G^-$), and neutrophils ($CD11b^+/CD11c^-/Ly6G^+$). Data are shown as means with SEM and are representative of four independent experiments.

G. Stage 3, Step 1: Preparation of D56-05 (aka [(D56-01)-PEG$_6$]$_x$-FICOLL. D56-05 was prepared by reaction of [Maleimide-PEG$_6$]$_y$-FICOLL with D56-03 (aka (D56-01)-3'-SH). The reaction scheme is shown in FIG. 10.

Both [Maleimide-PEG$_6$]$_y$-FICOLL and D56-03 are reactive and must be handled with care. Both materials were stored frozen at −80° C. and were thawed in a 4° C. water bath for several hours just prior to use. The [Maleimide-PEG$_6$]$_y$-FICOLL solution (about 5.3 mg/mL, maleimide:FICOLL molar ratio (y)=206-221) was transferred to a plastic bottle containing a stir bar. To this solution, a solution of D56-03 (about 11.5 mg/mL, 0.64-0.69 equivalents per maleimide, 141 equivalents per FICOLL) was added while stirring. The volume in the reaction vessel was adjusted with 100 mM sodium phosphate, 150 mM sodium chloride, pH 7.5 in order to obtain a final D56-03 concentration of 5 mg/mL. The conjugation reaction was then transferred to a 25° C. dry air incubator, and the reaction proceeded for 1 hour with gentle stirring. For Pilot Lot 4, 218 mg of [Maleimide-PEG$_6$]$_y$-FICOLL and 600 mg of D56-03 were used. For Pilot Lot 5, 874 mg of [Maleimide-PEG$_6$]$_y$-FICOLL and 2400 mg of D56-03 were used.

Unreacted maleimide groups on the FICOLL were capped for 15 min at room temperature using a 100 mg/mL solution of cysteine in 100 mM sodium phosphate, 150 mM sodium chloride, pH 7.5 buffer (10 equivalents per maleimide). The crude [(D56-01)-PEG$_6$]$_x$-FICOLL was then transferred to the cold room (2-8° C.), and stored overnight. This capping reaction introduces cysteine onto the FICOLL (via a covalent bond through the sulfur), and may be important for the physicochemical properties of the D56-05 (aka [(D56-01)-PEG$_6$]$_x$-FICOLL) product.

Purification of D56-05 was performed by diafiltration, as described in Table S3-4. The volume of crude D56-05 was adjusted with 10 mM sodium phosphate, 142 mM sodium chloride, pH 7.2 buffer. At each diavolume (a volume of permeate equal to the starting sample volume in the feed reservoir), a sample of permeate was taken to determine the absorbance at 215 nm. Diafiltration was ended when the permeate absorbance dropped below 0.05 AU. Upon completion of diafiltration, the D56-05 sample was recovered from TFF system and sterile filtered using a 0.22 μm filter. The D56-05 was aliquoted and stored at <−60° C. D56-05 pilot lots were characterized and the results are provided in Example S9.

TABLE S3-4

Parameters and Conditions for Diafiltration of D56-05 Pilot Lots 4 and 5

| | Step | D56-05 Pilot 4 | D56-05 Pilot 5 |
|---|---|---|---|
| Crude D56-05 | Sample volume | 121 mL | 485 mL |
| | Sample amount | 593 mg | 2386 mg |
| | Final sample volume after adjustment | 200 mL | 600 mL |
| D56-05 Diafiltration | Membrane surface area | 0.1 m$^2$ | 0.2 m$^2$ |
| | Buffer | 10 mM sodium phosphate, 142 mM sodium chloride, pH 7.2 buffer | |
| | Tubing Size | LS/16 | LS/15 |
| | Pump Speed | 150-160 mL/min | 200 mL/min |
| | Average Permeate Flow Rate | 50 mL/min | 67 mL/min |
| | Temperature | (22-24° C.) | (22-24° C.) |
| | Transmembrane pressure | 1 to 8 psi | 2.2 to 9.8 psi |
| | Total Buffer | 6.2 liters | 14 liters |
| | Number of buffer exchanges | 31 diavolumes[a] | 23 diavolumes[a] |
| | Duration | 3.3 hours | 3.5 hours |
| | Permeate absorbance at 215 nm at end of diafiltration | 0.028 AU | 0.036 AU |
| Purified D56-05 | Volume | 130 mL | ~375 mL[b] |

[a]Diavolume is the volume of permeate equivalent to the sample volume in the feed reservoir. Each diavolume is one buffer exchange.
[b]Volume of D56-05 Pilot 5 after diafiltration was an approximation. An actual volume measurement was not performed.

Example S4: Procedure to Determine FICOLL Concentration in FICOLL-Containing Intermediates and Products The FICOLL concentrations of FICOLL-containing intermediates and products were determined using the Pierce Glycoprotein Carbohydrate Estimation Kit (Product #23260, Thermo Scientific, Rockford, Ill.) as per the manufacturer's protocol, except that FICOLL PM400 was used to create a standard curve for the assay.

Example S5: Procedure to Determine Amine Concentration and Amine:FICOLL Molar Ratio (z) in [AECM]$_z$-FICOLL Solutions The amine concentration of [AECM]$_z$-FICOLL was determined using the Pierce Fluoraldehyde OPA Reagent Solution (Product #26025, Thermo Scientific, Rockford, Ill.) as per the manufacturer's protocol. Glycine was used to create a standard curve for the assay. The Amine:FICOLL molar ratio (z) was calculated by dividing the amine concentration by the FICOLL concentration, where the FICOLL concentration was determined as described in Example S4 and the concentrations were in units of molarity.

Example S6: Procedure to Determine Maleimide Concentration and Maleimide:FICOLL Molar Ratio (y) in [Maleimide]$_y$-FICOLL Solutions The maleimide concentrations of [Maleimide-PEG$_6$]$_y$-FICOLL and [Maleimide-MC]$_y$-FICOLL were determined using Ellman's reagent (5,5'-dithio-bis-(2-nitrobenzoic acid), Product No. 22582, Thermo Scientific, Rockford, Ill.). The [Maleimide]$_y$-FICOLL was reacted with excess cysteine as per the manufacturer's protocol, and the remaining cysteine was quantified using a cysteine standard curve. The maleimide concentration was determined by subtracting the remaining cysteine concentration from the initial cysteine concentration. The Maleimide:FICOLL molar ratio (y) was calculated by dividing the maleimide concentration by the FICOLL concentration, where the FICOLL concentration was determined as described in Example S4 and the concentrations were in units of molarity.

Example S7: Procedure to Determine Polynucleotide (PN) or Chimeric Compound (CC) Concentration and PN:FICOLL or CC:FICOLL Molar Ratio (x) in FICOLL Conjugates (e.g., D56-05, aka [(D56-01)-PEG$_6$]$_x$-FICOLL)

The D56-01 (CC) concentration of D56-05 (aka [(D56-01)-PEG$_6$]$_x$-FICOLL) was determined using ultraviolet spectrophotometry and the Beer's law equation. (Note that by convention, the chimeric compound attached to the FICOLL is referred to by the sequence name, D56-01, at this stage even though the chimeric compound with the linker, D56-03, was used to form this compound.) The absorbance at 260 nm was determined and an extinction coefficient of 22.65 mg/ml$^{-1}$×cm$^{-1}$ for D56-01 was used. FICOLL and the linkers do not absorb at 260 nm, so the absorbance is solely due to the absorbance of the CC, D56-01. The D56-01 concentration in mg/mL was converted to a molar concentration using the molecular weight of the free acid for D56-01. The CC:FICOLL molar ratio (x) was determined by dividing the CC concentration by the FICOLL concentration, where the FICOLL concentration was determined as described in Example S4 and the concentrations were in units of molarity. Concentrations for other PN-FICOLL or CC-FICOLL solutions are determined using the extinction coefficient and free acid molecular weight for the PN or CC used, as appropriate.

Example S8: Procedure to Determine Particle Size

The particle sizes (Z-average) and standard deviations (SD) of FICOLL samples (e.g., D56-05) were measured by dynamic light scattering (DLS) using a Malvern Zetasizer instrument. Samples were diluted to a FICOLL concentration of 0.5 mg/mL in 10 mM sodium phosphate, 142 mM sodium chloride, pH 7.2 buffer, and measured under defined instrument settings. A calibrated 50 nm polystyrene nanosphere sample (Product #3050A, Thermo Scientific, Rockford, Ill.) was included in the analysis as a system suitability control and had had a particle size of 49±6 nm.

Example S9: Physicochemical Characterization of Purified D56-05, aka [(D56-01)-PEG$_6$]$_x$-FICOLL Five pilot lots of D56-05 (aka [(D56-01)-PEG$_6$]$_x$-FICOLL) have been manufactured using the procedure outlined in Example S3. These lots were characterized and the results are summarized in Table S9-1. Purity was determined by SEC-HPLC using the procedure outlined in Table S3-2 with detection at 215 nm and ranged from >99% to 100%. FICOLL concentration was determined by the procedure described in Example S4. The FICOLL concentration can be targeted by controlling the final concentration of the retentate in the diafiltration. D56-01 concentration and the D56-01:FICOLL ratio (x) were determined by the procedure described in Example S7. The D56-01:FICOLL molar ratio (x) ranged from 117 to 140, demonstrating that the manufacturing procedure described in Example S3 provides a high level of control for the loading of the chimeric compound on the FICOLL. The target D56-01:FICOLL molar ratio (x) for this process is 120±30. The particle size of D56-05 was determined as described in Example S8.

Selection of the composition of the formulation to be lyophilized was based upon pre-formulation studies using Generally Regarded as Safe (GRAS) excipients to control pH and ionic strength, which can affect thermal stability. A series of test formulations based upon D56-05 primate dosages were tested for freeze/thaw stability and evaluated on the basis of solution clarity and HPLC sizing chromatography. A formulation containing 1 mg/ml D56-05 (Pilot Lot 2), 10 mM potassium phosphate (pH=7.5) and 300 mM trehalose showed identical chromatographic behavior and dynamic light scattering profiles through the 10-cycle experiment and was selected for further development. The formulation described above was subjected to a lyophilization cycle, consisting of shelf-freezing at approximately −35° C., followed by 36 hours of primary drying at −35° C. (−60 μbar vacuum), 2-hour transition to shelf temperature at 30° C., and secondary drying for an additional 24 hours. The lyophilized product (40 vials) was an acceptable cake shown to have residual moisture of 1-1.4%. The formulation was reconstituted in 1 mL of water and the product was shown

TABLE S9-1

Summary of the Physical Characterization of Purified D56-05 Pilot Lots

| Attribute | Pilot 1 | Pilot 2 | Pilot 3 | Pilot 4 | Pilot 5 |
|---|---|---|---|---|---|
| Appearance[a] | Clear liquid | Clear liquid | Clear liquid | Clear liquid | Clear liquid |
| pH | 7.3 | 7.2 | 7.1 | 7.2 | 7.2 |
| Purity (area %)[b] | >99% | >99% | >99 | 100% | 100% |
| Residual D56-03 (area %)[b] | <1% | <1% | <1% | 0% | 0% |
| FICOLL concentration (mg/mL)[c] | 1.3 | 1.2 | 1.3 | 1.6 | 2.3 |
| D56-01 concentration (mg/mL)[d] | 2.9 | 3.2 | 3.0 | 3.8 | 5.7 |
| D56-01:FICOLL molar ratio (x) | 117 | 140 | 117 | 126 | 125 |
| Particle size (nm): Z-average ± SD[e] | 49 ± 20 | 53 ± 23 | 47 ± 20 | 47 ± 20 | 48 ± 20 |

[a]Appearance was determined by visual evaluation.
[b]Purity and residual D56-03 (aka (D56-01)-3'-SH) was determined using an SEC-HPLC silica-based column using the parameters in Table S3-2 with detection at 215 nm.
[c]FICOLL concentrations were determined as described in Example S4.
[d]D56-01 concentrations and D56-01:FICOLL molar ratios (x) were determined as described in Example S7.
[e]Mean particle diameter was determined as described in Example S8.

The results shown in Table S9-1 illustrate the consistency of production of five consecutively-produced pilot lots of D56-05. This high level of control for the key attributes D56-01:FICOLL molar ratio (x) and particle size of D56-05 was achieved by using the reagents and procedures outlined in Example S3. Use of the SM-PEG$_6$ linker instead of the sulfo-SMCC linker to manufacture the [Maleimide]$_y$-FICOLL was critical, as the SM-PEG$_6$ linker made the product significantly more water soluble leading to improved control of the maleimide:FICOLL molar ratio (y) and reactivity with D56-03. Additionally, the quality (purity) of the reagents and control of process parameters, including number of equivalents, concentrations, pH, ionic strength, time, and temperature (as described in Example S3), were critical for achieving consistent results. Development of the analytical procedures described in Examples S4-S8 were also necessary for control of the process.

Example S10: D56-05 Lyophilized Formulation

Limitations in the stability of D56-05 solution formulations stored above 5° C. led to development of a D56-05 lyophilized formulation, with the goal of achieving good stability at controlled room temperature (see Example S11).

to behave identically by SEC-HPLC when analyzed directly after formulation or after the lyophilization and reconstitution process.

Example S11: Stability of D56-05 (aka [(D56-01)-PEG$_6$]$_x$-FICOLL) Solution and Lyophilized Formulations This example describes the stability of liquid and lyophilized substances.

A. D56-05 Solution Formulation Stability. The stability of the D56-05 (aka [(D56-01)-PEG$_6$]$_x$-FICOLL) solution formulation over 12 months of storage was evaluated. The solution formulation consisted of D56-05 dissolved in 10 mM sodium phosphate, 142 mM sodium chloride, pH 7.2 buffer at concentrations of about 3-5 mg/mL. The stability of D56-05 solution formulation (Pilot Lot 4) was evaluated at storage temperatures of −80° C., 5° C. and 37° C. The stability tests included pH, D56-01 concentration (Example S7), % purity of D56-05 by SEC-HPLC (Table S3-2, detection at 215 nm) and particle size analysis (Example S8).

Table S11-1 and Table S11-2 show the stability results for D56-05 (aka [(D56-01)-PEG$_6$]$_x$-FICOLL) solution formulation, Pilot Lot 4, stored at −80° C., 5° C. and 37° C. for up to 12 months. The time 0 results are shown in Table S9-1.

TABLE S11-1

Stability Results for D56-05 (aka [(D56-01)-PEG$_6$]$_x$-FICOLL) Solution Formulation, Pilot Lot 4

| | \multicolumn{4}{c|}{Test} | | | | | | | | | |
|---|---|---|---|---|---|---|---|---|---|---|---|---|---|
| | \multicolumn{4}{c|}{pH} | \multicolumn{4}{c|}{D56-01 Concentration (mg/mL)} | \multicolumn{5}{c|}{% Purity of D56-05 by SEC-HPLC, area %[a]} |
| Sample | \multicolumn{4}{c|}{Months} | \multicolumn{4}{c|}{Months} | \multicolumn{5}{c|}{Months} |
| Temp. | 3 | 6 | 9 | 12 | 3 | 6 | 9 | 12 | 1 | 3 | 6 | 9 | 12 |
| −80° C. | 7.3 | 7.3 | 7.3 | 7.3 | 3.6 | 3.6 | 3.6 | 3.4 | 98.9 | 99.6 | 100 | 99.6 | 99.6 |
| 5° C. | 7.2 | 7.2 | 7.2 | 7.1 | 3.7 | 3.7 | 3.8 | 3.4 | 99.0 | 99.5 | 98.3 | 98.1 | 97.8 |
| 37° C.[b] | 7.0 | 6.5 | 6.4 | N/A | 3.9 | N/A | N/A | N/A | 93.4 | 89.0 | 79.1 | 77.4 | N/A |

[a] A polymer column (TSK-Gel G3000PW$_{XL}$) was used to test the 1-month stability samples. A silica column (TSK-Gel G3000SW$_{XL}$) was used to test the 3, 6, 9 and 12-month stability time-point samples. Purity determined at 215 nm.
[b] Some samples stored at 37° C. were compromised due to crack in cap to tube and thus were not analyzed. These samples are reported as N/A (data not available).

TABLE S11-2

Particle Size Distribution of D56-05 (aka [(D56-01)-PEG$_6$]$_x$-FICOLL) Solution Formulation, Pilot Lot 4 Stability Samples

| Time Point | Storage Temperature | Intensity |
|---|---|---|
| 1-Month | −80° C. | 45.9 ± 22.9 nm |
| | 5° C. | 45.9 ± 22.5 nm |
| | 37° C. | 44.9 ± 21.6 nm |
| 3-Months | −80° C. | 54.3 ± 27.5 nm |
| | 5° C. | 58.6 ± 28.9 nm |
| | 37° C. | 62.4 ± 30.5 nm |
| 6-Months | −80° C. | 49.8 ± 23.1 nm |
| | 5° C. | 52.7 ± 27.5 nm |
| | 37° C. | 47.3 ± 22.4 nm |
| 9-Months | −80° C. | 49.8 ± 21.6 nm |
| | 5° C. | 49.3 ± 20.6 nm |
| | 37° C. | 45.2 ± 19.9 nm |
| 12-Months | −80° C. | 49.0 ± 21 nm |
| | 5° C. | 48.7 ± 21 nm |
| | 37° C. | Not available |

For the D56-05 solution formulation, Pilot Lot 4, the pH, D56-01 concentration, D56-05 purity and particle size did not change significantly with storage at frozen (−80° C.) or refrigerated (5° C.) conditions for up to 12 months. However, at 37° C., both pH and D56-05 purity decreased significantly with longer storage times, while D56-01 concentration and particle size remained consistent. The consistency of the D56-05 particle size under the different storage conditions shows that D56-05 does not aggregate over time.

B. D56-05 Lyophilized Formulation Stability. The stability of the D56-05 (aka [(D56-01)-PEG$_6$]$_x$-FICOLL) lyophilized formulation over 12 months of storage was evaluated. The lyophilized formulation is described in Example S10. The stability of D56-05 lyophilized formulation was evaluated at storage temperatures of 4° C., 25° C. and 37° C. The stability tests included pH, D56-01 concentration (Example S7), % purity of D56-05 by SEC-HPLC (Table S3-2 with detection at 215 nm) and particle size analysis (Example S8).

Table S11-3 shows the stability results for the D56-05 (aka [(D56-01)-PEG$_6$]$_x$-FICOLL) lyophilized formulation stored at 4° C., 25° C. and 37° C. for up to 12 months. Data for the D56-05 formulation before lyophilization (pre-lyo) is also included in Table S11-3.

TABLE S11-3

Stability Results for D56-05 (aka [(D56-01)-PEG$_6$]$_x$-FICOLL) Lyophilized Formulation (Formulation in Example S10)

| Test | Pre-lyo | T$_0$ | \multicolumn{3}{c|}{1 Month} | \multicolumn{3}{c|}{6 Months} | \multicolumn{3}{c|}{12 Months} |
|---|---|---|---|---|---|---|---|---|---|---|---|
| | | | 4° C. | 25° C. | 37° C. | 4° C. | 25° C. | 37° C. | 4° C. | 25° C. | 37° C. |
| pH | 7.5 | 7.4 | 7.5 | 7.5 | 7.5 | 7.6 | 7.5 | 7.6 | 7.5 | 7.5 | 7.4 |
| [D56-01] (mg/mL) | 1.0 | 1.0 | 1.0 | 1.0 | 1.0 | 1.0 | 1.0 | 1.0 | 1.0 | 1.0 | 1.0 |
| Purity (area %) | 99.5 | 99.5 | 99.4 | 99.4 | 99.5 | 100 | 100 | 100 | 99.6 | 99.7 | 99.5 |
| Particle size[b] (nm) | 35 ± 16 | 28 ± 17 | 27 ± 17 | 28 ± 20 | 34 ± 23 | 28 ± 18 | 48 ± 35 | 67 ± 47 | 28 ± 18 | 50 ± 35 | 217 ± 159 |

For the D56-05 lyophilized formulation, the pH, D56-01 concentration, and D56-05 purity did not change significantly with storage at 4° C., 25° C. and 37° C. for up to 12 months. The particle size was also stable with storage at 4° C. for up to 12 months. However, a minor increase in particle size was observed for product stored at 25° C. for 12 months, while a large increase in particle size (about 6×) was evident for samples stored at 37° C. for 12 months. However, in vitro biological activity (human B-cell IL-6 production) was unchanged after 12 months storage at any temperature. It was concluded that the lyophilized formulation is sufficiently stable for at least 12 months at 25° C.

Although the D56-05 solution formulation is stable at frozen (−80° C.) and refrigerated (5° C.) storage conditions, the D56-05 lyophilized formulation displayed enhanced stability compared with D56-05 in solution, especially at higher storage temperatures of 25° C. and 37° C.

Example S12: Preparation of [Maleimide-PEG$_6$]$_y$-FICOLL with Different Maleimide:FICOLL Molar Ratios (y), and Impact on D56-01:FICOLL Molar Ratio (x) in Purified D56-05 (aka [(D56-01)-PEG$_6$]$_x$-FICOLL)

[Maleimide-PEG$_6$]$_y$-FICOLL lots with different maleimide:FICOLL molar ratios (y) were produced from (AECM)$_z$-FICOLL (amine:FICOLL molar ratio (z)=224) using the procedure described in Example S3, Section E except at smaller scale and using different amounts of SM-PEG$_6$ (0.25, 0.5, 0.75, 1.0, & 2.0 equivalents per amine). The maleimide:FICOLL molar ratios (y) were determined by the procedures described in Examples S4 and S6. The results in Table S12-1 show that adding different amounts of SM-PEG$_6$ resulted in [Maleimide-PEG$_6$]$_y$-FICOLL lots with maleimide:FICOLL molar ratios (y) from 8 to 185. The [Maleimide-PEG$_6$]$_y$-FICOLL lots were then reacted with D56-03 (1.1 equivalent per maleimide) and the resulting D56-05 lots were purified as described in Example S3, Section G. The D56-01:FICOLL molar ratios (x) of the D56-05 (aka [(D56-01)-PEG$_6$]$_x$-FICOLL) lots were determined as described in Examples S4 and S7, and ranged from 24-154 (Table S12-1). These results show that the D56-01 loading in D56-05 can be controlled by the amount of SM-PEG$_6$ used in the preparation of [Maleimide-PEG$_6$]$_y$-FICOLL. See Example B9 for the in vitro potency of these compounds.

Example S13: Preparation of D56-25, D56-26 and D56-27 (aka [(D56-01)-PEG$_n$]$_x$-FICOLL) Using SM-PEG$_n$ Linkers with n=24, 45, and 70, Respectively

[Maleimide-PEG$_n$]$_y$-FICOLL lots with different PEG linker lengths were produced from (AECM)$_z$-FICOLL (amine:FICOLL molar ratio (z)=224) using the procedure described in Example S3, Section E, except at smaller scale and using SM-PEG$_n$ linkers with n=24, 45, and 70, respectively (see FIG. 5 for chemical structures of SM-PEG). The SM-PEG$_{24}$ reagent used was obtained from Thermo Fisher (Rockford, Ill.), which has the structure as shown in FIG. 5-A where n is 24. The SM-PEG$_{45}$ and SM-PEG$_{70}$ reagents used were obtained from Nanocs Inc., (New York, N.Y.); and the structures are as shown in FIG. 5-B (n is 45 and 70 respectively). The maleimide:FICOLL molar ratios (y) of the resulting [Maleimide-PEG$_n$]$_y$-FICOLL lots were determined as described in Examples S4 and S6 and the results are shown in Table S13-1. The maleimide:FICOLL molar ratios (y) ranged from 199 to 227, showing that the PEG linker length did not significantly affect the maleimide:FICOLL molar ratios obtained.

D56-25, D56-26 and D56-27 (aka [(D56-01)-PEG$_n$]$_x$-FICOLL with n=24, 45 and 70, respectively) were prepared from the three [Maleimide-PEG$_n$]$_y$-FICOLL lots as described in Example S3, Section G except on a smaller scale. The D56-01:FICOLL molar ratios (x) of the [(D56-01)-PEG$_n$]$_x$-FICOLL lots (D56-05 (n=6), D56-25 (n=24), D56-26 (n=45) and D56-27 (n=70)) were determined as described in Examples S4 and S7 and the mean particle diameter was determined as described in Example S8. The D56-01:FICOLL molar ratios (x) ranged from 108 to 116 (Table S13-1), showing that the PEG linker length did not significantly affect the D56-01:FICOLL molar ratios obtained. However, there was an increase in mean particle diameter (from 55 nm to 91 nm) that correlated with increase length of the PEG linker (Table S13-1). See Example B10 for the in vitro potency of these compounds.

TABLE S13-1

Effects of SM-PEG$_n$ Linker Length on [(D56-01)-PEG$_n$]$_x$-FICOLL Properties

|  | D56-05 | D56-25 | D56-26 | D56-27 |
|---|---|---|---|---|
| PEG$_n$ length (n) | 6 | 24 | 45 | 70 |
| Maleimide:FICOLL molar ratio (y) in [Maleimide-PEG$_n$]$_y$-FICOLL | 215 | 199 | 227 | 225 |
| D56-01:FICOLL molar ratio (x) in [(D56-01)-PEG$_n$]$_x$-FICOLL | 109 | 116 | 110 | 108 |

TABLE S12-1

Summary of Preparation of [Maleimide-PEG$_6$]$_y$-FICOLL Lots with Different Maleimide:FICOLL Ratios (y), and Effect on D56-01 Molar Ratios (x) in D56-05 (aka [(D56-01)-PEG$_6$]$_x$-FICOLL)

|  | Test 1 | Test 2 | Test 3 | Test 4 | Test 5 | Test 6 |
|---|---|---|---|---|---|---|
| Equivalents SM-PEG$_6$ per amine | 0.25 | 0.5 | 0.75 | 1.0 | 1.5 | 2.0 |
| Maleimide:FICOLL ratio (y) in [Maleimide-PEG$_6$]$_y$-FICOLL | 8 | 28 | 61 | 101 | 176 | 185 |
| Equivalents of D56-03 per maleimide in [Maleimide-PEG$_6$]$_y$-FICOLL | ND | 1.1 | 1.1 | 1.1 | 0.75 | 1.1 |
| D56-01:FICOLL molar ratio (x) in D56-05 (aka [(D56-01)-PEG$_6$]$_x$-FICOLL) | ND | 24 | 53 | 82 | 124 | 154 |

ND = Not done.

TABLE S13-1-continued

Effects of SM-PEG$_n$ Linker Length on [(D56-01)-PEG$_n$]$_x$-FICOLL Properties

|  | D56-05 | D56-25 | D56-26 | D56-27 |
|---|---|---|---|---|
| Purity | >99% | >99% | >99% | >99% |
| Mean particle diameter (nm)[a] | 55 nm | 77 nm | 78 nm | 91 nm |

[a]Mean particle diameter was determined as described in Example S8.

Example S14: Preparation of [Maleimide-MC]$_y$-FICOLL

[Maleimide-MC]$_y$-FICOLL was manufactured from [AECM]$_z$-FICOLL using the sulfo-SMCC linker as described U.S. Pat. No. 8,597,665. [Maleimide-MC]$_y$-FICOLL showed solubility problems in aqueous buffers, observed as oiling out and/or precipitation. The difficulty in handling the Maleimide-MC-FICOLL made conjugation reactions with thiol-activated polynucleotide (PN) or chimeric compound (CC) inconsistent.

Example S15: Preparation of Alexa Fluor® 555-(D56-05) (aka Alexa Fluor® 555/[(D56-01)-PEG$_6$]$_x$-FICOLL)

The amine reactive derivative of Alexa Fluor® 555 (Alexa Fluor® 555-NHS ester) was purchased from Life Technologies (Foster City, Calif.). AECM-FICOLL, prepared as described in Example S3, was activated by reaction with a mixture of Alexa Fluor® 555-NHS Ester and SM-PEG$_6$ to form Alexa Fluor® 555/[Maleimide-PEG$_6$]$_y$-FICOLL which was reacted with D56-03 (aka (D56-01)-3'-SH) as described in Example S3 to yield Alexa Fluor® 555-(D56-05) (aka Alexa Fluor® 555/[(D56-01)-PEG$_6$]$_x$-FICOLL).

Example S16: Preparation of D56-08, D56-09, D56-12 and D56-13

D56-08, D56-09, D56-12 and D56-13 are prepared as described in U.S. Pat. No. 8,597,665.

Example S17: Preparation of Alexa Fluor® 647-(D56-05) (aka Alexa Fluor® 647/[(D56-01)-PEG$_6$]$_x$-FICOLL)

Fluor 647-NHS ester (Life Technologies) was reacted with rPA to yield Alexa Fluor® 647/rPA with a resulting ratio of one Alexa Fluor® 647 per rPA.

Biological Examples

Example B1: Isolation and Stimulation of Human Leukocytes

Activity of polynucleotides (PN) and chimeric compounds (CC) were assessed in vitro by measurement of cytokine secretion by human peripheral blood mononuclear cells (PBMC) and isolated B cells, as well as by measurement of B cell proliferation. Cytokine levels secreted into cell culture media were measured by enzyme-linked immunosorbent assay (ELISA).

Human blood was obtained with informed consent from healthy human donors. PBMC were isolated by FICOLL-Paque (GE Healthcare, UK) density gradient centrifugation. Human B cells were isolated by positive selection with anti-CD19 microbeads (Miltenyi Biotec, Auburn, Calif.). Human plasmacytoid dendritic cells (pDCs) were isolated by positive selection with anti-BDCA-2 microbeads (Miltenyi Biotec, Auburn, Calif.). Isolated pDC were added back into a pool of total PBMC to result in final pDC concentrations in total PBMC varying from 0.5 to 2.4% by donor.

Cells were resuspended in RPMI-1640 (BioWhittaker, Walkersville, Md.) supplemented with 10% heat-inactivated fetal bovine serum (FBS) (Gemini, West Sacramento, Calif.) plus 50 U/ml penicillin, 50 µg/ml streptomycin, 2 mM L-glutamine, 10 mM 4-(2-hydroxyethyl)-1-piperazineethanesulfonic acid (HEPES) buffer and 1 mM sodium pyruvate (BioWhittaker, Walkersville, Md.). For B cell stimulation, cells were cultured at $0.75 \times 10^6$ per mL in 96-well round-bottomed plates in duplicate with PN or CC at a concentration range of 5.5-0.0054 µM for 90-93 h. For PBMC and pDC-enriched PBMC stimulation, cells were cultured at $2.5 \times 10^6$ per mL in 96-well flat-bottomed plates in triplicate with PN or CC at a concentration range of 2.5-0.0012 µM for 21-24 h.

ELISA assays. IL-6 and IFN-α levels were assayed using commercially available antibody pairs (MabTech, Inc. Cincinnati, Ohio); the limit of minimal detection was 31 pg/mL for IL-6 and 23 pg/mL for IFN-α. 96-well Maxisorp Immuno plates were coated with cytokine specific Ab and then blocked with 1% BSA in DPBS. Cell culture samples were added and bound cytokine was detected by addition of biotin-labeled secondary antibody, followed by horse radish peroxidase and a peroxidase-specific colorimetric substrate. Standard curves were generated using recombinant cytokines purchased from R&D Systems (Minneapolis, Minn.) for IL-6 and MabTech for IFN-α. Absorbance values were determined at 450 nm with background subtraction at 650 nm using either a SpectraMax 190 or VersaMax microplate reader (Molecular Devices Corporation, Sunnyvale, Calif.). Half-maximal effective concentrations (EC$_{50}$) values were calculated from each individual donor by interpolation with a cumulative average for all donors tabulated. The EC$_{50}$ was defined as the PN or CC concentration giving a value equal to half the maximum cytokine level.

Example B2: Isolation and Stimulation of Mouse Splenocytes

Activity of polynucleotides (PN) and chimeric compounds (CC) were assessed in vitro by measurement of cytokine secretion by mouse splenocytes. Cytokine levels secreted into cell culture media were measured by enzyme-linked immunosorbent assay (ELISA).

Spleens of 8 to 20 week-old BALB/c mice were harvested and the splenocytes isolated using standard teasing apart and treatment with ACK lysing buffer (BioWhittaker, Inc. Walkersville, Md.). Four spleens were pooled in the experiments. Cells were re-suspended in RPMI-1640 supplemented with 10% heat-inactivated fetal bovine serum (FBS) plus 50 µM 2-mercaptoethanol, 50 U/ml penicillin, 50 µg/ml streptomycin, 2 mM L-glutamine, 10 mM HEPES and 1 mM sodium pyruvate. For stimulation, splenocytes were cultured at $3.5 \times 10^6$ cells per mL in 96-well flat-bottomed plates in triplicate with PN or CC at a concentration range of 22-0.0003 µM for 20-24 h.

ELISA assays. IL-6 and IL-12p40 levels were assayed using commercially available antibody pairs (BD Biosciences, San Jose, Calif.); the limit of minimal detection was 31 pg/mL for IL-6 and 63 pg/ml for IL-12p40. 96-well Maxisorp Immuno plates were coated with cytokine specific Ab and then blocked with 1% BSA in DPBS. Culture supernatants were added and bound cytokine was detected by addition of biotin-labeled secondary antibody, followed by HRP and a peroxidase-specific colorimetric substrate. Standard curves were generated using recombinant cytokines purchased from BD Biosciences. Absorbance values were determined at 450 nm with background subtraction at 650 nm using either a SpectraMax 190 or VersaMax microplate reader (Molecular Devices Corporation, Sunnyvale, Calif.). The $EC_{50}$ was defined as the concentration of PN or CC giving a value equal to half the maximum cytokine level. $EC_{50}$ values for IL-6 and IL-12p40 were determined using a sigmoidal-dose response curve fit of X=Log(X) transformed data using GraphPad Prism software.

Example B3: Linear Chimeric Compound (CC) Sequence Optimization

Two separate experiments were conducted. In the following tables the mean refers to the geometric mean.

A. Experiment 1. Linear CC D56-14 was previously shown to induce IFN-α from human PBMC, IL-6 from human B cells and to stimulate mouse splenocytes (U.S. Pat. No. 8,597,665). Sequence optimization was performed to determine if the IFN-α activity could be improved relative to D56-14. Seven new linear CC were tested in primary screening assays, i.e., human PBMC IFN-α activity, and human B cell IL-6 activity (see Example B1 for procedures). The general structure of the linear CCs used in this example, $N_1$—$S_1$—$N_2$—$S_2$—$N_3$, can be used to describe the placement of the nucleic acid motifs (N) within the CC. Six of the new CC in this study all contained the mouse motif, 5-AACGTTC-3', in the $N_3$ position. D56-24 contained the mouse motif in the $N_2$ position, and was included in the screening to explore a different positioning of the mouse activity motif in the linear CC context. D56-10 is a known CpG-B immunostimulatory sequence (ISS) and was included in the panel as a positive control.

TABLE B3-1

Experiment 1 CC Panel Human PBMC IFN-alpha Response EC50 (mM)

| Donor # | D56-10 | D56-14 | C56-15 | D56-16 | D56-18 | D56-19 | D56-21 | D56-22 | D56-24 |
|---|---|---|---|---|---|---|---|---|---|
| Do 1 | NC | 0.061 | 0.057 | 0.045 | 0.047 | 0.104 | ND | ND | ND |
| Do 2 | NC | 0.102 | 0.109 | 0.058 | 0.104 | 0.105 | ND | ND | ND |
| Do 3 | NC | 0.072 | 0.068 | 0.054 | 0.059 | 0.078 | 0.112 | 0.067 | 0.029 |
| Do 4 | NC | 0.071 | 0.094 | 0.065 | 0.085 | 0.095 | 0.142 | 0.070 | 0.051 |
| Do 5 | NC | 0.055 | 0.110 | 0.096 | 0.056 | 0.121 | 0.227 | 0.053 | 0.042 |
| Do 6 | NC | 0.068 | 0.079 | 0.059 | 0.077 | 0.145 | 0.187 | 0.056 | 0.050 |
| Do 7 | NC | ND | 0.129 | 0.096 | ND | 0.125 | 0.377 | 0.122 | 0.081 |
| Do 8 | NC | 0.056 | 0.112 | 0.059 | 0.100 | 0.109 | 0.333 | 0.093 | 0.052 |
| Ave | NC | 0.069 | 0.095 | 0.066 | 0.076 | 0.110 | 0.230 | 0.077 | 0.051 |
| SD | NC | 0.016 | 0.025 | 0.019 | 0.022 | 0.021 | 0.106 | 0.026 | 0.017 |
| Count | 0 | 7 | 8 | 8 | 7 | 8 | 6 | 6 | 6 |
| SEM | NC | 0.006 | 0.009 | 0.007 | 0.008 | 0.007 | 0.043 | 0.011 | 0.007 |
| Mean | NC | 0.068 | 0.092 | 0.064 | 0.073 | 0.109 | 0.210 | 0.074 | 0.048 |

NC = not calculable from dose response curve;
ND = not determined for specified donors

TABLE B3-2

Experiment 1 CC Panel Human B Cell IL-6 Response EC50 (mM)

| Donor # | D56-10 | D56-14 | C56-15 | D56-16 | D56-18 | D56-19 | D56-21 | D56-22 | D56-24 |
|---|---|---|---|---|---|---|---|---|---|
| Do 9 | 0.101 | 0.126 | 0.270 | 0.075 | 0.264 | ND | ND | ND | ND |
| Do 10 | 0.097 | 0.053 | 0.119 | 0.052 | 0.154 | 0.128 | 0.235 | 0.044 | 0.056 |
| Do 11 | NC | 0.068 | 0.144 | 0.078 | 0.159 | 0.146 | 0.341 | 0.066 | ND |
| Do 12 | 0.048 | 0.048 | 0.078 | 0.066 | ND | ND | ND | ND | ND |
| Do 13 | ND | 0.056 | ND | 0.056 | 0.148 | 0.137 | 0.407 | 0.047 | 0.059 |
| Do 14 | 0.052 | 0.053 | 0.072 | 0.051 | 0.156 | 0.075 | 0.256 | 0.050 | 0.059 |
| Do 15 | 0.120 | 0.081 | 0.183 | 0.056 | 0.213 | 0.184 | 0.747 | ND | ND |
| Do 16 | 0.084 | 0.128 | 0.217 | 0.116 | 0.219 | ND | ND | ND | ND |
| Do 17 | 0.075 | 0.066 | 0.217 | 0.064 | 0.171 | 0.144 | 0.303 | 0.057 | 0.052 |
| Ave | 0.082 | 0.075 | 0.162 | 0.068 | 0.185 | 0.136 | 0.382 | 0.053 | 0.057 |
| SD | 0.026 | 0.031 | 0.071 | 0.020 | 0.042 | 0.035 | 0.189 | 0.009 | 0.003 |
| Count | 7 | 9 | 8 | 9 | 8 | 6 | 6 | 5 | 4 |
| SEM | 0.010 | 0.010 | 0.025 | 0.007 | 0.015 | 0.014 | 0.077 | 0.004 | 0.002 |
| Mean | 0.079 | 0.071 | 0.147 | 0.066 | 0.182 | 0.131 | 0.352 | 0.052 | 0.056 |

NC = not calculable from dose response curve;
ND = not determined

Linear CC D56-16, D56-18, D56-19, and D56-22 and D56-24 showed similar or improved PBMC IFN-α activity (Table B3-1), and similar or slightly reduced human B cell activity (Table B3-2) compared to D56-14. Linear CC D56-24 showed the best PBMC IFN-α and human B cell activity of sequences tested. As noted above, the principal difference between D56-24 and the other sequences is that $N_2$ and $N_3$ human and mouse motifs, respectively, are switched in D56-24 such that the mouse motif is located in the $N_2$ position as compared to the $N_3$ position in the other new CC.

B. Experiment 2. Based on results from Experiment 1, a new panel of CC sequences was designed with the goal of increasing human and mouse activity. Specifically, four new sequences related to D56-16, D56-18, D56-19, and D56-22 were designed with the mouse motif moved to the $N_2$ position: D56-17, D56-01, D56-20, and D56-23. The initial in vitro screening of the new CCs was performed on mouse splenocytes (Table B3-3 and Table B3-4). All sequences with the mouse motif in the $N_2$ position showed strongly improved IL-6 and IL-12p40 potency compared to the corresponding CCs with the mouse motif in the $N_3$ position. D56-01 and D56-23 showed the best IL-6 potency of the CCs tested while D56-01 had the best IL-12p40 potency.

TABLE B3-3

Experiment 2 CC Panel Mouse Splenocyte IL-6 Response EC50 (mM)

| Exp # | D56-10 | D56-14 | D56-24 | D56-16 | D56-17 | D56-18 | D56-01 | D56-19 | D56-20 | D56-22 | D56-23 |
|---|---|---|---|---|---|---|---|---|---|---|---|
| 426 | 0.046 | 0.071 | 0.031 | 1.293 | 0.032 | 2.359 | 0.026 | 8.784 | 0.042 | 1.009 | 0.025 |
| 433 | 0.039 | 0.048 | 0.025 | 0.725 | 0.018 | 2.942 | 0.017 | 5.942 | 0.026 | 1.422 | 0.012 |
| Ave | 0.042 | 0.060 | 0.028 | 1.009 | 0.025 | 2.651 | 0.021 | 7.363 | 0.034 | 1.216 | 0.019 |
| SD | 0.005 | 0.016 | 0.004 | 0.402 | 0.010 | 0.412 | 0.006 | 2.010 | 0.011 | 0.292 | 0.009 |
| Count | 2 | 2 | 2 | 2 | 2 | 2 | 2 | 2 | 2 | 2 | 2 |
| SEM | 0.004 | 0.011 | 0.003 | 0.284 | 0.007 | 0.292 | 0.005 | 1.421 | 0.008 | 0.207 | 0.006 |
| Mean | 0.042 | 0.059 | 0.028 | 0.968 | 0.024 | 2.634 | 0.021 | 7.225 | 0.033 | 1.198 | 0.017 |

TABLE B3-4

Experiment 2 CC Panel Mouse Splenocyte IL-12p40 Response EC50 (mM)

| Exp # | D56-10 | D56-14 | D56-24 | D56-16 | D56-17 | D56-18 | D56-01 | D56-19 | D56-20 | D56-22 | D56-23 |
|---|---|---|---|---|---|---|---|---|---|---|---|
| 426 | 0.078 | 0.821 | 0.341 | 1.369 | 0.339 | 1.225 | 0.250 | 1.190 | 1.106 | 0.421 | 0.335 |
| 433 | 0.062 | 0.906 | 1.256 | 3.298 | 0.995 | 2.138 | 0.091 | 4.507 | 2.901 | 3.229 | 2.410 |
| Ave | 0.070 | 0.864 | 0.798 | 2.334 | 0.667 | 1.682 | 0.170 | 2.849 | 2.003 | 1.825 | 1.372 |
| SD | 0.011 | 0.060 | 0.647 | 1.364 | 0.464 | 0.645 | 0.113 | 2.346 | 1.269 | 1.985 | 1.467 |
| Count | 2 | 2 | 2 | 2 | 2 | 2 | 2 | 2 | 2 | 2 | 2 |
| SEM | 0.008 | 0.043 | 0.458 | 0.964 | 0.328 | 0.456 | 0.080 | 1.659 | 0.897 | 1.404 | 1.038 |
| Mean | 0.070 | 0.862 | 0.654 | 2.125 | 0.581 | 1.619 | 0.151 | 2.316 | 1.791 | 1.166 | 0.898 |

Results for the human PBMC IFN-α activity and human B cell IL-6 activity are shown in Table B3-5 and Table B3-6, respectively. Surprisingly, having the mouse motif in $N_2$ position also significantly improved the human PBMC IFN-α potency. In general, the human IL-6 potency was also improved for the CC with the mouse motif in the $N_2$ position.

Of the in vitro tests performed, IFN-α potency is considered the most predictive of good in vivo activity in cancer, antiviral, asthma, and allergy models. Based on this, D56-01, D56-17, D56-20, D56-23, and D56-24 were considered the lead candidates. These sequences also showed good human B cell IL-6 and mouse IL-6 activity. Surprisingly, D56-01 has significantly improved IL12p40 potency compared to the other $N_2$ mouse motif sequences.

TABLE B3-5

Experiment 2 CC Panel Human PBMC IFN-α Response EC50 (mM)

| Donor # | D56-10 | D56-14 | D56-24 | D56-16 | D56-17 | D56-18 | D56-01 | D56-19 | D56-20 | D56-22 | D56-23 |
|---|---|---|---|---|---|---|---|---|---|---|---|
| Do 1 | ND | 0.044 | 0.029 | 0.031 | 0.049 | 0.055 | 0.038 | 0.071 | 0.037 | 0.061 | 0.218 |
| Do 2 | ND | 0.052 | 0.040 | 0.029 | 0.021 | 0.094 | 0.039 | 0.091 | 0.029 | 0.053 | 0.024 |
| Do 3 | 0.373 | 0.096 | 0.028 | 0.033 | 0.050 | 0.066 | 0.048 | 0.117 | 0.101 | 0.054 | ND |
| Do 4 | ND | 0.059 | 0.048 | 0.045 | 0.045 | 0.064 | 0.036 | 0.068 | 0.033 | 0.081 | ND |
| Do 5 | ND | 0.124 | 0.020 | 0.104 | 0.045 | 0.094 | 0.092 | 0.143 | 0.061 | 0.106 | ND |

TABLE B3-5-continued

Experiment 2 CC Panel Human PBMC IFN-α Response EC50 (mM)

| Donor # | D56-10 | D56-14 | D56-24 | D56-16 | D56-17 | D56-18 | D56-01 | D56-19 | D56-20 | D56-22 | D56-23 |
|---|---|---|---|---|---|---|---|---|---|---|---|
| Do 6 | 0.054 | 0.044 | 0.033 | 0.059 | 0.041 | 0.097 | 0.035 | 0.063 | 0.038 | 0.067 | 0.048 |
| Do 7 | ND | 0.055 | 0.036 | 0.054 | 0.027 | 0.067 | 0.028 | 0.099 | 0.030 | 0.060 | 0.018 |
| Do 8 | ND | 0.100 | 0.051 | 0.105 | 0.045 | 0.099 | 0.057 | 0.147 | 0.069 | 0.122 | ND |
| Ave | 0.213 | 0.072 | 0.036 | 0.058 | 0.040 | 0.080 | 0.047 | 0.100 | 0.050 | 0.075 | 0.077 |
| SD | 0.226 | 0.030 | 0.010 | 0.031 | 0.011 | 0.018 | 0.020 | 0.033 | 0.025 | 0.026 | 0.095 |
| Count | 2 | 8 | 8 | 8 | 8 | 8 | 8 | 8 | 8 | 8 | 4 |
| SEM | 0.160 | 0.011 | 0.004 | 0.011 | 0.004 | 0.006 | 0.007 | 0.012 | 0.009 | 0.009 | 0.048 |
| Mean | 0.142 | 0.067 | 0.034 | 0.051 | 0.039 | 0.078 | 0.044 | 0.095 | 0.045 | 0.072 | 0.046 |

ND = not determined

TABLE B3-6

Experiment 2 CC Panel Human B Cell IL-6 Response EC50 (mM)

| Donor | D56-10 | D56-14 | D56-24 | D56-16 | D56-17 | D56-18 | D56-01 | D56-19 | D56-20 | D56-22 | D56-23 |
|---|---|---|---|---|---|---|---|---|---|---|---|
| Do 9 | 0.054 | 0.065 | 0.044 | 0.049 | 0.028 | 0.173 | 0.053 | 0.090 | 0.048 | 0.041 | 0.024 |
| Do 10 | 0.066 | 0.063 | 0.045 | 0.043 | 0.035 | 0.137 | 0.021 | 0.096 | 0.017 | 0.045 | 0.018 |
| Do 11 | 0.062 | 0.056 | 0.039 | 0.047 | 0.034 | 0.149 | 0.050 | 0.128 | 0.041 | 0.045 | 0.027 |
| Do 12 | 0.069 | 0.066 | 0.052 | 0.057 | 0.040 | 0.170 | 0.052 | 0.122 | 0.033 | 0.048 | 0.029 |
| Ave | 0.063 | 0.063 | 0.045 | 0.049 | 0.034 | 0.157 | 0.044 | 0.109 | 0.034 | 0.045 | 0.025 |
| SD | 0.006 | 0.005 | 0.005 | 0.006 | 0.005 | 0.017 | 0.015 | 0.019 | 0.013 | 0.003 | 0.005 |
| Count | 4 | 4 | 4 | 4 | 4 | 4 | 4 | 4 | 4 | 4 | 4 |
| SEM | 0.003 | 0.002 | 0.003 | 0.003 | 0.002 | 0.009 | 0.008 | 0.009 | 0.007 | 0.001 | 0.002 |
| Mean | 0.063 | 0.063 | 0.045 | 0.048 | 0.034 | 0.157 | 0.041 | 0.108 | 0.032 | 0.045 | 0.024 |

Example B4: D56-05 Induces More Potent In Vitro Responses than D56-01

Based on potency of induction of both human and mouse cytokines, D56-01 was chosen as a lead candidate to develop in a nanoparticle formulation. The D56-01 sequence was conjugated to FICOLL as described in Example S3 to generate D56-05 (aka [(D56-01)-PEG$_6$]$_x$-FICOLL). D56-01 and D56-05 were then compared for relative in vitro potency for induction of human PBMC IFN-α and human B cell IL-6. Results for the human PBMC IFN-α activity and human B cell IL-6 activity are shown in Table B4-1 and Table B4-2, respectively. The sequences D56-10 and D56-14 were used as historical positive controls in this experiment.

The nanoparticle formulation D56-05 was strikingly more potent in induction of both IFN-α (Table B4-1) and IL-6 activity (Table B4-2).

TABLE B4-1

Human PBMC IFN-α Responses to D56-01 and D56-05 EC50 (mM)

| Donor # | D56-10 | D56-14 | D56-01 | D56-05 |
|---|---|---|---|---|
| Do 1 | NC | NC | NC | 0.024 |
| Do 2 | 0.109 | 0.077 | 0.063 | 0.016 |
| Do 3 | 0.319 | NC | 0.057 | 0.007 |
| Do 4 | 0.198 | 0.070 | 0.050 | ND |
| Do 5 | 0.090 | 0.065 | 0.053 | 0.025 |
| Do 6 | 0.187 | 0.081 | 0.033 | 0.005 |
| Do 7 | NC | 0.091 | 0.052 | 0.007 |
| Do 8 | 0.122 | 0.052 | 0.045 | 0.007 |
| Do 9 | NC | 0.053 | 0.054 | 0.007 |
| Do 10 | 0.082 | 0.068 | 0.057 | 0.019 |
| Do 11 | ND | 0.050 | 0.042 | NC |
| Do 12 | ND | 0.058 | 0.038 | 0.027 |
| Do 13 | ND | 0.057 | 0.037 | 0.031 |
| Do 14 | ND | 0.060 | 0.050 | 0.007 |
| Do 15 | ND | 0.057 | 0.053 | 0.010 |
| Do 16 | ND | NC | 0.026 | 0.003 |
| Ave | 0.158 | 0.064 | 0.047 | 0.014 |
| SD | 0.084 | 0.013 | 0.010 | 0.010 |
| Count | 7 | 13 | 15 | 14 |
| SEM | 0.032 | 0.003 | 0.003 | 0.003 |
| GeoMean | 0.142 | 0.063 | 0.046 | 0.011 |

NC = not calculable from dose response curve;
ND = not determined

TABLE B4-2

Human B Cell IL-6 Responses to D56-01 and D56-05 EC50 (mM)

| Donor # | D56-10 | D56-14 | D56-01 | D56-05 |
|---|---|---|---|---|
| Do 17 | 0.067 | 0.074 | 0.076 | 0.019 |
| Do 18 | 0.078 | 0.072 | 0.065 | 0.015 |
| Do 19 | 0.078 | 0.080 | 0.089 | 0.018 |
| Do 20 | 0.061 | 0.067 | 0.063 | 0.014 |
| Do 21 | ND | 0.077 | 0.069 | 0.020 |
| Do 22 | ND | 0.050 | 0.050 | 0.014 |
| Do 23 | ND | 0.051 | 0.054 | 0.011 |
| Do 24 | ND | 0.073 | 0.073 | 0.018 |
| Do 25 | ND | 0.057 | 0.061 | 0.013 |
| Ave | 0.071 | 0.074 | 0.072 | 0.017 |
| SD | 0.008 | 0.005 | 0.010 | 0.003 |
| Count | 4 | 5 | 5 | 5 |
| SEM | 0.004 | 0.002 | 0.005 | 0.001 |
| GeoMean | 0.071 | 0.074 | 0.072 | 0.017 |

ND = not determined

Example B5: D56-05 Induces More Potent In Vivo Responses than D56-01

Induction of innate immune responses following administration of D56-05 and D56-01 to mice and cynomologus monkeys was evaluated. In monkeys, interferon-pathway associated gene expression was measured in blood samples collected prior to and 24 hours post administration of D56-05 and D56-01. In mice, interferon-pathway and chemokine-associated gene expression were measured in injection-site draining lymph nodes harvested 18 hours post compound administration. Relative ability of antigen-presenting cell populations to acquire D56-05 and D56-01 was evaluated in injection site-draining lymph nodes harvested from mice 24 hours post compound injection. Additionally, maturation marker expression (CD69, CD86) was measured on plasmacytoid dendritic cells (pDCs) from lymph nodes harvested 20 hours post compound injection.

Cynomolgus monkeys (*Macaca fascicularis*) were housed at Valley Biosystems, (West Sacramento, Calif.) or at Battelle Biomedical Research Center (Columbus, Ohio), where all in life procedures were carried out. Only healthy adult animals were used in each study. Whole blood was collected in PAXgene tubes (QIAGEN, Venlo, NL) pre- and post-immunization and frozen for later extraction of RNA according to the manufacturer's instructions. Groups of 3 to 6 monkeys were immunized by the intramuscular route (quadriceps) with 10 µg anthrax recombinant Protective Antigen (rPA) from PharmAthene (Annapolis, Md.) alone or in combination with 1000, 250 or 50 µg D56-05 or 1000 or 250 µg D56-01 in 1 mL PBS.

For immunogenicity studies, groups of cynomolgus monkeys were immunized by either the i.m. (quadriceps) or s.c. route with rPA with/without doses of D56-01 or D56-05 in a total volume of 1 ml Dulbecco's PBS (DPBS) from BioWhittaker (Walkersville, Md.) with subsequent blood draws to assess effects of adjuvants on Ab responses.

Swiss Webster, BALB/c, and C57BL/6 mice (8-12 weeks of age) were purchased from Charles River Laboratoies (Hollister, Calif.) and housed at Pacific BioLabs (Hercules, Calif.) or Murigenics (Vallejo, Calif.), where all in life procedures were carried out. TLR9$^{-/-}$ mice were maintained at Simonsen Laboratories (Gilroy, Calif.) and used at 8-16 wk of age.

For immunogenicity, tissue distribution, and systemic toxicity studies, mice were injected in the quadriceps with adjuvant with/without rPA, or with rPA alone. For studies assessing muscle tissue responses, mice were injected bilaterally in the quadriceps with adjuvant alone. For draining lymph node responses, including gene expression and flow cytometry assessments, mice were injected in both rear footpads with adjuvant with/without rPA. D56-01-Alexa Fluor® 555, when used, was administered in combination with nonlabeled D56-01 in a ratio to match Alexa Fluor® 555/D56-05-specific relative fluorescence. All immunizations were performed in a total volume of 50 µL DPBS or 10 mM sodium phosphate buffer.

For gene expression analysis, mice were injected by the intramuscular or subcutaneous route (footpad) with DPBS or 10 µg D56-05 or D56-01. Muscle tissue and draining lymph nodes were harvested at 6 hours or 18 hours respectively, into RNAlater (QIAGEN, Venlo, The Netherlends) and frozen for later extraction of RNA according to the manufacturer's instructions. To quantify cellular uptake of compounds by flow cytometry, draining lymph nodes were harvested 24 hours after 25 µg fluorescently-labeled D56-01 or D56-05 was injected. Refer to Examples S2 and S15 for manufacture of Alexa Fluor® 555-(D56-01) and Alexa Fluor® 555-(D56-05), respectively. For analysis of cell surface markers using flow cytometry, draining lymph nodes were harvested 20 hours after injection of 5, 2, or 0.2 µg non-fluorescently-labeled D56-01 or D56-05. For flow cytometry experiments, single cell suspensions were prepared from treatment group pooled lymph nodes.

Organs were frozen in RNAlater (Qiagen, Venlo, The Netherlands). Total RNA was isolated from 30 mg per individual homogenized muscle using an RNeasy fibrous tissue mini kit (Qiagen) and entire homogenized popliteal lymph node using an RNeasy mini kit (Qiagen), both with on-column DNase I digestion.

Reverse Transcription-Polymerase Chain Reaction (RT-PCR). cDNA was prepared from total RNA samples using Recombinant RNasin Ribonuclease Inhibitor (Promega, Madison, Wis.), Oligo(dT)15 (Promega), Random Primers (Promega), dNTP (Invitrogen, Carlsbad, Calif.) and SuperScript III Reverse Transcriptase (Invitrogen). Quantification of mRNA was performed using Power SYBR Green master mix (Life Technologies). The cycling conditions were 15 min at 95° C., followed by 40 rounds of 15 sec at 95° C. and 1 min at 60° C., with analysis by an Applied Biosystems (Carlsbad, Calif.) StepOnePlus Real Time PCR system using StepOne v2.1 software. Ubiquitin was used as the reference gene. After PCR, Ct values were determined and normalized data were expressed as fold increase over pre-immunization or DPBS control. Alternately, RNA was reverse transcribed by an RT$^2$ First Strand Kit (Qiagen) for use with the RT$^2$ Profiler PCR array system (Qiagen) for cytokines and chemokines according to the manufacturer's directions.

Flow cytometry. Single-cell suspensions were prepared from mouse tissues and pooled by experimental group, excepting muscle, which was first digested with 2 mg/ml collagenase, type 2 (Worthington Biochemical Lakewood, N.J.) for 45 min at 37° C. Cells were stained for 30 min at 4° C. in DPBS containing 0.1% BSA with/without 2 mM EDTA after blocking FcgR with clone 2.4G2 mAb. Cells were fixed in a final concentration of 1% formaldehyde for a minimum of 20 min, followed by washing and resuspension in FACS flow buffer. Abs against CD3c (145-2C11), CD4 (GK1.5), CD8a (53-6.7), CD11b (M1/70), CD11c (HL3), CD19 (6D5), CD45R/B220 (RA3-6B2), CD49b (DX5), CD69 (H1.2F3), CD86 (GL-1), CD95 (Jo2), CD279 (J43), CD317/PDCA-1 (eBio927), CXCR5 (2G8), F4/80 (BM8), Ly-6C (AL-21), Ly-6G (1A8), MHC class II (MHC II; I-A/I-E) (M5/114.15.2), and T and B Cell activation Ag (GL7) were purchased from BD Biosciences (San Jose, Calif.), BioLegend (San Diego, Calif.), or eBioscience (San Diego, Calif.). Biotinylated peanut agglutinin (PNA) was purchased from Vector Laboratories (Burlingame, Calif.). Flow cytometry data were collected on an LSR II (BD Biosciences, San Jose, Calif.) flow cytometer and analyzed using FlowJo software (Tree Star, Ashland, Oreg.). Polychromatic imaging flow cytometry data were collected on an ImageStreamX mk II (Amnis, Seattle, Wash.) and analyzed using IDEAS v6.1 software. Images were captured using a 360 lens with a 0.9 numerical aperture and 2.5-mm effective depth of field. Cells likely to have colocalized fluorescent signals were identified with aid of bright detail similarity (BDS). BDS scoring quantifies colocalization between fluorescent markers within cells by comparing the spatial location and degree of overlap to calculate the non-mean-normalized Pearson correlation coefficient of the images. Events with BDS scores over the threshold level of 2 were likely to have fluorescence colocalization, which was confirmed visually. Lymph node cells were stained with antibodies to identify pDCs (CD3$^-$, CD19$^-$, CD49b$^-$, MHCII$^+$, CD11c$^+$, and B220$^+$ or PDCA-1$^+$), cDCs (MHCII$^+$, CD11b$^-$, CD11c$^+$), and mDCs (MHCII$^+$, CD11b$^+$, CD11c$^+$) and markers of cell maturation (CD69 and CD86). Primary gating was through light scatter, doublet exclusion and lymphocyte lineage exclusion gating. Extent of fluorescently-labeled D56-05 and D56-01 uptake on pDCs, cDCs, and mDCs and, in a separate experiment, maturation marker expression on pDCs (geometric mean fluorescence intensity; gMFI) was determined using FlowJo software (TreeStar, Ashland, Oreg.).

Statistical analysis. A Mann-Whitney or Kruskal-Wallis test with a Dunn posttest, as specified in the brief description of the drawings, was used to determine statistical significance. A p value less than or equal to 0.05 was considered significant.

Results. Table B5-1 shows IFN pathway-associated gene expression in monkey blood (fold increase over pre-immunization). These data indicate that while D56-01 induced IFN-associated gene expression, D56-05 induced more intensive IFN-associated gene expression following immunization with rPA in primates.

To assess early D56-05 effects in local tissue that may be associated with improved adjuvant activity compared with monomeric D56-01, transcriptional changes were analyzed in injection site muscle 6 hours after injection. Mice were injected with adjuvants, without rPA, at equivalent CpG-based doses, with PBS-injected animals serving as controls. D56-05 exhibited a more potent effect on both the number of genes induced and the level of gene induction compared with the effect of monomeric D56-01, both for multiple IFN-regulated genes (IRGs) (FIG. 11A) and chemokines (FIG. 11B). Likewise, D56-05 induced higher levels of cytokines of the IL-1 and TNF superfamilies (FIG. 11C). Adhesion molecules, integrins, and matrix metalloproteinases were also induced to a much greater degree in injection site muscle following D56-05 treatment (FIG. 11D). Thus, D56-01 in a nanoparticle-like formulation is more efficient at inducing early markers of immune activation at the injection site compared with monomeric D56-01. To determine whether nanoparticulate and monomeric D56-01 differentially affected cellular recruitment to injection site muscle, relative proportions of immune cell populations were analyzed by flow cytometry. At 24 h, total CD45+ cells were 3-fold as abundant in D56-05-injected muscle compared with D56-01-injected tissue (about 212,000 versus about 67,000 cells/g muscle). D56-05 injection induced relatively higher proportions of conventional DCs (cDCs), myeloid DCs (mDCs), myeloid cells, macrophages, monocytes, and neutrophils in the injected muscle compared with mice administered monomeric D56-01 (FIG. 11E).

To test whether D56-05-induced inflammatory gene expression and adjuvanticity for rPA-induced Ab responses involved TLR9-independent pathways, responses were tested in $TLR9^{-/-}$ mice. Following i.m. injection with D56-05, induction of IRGs and chemokine and cytokine genes was observed in wildtype C57BL/6 mice, but not in $TLR9^{-/-}$ mice (FIG. 12A). Consequently, no D56-05 adjuvant activity was observed in $TLR9^{-/-}$ mice (FIG. 12B). The lack of both inflammatory responses induced at the injection site and adjuvant effects in $TLR9^{-/-}$ mice demonstrated that the activity of D56-05 is dependent on TLR9 signaling.

18 hours after s.c. injection, D56-05 produced greater increases in transcription of interferon-regulated genes (FIG. 13A), chemokines (FIG. 13B), and cytokines (FIG. 13C) in lymph nodes compared with D56-05. As a likely consequence of stronger induction of multiple chemokines, D56-05 injection resulted in greater numbers of various antigen presenting cell (APC) populations in the draining lymph node compared with D56-01-injected mice. MHC II+ pDCs were especially affected, with 5-fold greater numbers present (mean, 940 versus 187 cells/lymph node) following D56-05 treatment (FIG. 14). Taken together, these data demonstrate that D56-05 is more potent than monomeric D56-01 for initiating immune responses at the injection site and in draining lymph nodes.

Whether relative increases in cellular trafficking following D56-05 treatment were accompanied by differential effects on cellular uptake of the adjuvant were determined. A wide range of cell populations involved in the initiation of adaptive immune response, including MHC II+ pDCs and mDCs, myeloid cells, macrophages, and monocytes, as well as neutrophils, all demonstrated greater fluorescence following injection with D56-05. There were substantial proportions of mDCs, myeloid cells, macrophages, and monocytes with high levels of Alexa Fluor® 555 fluorescence in D56-05-injected mice, whereas only mDCs internalized D56-01 to a similar extent. Lymphocyte uptake of either Alexa Fluor® 555-labeled D56-01-Ficoll or D56-01 was negligible. Table B5-2 shows uptake of fluorescently-labeled D56-05 or D56-01 as measured by geometric Mean Fluorescence Intensity (gMFI) of A555-labeled D56-05 or D56-01 in cells. These data indicate that draining lymph node pDC, cDCs, and mDCs take up D56-05 or D56-01 following in vivo injection in mice. In general, uptake of D56-05 was greater than uptake of D56-01 in the different cell populations as indicated by higher gMFI values.

D56-05 also exerted a greater effect on the activation state of APCs and lymphocytes than did monomeric D56-01 within the draining lymph nodes. Following D56-05 injection, pDCs, CD8+ DCs, cDCs, mDCs, and myeloid cells all displayed greater expression of CD86, whereas B and NK cells displayed greater expression of CD69 compared with lymph node cells harvested from mice injected with monomeric D56-01. Table B5-3 displays levels of CD69 and CD86 expression on pDCs from mouse lymph nodes. These data indicate that both D56-05 and D56-01 induce CD69 and CD86 expression on pDCs but D56-05 is more potent in inducing maturation of pDCs in vivo as compared to D56-01. Thus, nanoparticulate formulation of D56-01 on Ficoll substantially improves its uptake by and activation of key APC populations, contributing to the effective induction of adaptive immunity.

To determine whether Ficoll conjugation increased the efficiency of CpG-ODN and Ag uptake into the same cells, mice received footpad injections with fluorescently labeled adjuvants (as described above) plus rPA labeled with Alexa Fluor® 647. Popliteal lymph node cells were harvested 24 or 48 hours after injection for flow cytometry analysis. For each APC type examined, many cells incorporated only Ag or adjuvant; however, there was also a population of cells that acquired both rPA and D56-05 or D56-01. Mice immunized with D56-05 and rPA demonstrated the highest frequency of APCs with coincident Ag and adjuvant uptake as well as cells with adjuvant uptake only. Polychromatic imaging flow cytometry and subsequent calculation of BDS scoring in two additional experiments were employed to determine whether Alexa Fluor® 555-labeled D56-05 and Alexa Fluor® 647-labeled rPA specifically colocalized within the same cells. Approximately 11% of pDCs, 7% of mDCs, 5% of myeloid cells, and <1% of cDCs with joint D56-05 and rPA uptake demonstrated BDS scores greater than 2, indicating likely colocalization of Ag and adjuvant within cells at the time of measurement.

The impact of D56-05 on GC B and T follicular helper (TFH) cell responses within the injection site draining lymph nodes were evaluated. This was directly evaluated by flow cytometry, identifying GC B cells as B220+/GL7+/PNA+/CD95+ cells and $T_{FH}$ cells as CD4+/CXCR5+/PD1+ cells. Mice were immunized once in the footpad with rPA with/without D56-05 or D56-01 or vehicle control, with numbers of GC B or TFH cells monitored for 2 wk. Higher proportions of GC B and $T_{FH}$ cells were detected in draining lymph nodes of rPA/D56-05 immunized mice by day 5 and remained elevated at day 14. GC B and $T_{FH}$ responses were minimal in rPA only immunized mice compared with vehicle-injected mice. Taken together, these data suggest that the increased potency of D56-05 over D56-01 for induction of innate immunity is reflected in early GC B and T cell responses.

TABLE B5-1

Fold Induction of IFN Pathway-associated Genes Over Pre-immunization in Blood of Individual Monkeys in Response to Immunization with rPA ± D56-05 or D56-01

| Immunizations | GBP-1 | IFN-α | IL-6 | IRF-7 | ISG-54 | Mxb | p28 |
|---|---|---|---|---|---|---|---|
| rPA (10 μg) | 1.0 | 2.0 | 2.9 | 0.6 | 1.4 | 1.1 | 2.6 |
| rPA (10 μg) | 0.4 | 0.7 | 0.4 | 0.3 | 0.5 | 0.7 | 0.3 |
| rPA (10 μg) | 0.9 | 1.6 | 0.5 | 0.5 | 0.8 | 1.0 | 0.6 |
| 1000 μg D56-01 + rPA | 2.0 | 0.9 | 0.7 | 0.7 | 9.6 | 4.6 | 0.7 |
| 1000 μg D56-01 + rPA | 2.1 | 0.2 | 1.1 | 1.4 | 19.7 | 6.1 | 1.5 |
| 1000 μg D56-01 + rPA | 2.8 | 0.2 | 0.9 | 0.6 | 7.2 | 5.0 | 0.8 |
| 1000 μg D56-01 + rPA | 1.2 | 0.5 | 0.3 | 0.8 | 7.3 | 5.9 | 0.2 |
| 1000 μg D56-01 + rPA | 2.1 | 0.1 | 0.4 | 0.6 | 5.6 | 7.1 | 0.2 |
| 250 μg D56-01 + rPA | 0.6 | 2.9 | 1.1 | 0.5 | 1.3 | 1.2 | 0.4 |
| 250 μg D56-01 + rPA | 0.4 | 0.4 | 0.5 | 0.2 | 0.5 | 0.7 | 0.4 |
| 250 μg D56-01 + rPA | 2.6 | 0.2 | 1.0 | 0.9 | 14.2 | 9.5 | 0.4 |
| 250 μg D56-01 + rPA | 0.7 | 1.2 | 0.8 | 0.9 | 2.8 | 2.4 | 0.8 |
| 250 μg D56-01 + rPA | 0.9 | 0.8 | 1.0 | 0.8 | 2.5 | 1.8 | 0.9 |
| 250 μg D56-01 + rPA | 1.6 | 0.9 | 0.6 | 0.9 | 4.4 | 3.2 | 0.9 |
| 1000 μg D56-05 + rPA | 3.6 | 0.5 | 2.2 | 1.5 | 16.4 | 7.9 | 1.1 |
| 1000 μg D56-05 + rPA | 20.3 | 0.8 | 1.7 | 4.1 | 74.3 | 26.6 | 1.9 |
| 1000 μg D56-05 + rPA | 10.3 | 1.3 | 0.9 | 2.4 | 30.8 | 14.3 | 0.8 |
| 1000 μg D56-05 + rPA | 29.5 | 0.3 | 2.3 | 3.1 | 69.7 | 35.9 | 2.7 |
| 1000 μg D56-05 + rPA | 2.1 | 0.4 | 0.9 | 0.8 | 8.2 | 5.2 | 0.8 |
| 250 μg D56-05 + rPA | 14.7 | 3.6 | 2.7 | 4.3 | 61.8 | 19.9 | 1.3 |
| 250 μg D56-05 + rPA | 11.6 | 0.8 | 1.1 | 1.9 | 44.2 | 17.4 | 2.1 |
| 250 μg D56-05 + rPA | 2.6 | 0.3 | 2.0 | 1.2 | 10.5 | 5.1 | 0.9 |
| 250 μg D56-05 + rPA | 11.3 | 1.0 | 1.4 | 3.1 | 56.9 | 19.2 | 1.7 |
| 250 μg D56-05 + rPA | 9.5 | 1.1 | 2.8 | 4.5 | 45.2 | 18.9 | 4.0 |
| 250 μg D56-05 + rPA | 0.9 | 0.2 | 1.0 | 0.6 | 1.1 | 1.8 | 0.4 |
| 50 μg D56-05 + rPA | 7.0 | 0.7 | 2.5 | 2.6 | 20.3 | 10.1 | 2.5 |
| 50 μg D56-05 + rPA | 5.2 | 0.2 | 0.5 | 0.9 | 9.9 | 7.1 | 0.6 |
| 50 μg D56-05 + rPA | 0.9 | 0.4 | 0.6 | 0.7 | 4.9 | 4.5 | 1.0 |
| 50 μg D56-05 + rPA | 2.9 | 1.0 | 1.8 | 1.9 | 5.7 | 4.0 | 1.5 |
| 50 μg D56-05 + rPA | 6.0 | 1.0 | 2.8 | 5.5 | 41.4 | 14.3 | 4.5 |
| 50 μg D56-05 + rPA | 4.7 | 1.2 | 0.4 | 1.1 | 9.2 | 8.2 | 0.8 |

TABLE B5-2

Uptake of Fluorescently Labeled Compounds (Geometric Mean Fluorescence Intensity) in Draining Lymph Node Cells from Mice Administered D56-05 or D56-01

| Exp No. | D56-05 uptake (gMFI) | D56-01 uptake (gMFI) |
|---|---|---|
| pDC (MHCII+CD11b−CD11c+(B220+ or PDCA1+) Cells | | |
| 1 | 165 | 50 |
| 2 | 379 | 324 |
| cDC (MHCII+CD11b−CD11c+) Cells | | |
| 1 | 84 | 57 |
| 2 | 267 | 198 |
| mDC (MHCII+CD11b+CD11c+) Cells | | |
| 1 | 156 | 162 |
| 2 | 596 | 544 |

TABLE B5-3

Geometric Mean Fluorescence Intensity of CD69 and CD86 Expression on Draining Lymph Node pDCs from Mice Administered D56-05 or D56-01

| | | D56-05 | | | D56-01 | | |
|---|---|---|---|---|---|---|---|
| Exp No. | DPBS | 5 μg | 2 μg | 0.2 μg | 5 μg | 2 μg | 0.2 μg |
| CD69 Expression (gMFI) | | | | | | | |
| 1 | 369 | 4378 | 2494 | 553 | 1703 | 1409 | 710 |
| 2 | 20 | 1193 | 1408 | 160 | 431 | 287 | 161 |
| CD86 Expression (gMFI) | | | | | | | |
| 1 | 412 | 1299 | 1243 | 541 | 556 | 529 | 458 |
| 2 | 388 | 1536 | 958 | 562 | 717 | 910 | 579 |
| 3 | 70 | 711 | 519 | 105 | 105 | 105 | 90 |

Example B6: D56-05 Adjuvants Rapid, High Titer Toxin Neutralizing Antibody Responses to rPA and Protects Monkeys Against Lethal Challenge with Live *Bacillus* Anthrax Spores The ability of D56-05 to induce protective antigen-specific antibody responses in a mammalian subject (i.e., immunogenicity) was evaluated in monkeys immunized with D56-05+rPA. For comparison, additional groups of monkeys were immunized with D56-01+rPA or rPA alone. To test protection following one or two immunizations with D56-05, monkeys were challenged with a lethal dose of anthrax spores and monitored for survival.

In life procedures for the monkey immunogenicity study are described under Example B5. For the anthrax aerosol challenge study, monkeys (*Macaca fascicularis*) were housed at Battelle Biomedical Research Center (Columbus, Ohio) where all in life procedures were carried out. 25 male and 25 female healthy monkeys, previously not exposed to anthrax, were randomized by weight into groups of eight (4 male, 4 female) or six (3 male, 3 female). Animals were immunized by the i.m. route in the quadriceps on days 0 and/or 29 with 10 µg rPA in combination with either 1000 or 250 µg D56-05 in a total volume of 1 mL DPBS. A group comprised of six non-immunized animals was also included. Serum samples were collected during the study to confirm development of antibody responses. Monkeys were exposed to a target dose of 200×50% lethal dose ($LD_{50}$) equivalents of aerosolized *B. anthracis* Ames spores on day 69, 70 or 71. Monkeys were randomized to one of the three challenge days, with at least two monkeys from each group assigned to each day. The animals were monitored twice daily for survival and clinical signs of illness for 28 days following challenge. Any animal judged to be moribund was immediately euthanized. Qualitative bacteremia was assessed from day 62 onward by streaking 30-40 ml EDTA whole blood onto blood agar plates and incubating at 37° C. for at least 48 h. Samples resulting in any colonies consistent with *B. anthracis* morphology (g-hemolytic, white colonies, 4-10 mm in diameter with a rough appearance and irregular edges) were documented as positive.

Toxin Neutralization Assay (TNA). Development of antibody titers to rPA was assessed by the in vitro Toxin Neutralization Assay (TNA). The assay measures the ability of serum antibodies to rPA to specifically protect J774.1 cells against *Bacillus anthracis* lethal toxin cytotoxicity. J774.1 murine macrophages (American Type Culture Collection, Manassas, Va.) were exposed to PA and Lethal Factor (LF; List Biological Laboratories, Campbell, Calif.) in the presence or absence of serially diluted serum samples. Viability was assessed by addition of MTT (3-(4,5-dimethylthiazol-2-yl)-2,5-diphenyltetrazolium bromide). Titers were calculated as the reciprocal of the dilution of a serum sample that results in 50% neutralization of toxin-mediated cytotoxicity ($ED_{50}$), corresponding to the inflection point of a 4-parameter logistic log fit of the neutralization curve. TNA results are reported as the quotient of the $ED_{50}$ of the test sample and the $ED_{50}$ of a reference standard ($NF_{50}$). Assay end points were calculated using SoftMaxPro version 4.7.1 (Molecular Devices, Sunnyvale, Calif.). TNA assays were performed by Dynavax Technologies except on sera arising from days −1, +1, +3, +5, +7, +14, +21 and +28 relative to challenge which were performed at Battelle, with $NF_{50}$ values calculated using human reference standard AVR801. Assay end points were calculated using SAS (JMP, Cary, N.C.). Data acquisition and analysis were performed by a SpectraMax 190 or Versa-Max using SoftMaxPro version 5.0.1 (Molecular Devices, Sunnyvale, Calif.) or SAS (SAS Institute, Cary, N.C.). The lower limit of quantitation (LLOQ) was 100. Samples resulting in undetectable values were assigned a value equal to half the LLOQ.

Anti-rPA IgG quantification. Plates (96 well) were coated with rPA and incubated overnight. Standards and test sera, at appropriate dilution series, were assayed in duplicate. HRP-conjugated goat anti-human IgG (SouthernBiotech, Birmingham, Ala.) was used for detection and color was developed with a 3,3',5,5'-tetramethylbenzidine Microwell Peroxidase Substrate System (KPL, Gaithersburg, Md.). Titers were calculated as the reciprocal of the dilution (ED50), corresponding to the inflection point of a four-parameter logistic log fit curve. Results are reported as the quotient of the ED50 of the test sample and the ED50 of a reference standard (NF50). Data acquisition and analysis were performed by a SpectraMax 190 or VersaMax using SoftMaxPro v5.0.1 software (Molecular Devices).

Figure 15A:
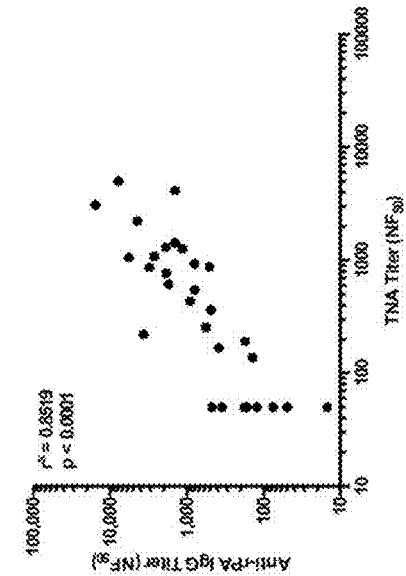
FIG. 15A-D illustrate that rPA/D56-05 vaccination leads to rapid induction of anti-rPA Ab response and long-lasting memory in monkeys. Cynomolgus macaques (n=3-6/group) were immunized i.m. (↓) with 10 mg rPA alone or in combination with 1000, 250, or 50 mg D56-05 or 1000 or 250 mg D56-01 on days 0 and 28. All monkeys received 25 mg rPA alone (↓) 23 wk following initial immunization. TNA and anti-rPA IgG titer levels were monitored for 25 wk following initial immunization.

Results. Table B6-1 and FIG. 15A show immunogenicity study data, specifically TNA titers induced in monkey serum 2 weeks following a single injection of rPA alone, rPA+D56-05, or rPA+D56-01 (individual titers, geometric mean and 95% confidence interval). The two highest doses of D56-05 induced mean TNA titers that were significantly higher than in animals given only rPA, compared with a nonsignificant increase by D56-01 addition. At the highest dose of D56-05, the calculated 31-fold increase in TNA titers compared with rPA alone is likely an underestimate of the adjuvant potency, as titers in rPA only animals were all below the level of detection for the TNA assay. Additionally, all animals (11 of 11) receiving 250-1000 mg D56-05 were seropositive whereas 5 of 11 animals immunized with 250-1000 mg D56-01 were below the LLOQ. These data indicate that both rPA+D56-05 and rPA+D56-01 induced rapid and potent titers of toxin neutralizing antibodies compared to immunization with rPA alone, but that TNA titers were highest in monkeys immunized with equivalent CC amounts of D56-05.

Figure 15C:
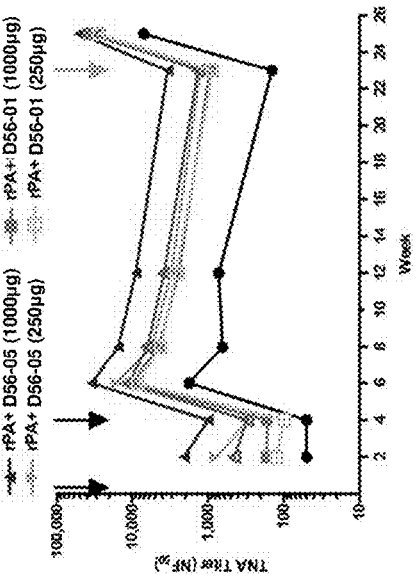
Figure 15B:
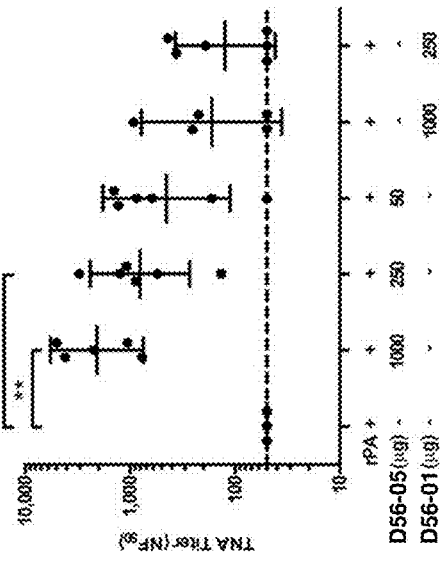
Figure 15D:
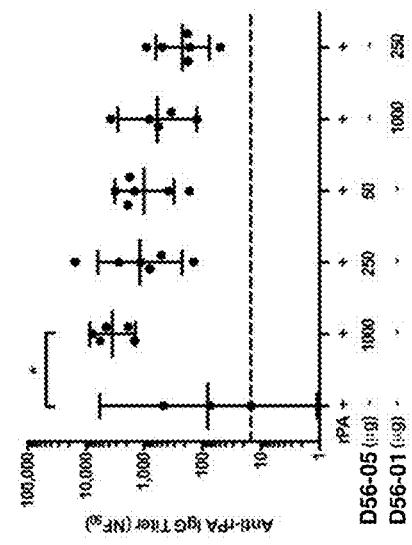

Likewise, titers of total anti-rPA IgG at 14 days were significantly increased following immunization with rPA/D56-05 (FIG. 15B) and were significantly correlated to the TNA results (FIG. 15C). Following the second immunization at day 28, a >15-fold boost in TNA responses was evident in all groups and the titers remained elevated for at least 18 wk. The memory response to antigenic challenge about 5 mo following a second immunization was also evaluated in these animals. Further increases in TNA titers of at least 15-fold (FIG. 15D) demonstrated a rapid, robust response, indicating potentially protective immunity.

Figure 16A:
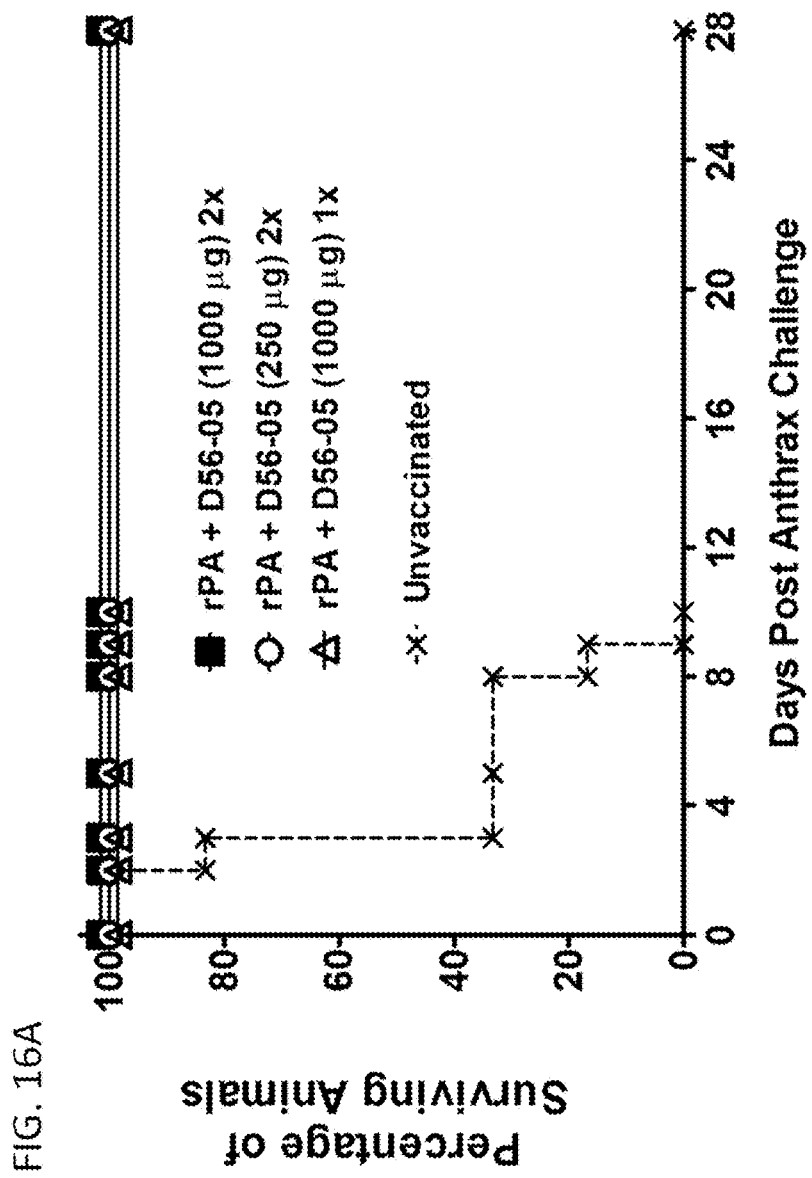

To directly evaluate protection, cynomolgus macaques were immunized i.m. with rPA plus D56-05 once (day 29) or twice (days 0 and 29) and challenged with a targeted dose of 200 LD50 equivalents of aerosolized *B. anthracis* spores on day 70±1. Survival, bacteremia, and symptoms of clinical disease were monitored for 28 days following challenge and serum samples collected before and after challenge for determination of TNA titers. FIG. 16A shows Kaplan-Meier survival analysis for monkeys challenged with aerosolized live anthrax spores following one or two immunizations with rPA+D56-05. Complete protection from anthrax challenge was achieved in all monkeys receiving a single vaccination of rPA with 1000 mg D56-05 or two vaccinations with either 250 or 1000 mg D56-05, whereas all unvaccinated animals succumbed to disease within 9 days of challenge. These data clearly indicate that a single immunization with rPA+D56-05 protects 100% of monkeys from lethal challenge. Animals immunized twice were also protected.

Furthermore, no animals vaccinated with rPA/D56-05 showed bacteremia or clinical symptoms at any time point after challenge. Following challenge, all animals produced a rapid increase in TNA titers, indicating a strong memory response. The memory response was striking in monkeys receiving a single rPA/D56-05 immunization, rising rapidly to levels comparable to twice-immunized animals within 7 days of the infectious challenge (FIG. 16B). Taken together, these data demonstrate that a single immunization of rPA plus 1000 mg D56-05 primes animals for a prominent recall response and provides protection against lethal challenge with aerosolized *B. anthracis* spores.

Although rapid, single-injection protection against anthrax exposure represents an unmet need, the potent adjuvant activity of D56-05 suggested that substantially reduced doses may be effective in situations where a two-injection prophylactic regimen is feasible. Therefore, in a separate experiment, TNA responses were monitored in monkeys immunized on days 0 and 28 with rPA and D56-05 at 1000, 50, 20, or 5 mg. TNA titers greater than 1000 were elicited in the two-immunization regimen, even with a D56-05 dose of 5 mg, the lowest dose tested, and were further boosted to greater than 10,000 by Ag only injection (used as a surrogate for bacterial spore exposure) (FIG. 16C). Thus, in the context of a two immunization regimen, the data suggest protective capacity with 1/200 of the D56-05 dose demonstrated to be protective in a single-immunization regimen in monkeys.

Figures 17A, 17B:
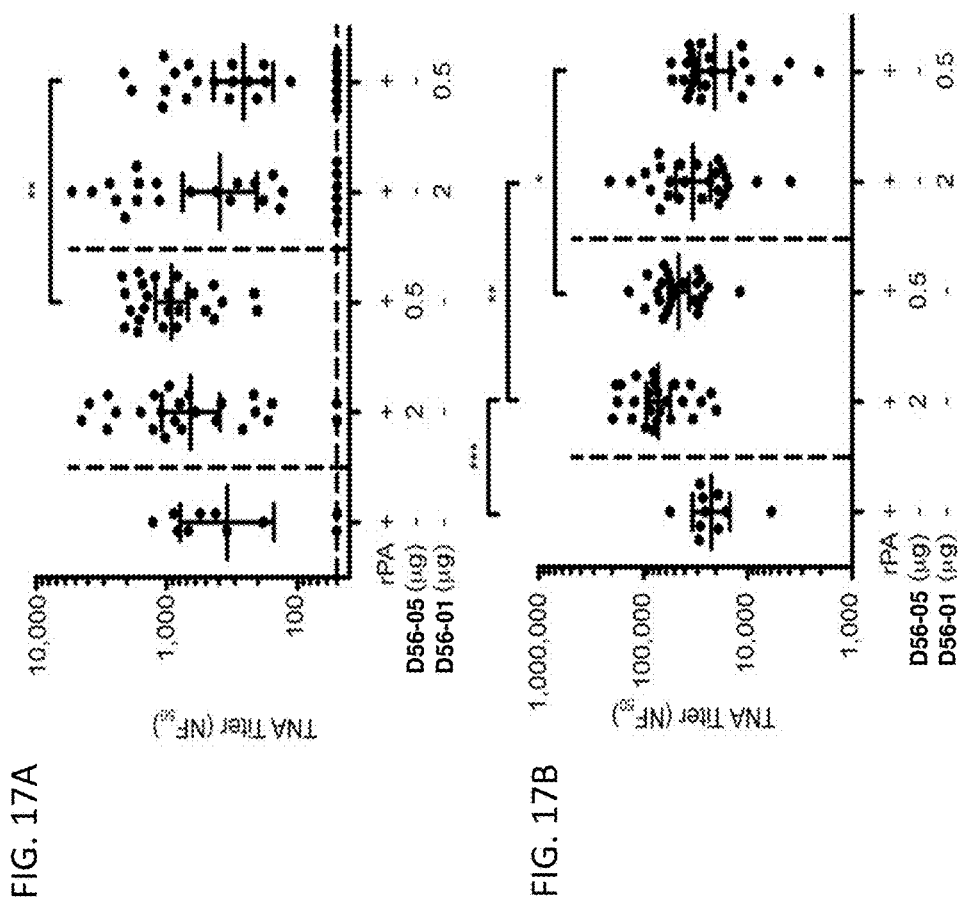
FIG. 17A-B illustrate that rPA/D56-05 immunization induces greater primary and secondary TNA titer responses in mice. Swiss Webster mice (n=25/group) were immunized with 5 mg rPA alone or in combination with 2 or 0.5 mg D56-05 or D56-01 on days 0 and 29. TNA titer levels were assessed (FIG. 17A) 4 wk after the first immunization and (FIG. 17B) 2 wk after the second immunization. Data are shown as means with 95% CI. *$p<0.05$, $p<0.01$, *$p<0.001$ by Kruskal-Wallis with a Dunn posttest.

Improved adjuvant activity by the D56-05 nanoparticle formulation was also evaluated in mice. Indeed, rPA/D56-05 induced significantly higher TNA titers after both a first and second immunization in mice, demonstrating the relevance of the species for studies investigating the D56-05 mechanism of action (FIGS. 17A-B).

TABLE B6-1

TNA Titers in Monkey Serum 2 Weeks Post First Immunization with rPA + D56-05, rPA + D56-01, or rPA

| | rPA (10 μg) | rPA/D56-05 (1000 μg) | rPA/D56-05 (250 μg) | rPA/D56-05 (50 μg) | rPA/D56-01 (1000 μg) | rPA/D56-01 (250 μg) |
|---|---|---|---|---|---|---|
| | 50 | 5021 | 1270 | 1431 | 50 | 50 |
| | 50 | 4163 | 1089 | 618 | 50 | 50 |
| | 50 | 772 | 137 | 168 | 223 | 365 |
| | | 2223 | 881 | 1304 | 256 | 50 |
| | | 1067 | 546 | 872 | 934 | 435 |
| | | | 3081 | 50 | | 192 |
| GeoMean | 50 | 2073 | 809 | 451 | 168 | 125 |
| 95% CI | (50-50) | (5739-749) | (2407-272) | (1817-112) | (782-36) | (372-42) |

Example B7: At Equivalent Doses, the Nanoparticle Formulation D56-05 Demonstrates a Safety Advantage in Mice Compared to Free Linear Chimeric Compound D56-01

To test the effect of nanoparticle formulation on the safety/tolerability of CC sequences in vivo, mice were administered repeated high dose injections of D56-05 and D56-01 by the intramuscular route. As a species in which to assess toxicity, mice demonstrate an exaggerated pharmacological response to CpG ODN-containing nucleotides, compared to primates, due to more widespread cellular distribution of TLR9 expression in the mouse. We measured serum cytokine responses and monitored changes in body weight in mice receiving 100 μg (based on D56-01 weight) of either D56-05 or D56-01 every 2 weeks for a total of 4 injections in order to assess relative safety of the free and nanoparticle versions of the CC.

Female BALB/c mice (6-10 weeks of age) were purchased from Charles River and housed at Murigenics (Vallejo, Calif.) where all in life procedures were carried out. Groups of 5 mice were administered 100 μg D56-05 or D56-01 once, twice, three, or four times with 2 weeks between injections. Select groups were sacrificed 2 hours after each injection. For controls, one group received no injections and another group was administered injection vehicle (Saline, 50 μL). Both these groups were sacrificed 18 hours after the fourth injection. Serum was harvested by cardiac puncture at time of sacrifice. Spleen, liver and kidneys were harvested at sacrifice and weighed. Mice were weighed twice weekly throughout the study.

ELISA. Cytokine levels in serum samples were measured using commercially available antibody pairs as described under Example B1. Antibody pairs for detection of mouse IL-6 and IL-12p40 were sourced from BD Biosciences (San Jose, Calif.). Reagents for detection of mouse IP-10, MCP-1, and TNF-α were sourced from R&D Systems (Minneapolis, Minn.). The limits of detection for these assays ranged from about 20 pg/mL to about 150 pg/mL. Data acquisition and analysis were performed by a SpectraMax 190 or VersaMax using SoftMaxPro v5.0.1 software (Molecular Devices).

D56-05 or D56-01 tissue quantification by enzyme-linked hybridization assay or hybridization assay. Spleen, liver, kidney, or injection site muscle, 25-50 mg per tissue per individual animal, and draining lymph nodes, pooled per individual animal, were homogenized in 20 mM Tris (pH 8), 20 mM EDTA (Sigma-Aldrich, St. Louis, Mo.), 100 mM sodium chloride, 0.2% SDS (Teknova, Hollister, Calif.) using the TissueLyser II (Qiagen), and subject to proteinase K (New England BioLabs, Ipswitch, Mass.) digestion at 1.2 U/mg tissue for 6-20 hours at 50° C. Nunc Immobilizer amino plates were coated overnight at 4° C. with 30 ng/ml capture probe (5'-GCGCCGAGAA CGTTGCGCCG A-3' set forth as SEQ ID NO: 18 for D56-01 quantification; and 5'-AGCCGCGTTG CAAGAGAAGC GATGCGCGGC TCG-3' set forth as SEQ ID NO:19 for D56-05 quantification) in 0.1 M sodium phosphate (Teknova). For quantification of D56-05, homogenized samples, mixed in equal volume with 0.6 mg/ml detection probe (5'-GCGCCGA-GAA CGTTGCGCCG A-3' set forth as SEQ ID NO:18), were incubated for 75 min at 52° C. For quantification of D56-01, homogenized samples, mixed in equal volume with SSC plus 2% N-lauroylsarcosine sodium salt buffer, were incubated for 2 hours at 45° C. and allowed to cool for 30 min at room temperature. Synthesis of complementary 39 ends of captured D56-01 was catalyzed by 1.25 U Klenow fragment (New England BioLabs) in the presence of 0.5 mM biotinylated dUTP and 50 mM dNTP (New England BioLabs). HRP-conjugated streptavidin (Thermo Scientific, Waltham, Mass.) was used for adjuvant detection, and color was developed with a 3,3',5,5'-tetramethylbenzidine microwell peroxidase substrate system (KPL). Adjuvants served as standards. The LLOQs were 6.24 and 7.62 ng/g tissue for D56-05 and D56-01, respectively. All data acquisition and analysis were performed by a SpectraMax 190 or VersaMax using SoftMaxPro v5.0.1 software (Molecular Devices).

Results. To test whether D56-05 and monomeric D56-01 displayed differential tissue distribution kinetics following i.m. injection, mice were injected with D56-05 or D56-01 and levels of the adjuvants at the injection site and draining lymph nodes as well as at distal sites (spleen, liver, and kidney) were measured. Mice received a high dose (100 μg) of either adjuvant to facilitate recovery, and tissues were harvested 1 day after injection. D56-05 and D56-01 were quantified by hybridization assays as described above. D56-

Figure 18:
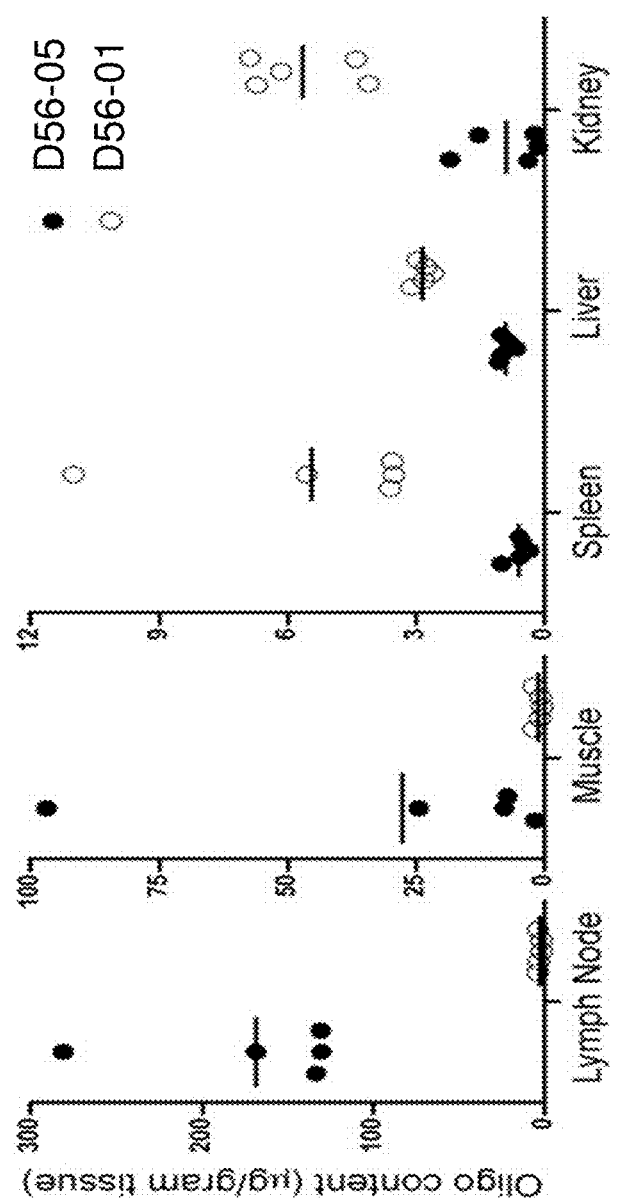
FIG. 18 shows that D56-05 nanoparticles are retained at the injection site and draining lymph nodes. BALB/c mice (n=5) were injected i.m. with 100 mg D56-05 or D56-01. Oligonucleotide content (micrograms per gram of tissue) in injection site muscle, draining lymph nodes (popliteal, inguinal, sciatic, lumbar, and sacral), spleen, liver, and kidney was assessed at 1 d postinjection. Data are shown with means and are representative of two independent experiments.

05 was concentrated in injection site muscle and lymph nodes (popliteal, inguinal, sciatic, lumbar, and sacral), whereas D56-01 quickly distributed systemically (FIG. 18). D56-01 was detected at minimal levels at the injection site and lymph nodes, and instead concentrated in the spleen, liver, and kidney. These data indicate that nanoparticle and monomeric D56-01 differentially distribute within 24 hours of injection, suggesting that preferential local retention of D56-05 may contribute to its increased potency as an adjuvant.

All of the systemic toxicities commonly observed in mice following CpG-ODN administration were greatly reduced in animals injected with D56-05 compared with D56-01. Table B7-1 shows serum cytokine levels in mice 2 hours after administration of the first dose of either D56-05 or D56-01. The inflammatory cytokines IL-6, IL-12p40, IP-10, MCP-1 and TNF-α were all induced at high levels in the blood 2 hours after D56-01 injection but not in response to D56-05.

Additionally, there was little evidence of a delayed systemic effect in D56-05-injected mice. Mice sacrificed after four biweekly injections of D56-05 demonstrated spleen and liver weights similar to sham-injected mice. Mice administered D56-01, but not D56-05, developed splenomegaly and hepatomegaly evident after 2 injections, which became more pronounced after 3 and 4 injections. This data is summarized in Table B7-2. There was no effect on kidney weight. Histopathological changes in D56-05-injected mice were minimal, whereas repeated D56-01 injections resulted in increased splenic extramedullary hematopoietic activity and hepatic changes, including cellular infiltration of sinusoids, hepatocellular alterations, and mild/moderate liver necrosis.

Figure 19:
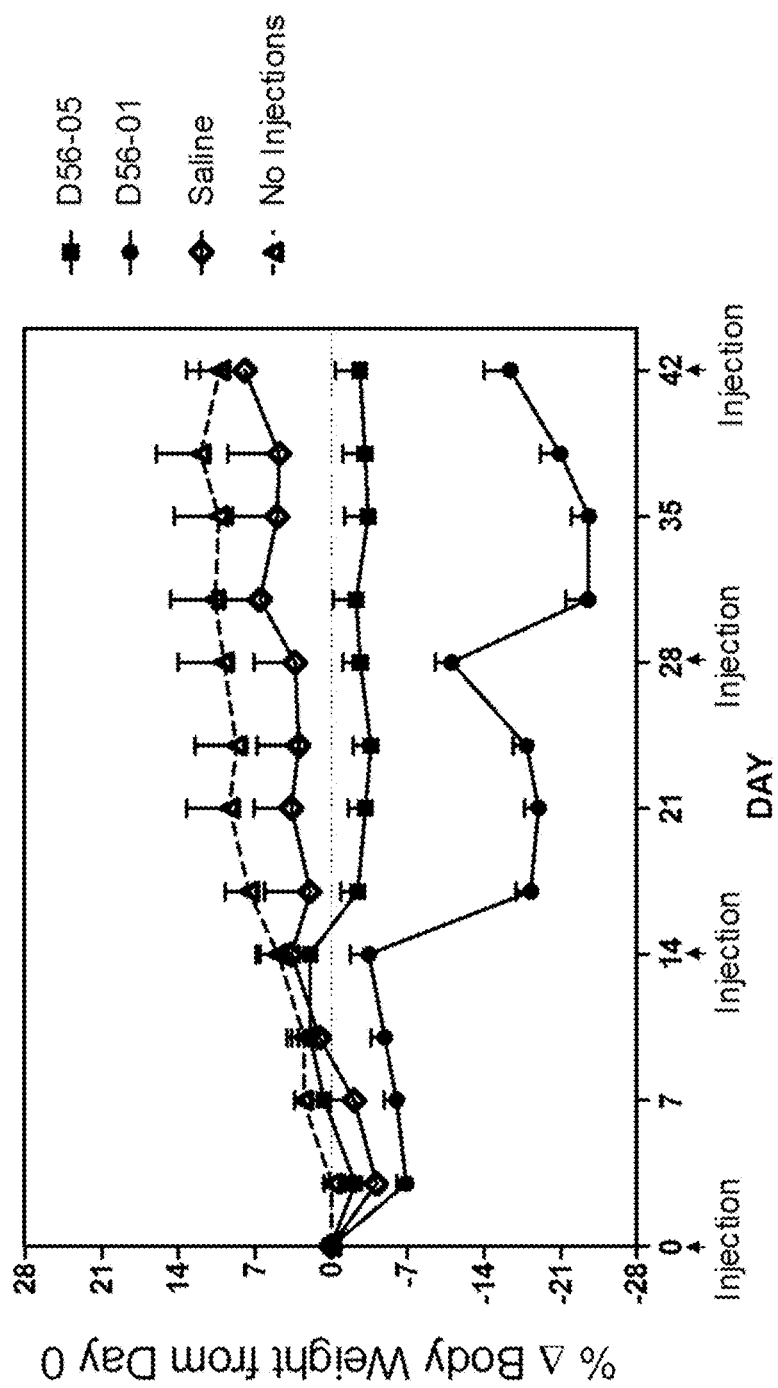
FIG. 19 provides a plot showing the body weight over time of mice administered 1-4 doses (100 μg) of DV56-05 or DV56-01.

FIG. 19 shows group-averaged body weights over the study for mice receiving D56-05 and D56-01. Marked body weight loss, a TNF-alpha-dependent, CpG-induced toxicological event specific to rodents, occurred in animals administered biweekly D56-01 injections. In contrast, body weights were only slightly lower than those of controls for mice administered biweekly injections of high-dose D56-05. This data has been adjusted to remove the effect the additional weight due to splenomegaly and hepatomegaly in mice administered D56-01 and demonstrates that overall body weight decreases with successive administrations of high dose D56-01 but not D56-05. Together, these data show a marked safety advantage of nanoparticle-formulated D56-05 over free CC D56-01. Unlike the free CC, the nanoparticle formulation does not induce inflammatory serum cytokine responses, appreciable organomegaly or dramatic reduction in body weight, even after repeated high-dose injections. Thus, the improved adjuvant activity of D56-05 nanoparticles over monomeric D56-01 is accompanied by reduced systemic toxicity signals.

TABLE B7-1

Serum Cytokine Levels in Mice 2 h After a Single Dose of 100 μg D56-05 or D56-01

| Cytokine (pg/mL) | D56-05 Mean | D56-05 SEM | D56-01 Mean | D56-01 SEM |
|---|---|---|---|---|
| IL-6 | 20 | 0 | 491 | 62 |
| IL-12p40 | 1043 | 129 | 33273 | 3671 |
| IP-10 | 78 | 0 | 1179 | 160 |
| MCP-1 | 33 | 4 | 3871 | 327 |
| TNF-α | 33 | 6 | 965 | 91 |

TABLE B7-2

Organ Tissue Weights in Mice Administered 1-4 Doses of 100 μg D56-05 or D56-01

| # of Injections | Liver in grams (Mean ± SEM) D56-05 | D56-01 | Saline | None | Spleen in grams (Mean ± SEM) D56-05 | D56-01 | Saline | None |
|---|---|---|---|---|---|---|---|---|
| 1 | 0.8 ± 0.03 | 0.9 ± 0.02 | — | — | 0.1 ± 0.01 | 0.1 ± 0.01 | — | — |
| 2 | 1.0 ± 0.04 | 1.8 ± 0.1 | — | — | 0.2 ± 0.01 | 0.5 ± 0.03 | — | — |
| 3 | 0.9 ± 0.03 | 2.8 ± 0.2 | — | — | 0.2 ± 0.01 | 0.8 ± 0.06 | — | — |
| 4 | 1.0 ± 0.03 | 3.2 ± 0.08 | 0.8 ± 0.03 | 0.8 ± 0.02 | 0.3 ± 0.02 | 1.0 ± 0.07 | 0.07 ± 0.01 | 0.08 ± 0.01 |

Example B8: Intra-Tumoral Administration of D56-05 Suppresses Tumor Growth in Mice with Lymphoma Cell Line EG7-OVA Tumors To test the application of D56-05 in a model of cancer immunotherapy (Moore et al., Cell, 54:777, 1998), the lymphoma cell line EG7 1 OVA was used to assess the effect of intratumoral injection of D56-05 or a control non-CpG-containing oligonucleotide (D56-30) on growth of established tumors.

Female C57BL/6 mice (6-10 weeks of age) were purchased from Harlan and housed at Murigenics (Vallejo, Calif.) where all in life procedures were carried out. 1×10*6 EG-7 cells (American Type Culture Collection, Manassas, Va.) were injected subcutaneously into the flank of C57BL/6 mice. Starting on study day 0 (4 days after cell implantation) mice (N=5/group) were administered injections into the established tumor mass of 50 μg D56-05 or a control non-CpG oligonucleotide (D56-30) in a volume of 150 μL of PBS. Injections were administered daily on Days 0, 3, and 7. Animals were observed and tumor size (volume) was measured.

Figure 20:
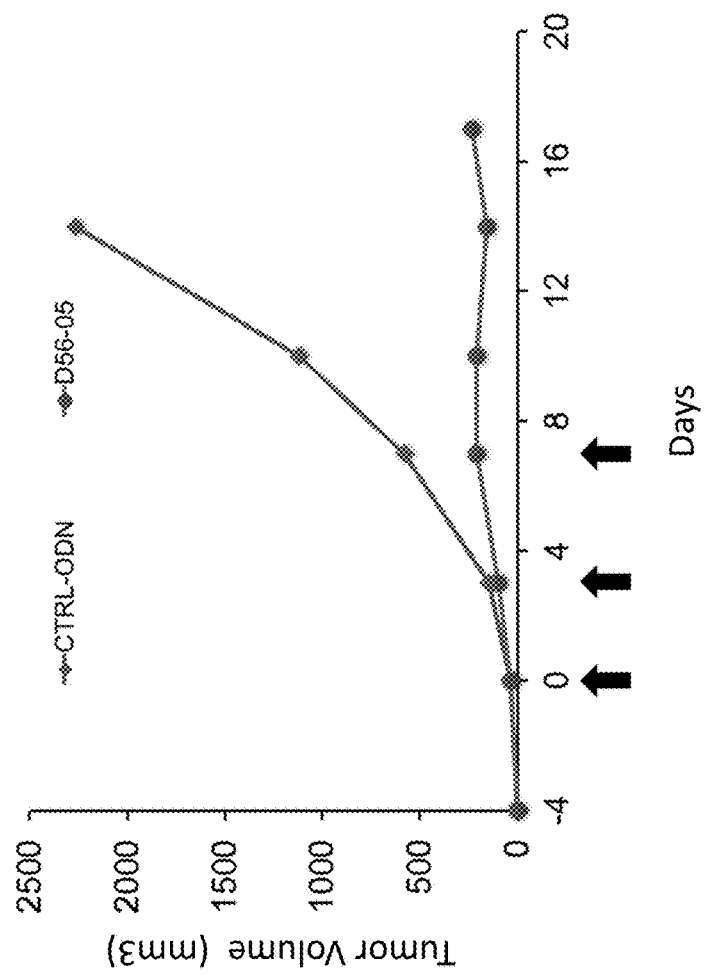
FIG. 20 provides a plot showing the tumor size of mice receiving D56-05 or D56-30. In brief, about one million E.G-7 OVA cells (ATCC catalog number CRL-2113) were injected subcutaneously into the flank of C57BL/6 mice. Starting on study day 0 (4 days after cell implantation) mice were injected intratumorally (i.e., into the established tumor mass) with (50 microgram (mcg) of D56-05 or a control non-CpG oligonucleotide (D56-30) in a volume of 150 µL PBS. Injections were administered on Days 0, 3 and 7. Mice were observed and tumor size (volume) was measured as indicated. E.G7-OVA is a transgenic cell line, derived from the C57BL/6 (H-2 b) mouse lymphoma cell line EL4, which constitutively secretes chicken ovalbumin.

Tumor volume data is shown in FIG. 20. The data demonstrate that D56-05 administered by the intratumoral route inhibited tumor volume increase in this murine tumor model.

Example B9: In Vitro Potency Evaluation of D56-05 (Aka [(D56-01)-PEG$_6$]$_x$-FICOLL) Conjugates with Different D56-01:FICOLL Molar Ratios (x)

The effect of varying the D56-01:FICOLL molar ratio (x) in D56-05 (aka [(D56-01)-PEG$_6$]$_x$-FICOLL) conjugates on the potency of the biological response was assessed by means of an in vitro analysis. The in vitro potency in human B cells was determined as described in Example B1 for D56-05 conjugates with different D56-01:FICOLL molar ratios (x): D56-05 x=24, D56-05 x=53, D56-05 x=82, D56-05 x=124 and D56-05 x=154. Results for the human B cell IL-6 assay are shown in Table B9-1. Refer to Example S12 for the synthesis of D56-05 with different D56-01:FICOLL molar ratios (x).

These data indicate that D56-05 conjugates with higher D56-01: FICOLL molar ratios (x) showed similar potency in the human IL-6 assay as compared to D56-05.

TABLE B9-1

Induction of IL-6 from Human B Cells by D56-05 (aka [(D56-01)-PEG$_6$]$_x$-FICOLL) Conjugates Produced with Various D56-01:FICOLL Molar Ratios (x) as EC50 (mM)

| Donor # | D56-01 | D56-05 x = 140 | D56-05 x = 24 | D56-05 x = 53 | D56-05 x = 82 | D56-05 x = 124 | D56-05 x = 154 |
|---|---|---|---|---|---|---|---|
| Do 1 | 0.056 | 0.021 | 0.025 | 0.020 | 0.020 | 0.025 | 0.007 |
| Do 2 | 0.067 | 0.016 | 0.020 | 0.020 | 0.015 | 0.020 | 0.016 |
| Do 3 | 0.063 | 0.025 | 0.039 | 0.029 | 0.021 | 0.018 | 0.020 |
| Do 4 | 0.063 | ND | 0.030 | 0.016 | 0.016 | 0.019 | 0.035 |
| Do 5 | 0.056 | ND | 0.032 | 0.029 | 0.013 | 0.023 | 0.019 |
| Ave | 0.061 | 0.021 | 0.029 | 0.023 | 0.017 | 0.021 | 0.019 |
| SD | 0.005 | 0.004 | 0.008 | 0.006 | 0.003 | 0.003 | 0.010 |
| Count | 5 | 3 | 5 | 5 | 5 | 5 | 5 |
| SEM | 0.002 | 0.003 | 0.003 | 0.003 | 0.002 | 0.001 | 0.004 |
| Mean | 0.061 | 0.020 | 0.028 | 0.022 | 0.017 | 0.021 | 0.017 |

ND = not determined;
D56-05 with x = 140 is Pilot Lot 2 and was used as a positive control in this experiment

Example B10: In Vitro Potency Evaluation of D56-05, D56-25, D56-26 and D56-27 (Aka [(D56-01)-PEG$_n$]$_x$-FICOLL) Manufactured Using SM-PEG$_n$ with n=6, 24, 45, and 70

The effect of varying the length (n) of the SM-PEG$_n$ linker molecule in [(D56-01)-PEG$_n$]$_x$-FICOLL was tested by measuring potency of the in vitro biological response. The in vitro potency in human pDC-enriched PBMC and B cells was determined as described in Example B1 for [(D56-01)-PEG$_n$]$_x$-FICOLL conjugates, D56-05, D56-25, D56-26 and D56-27, manufactured using SM-PEG$_n$ with n=6, 24, 45 and 70, respectively, as described in Example S3 and Example S13. Results for the human pDC-enriched PBMC IFN-α assay and the human B cell IL-6 assay are shown in Table B10-1 and Table B10-2, respectively. [(D56-01)-PEG$_n$]$_x$-FICOLL conjugates with longer PEG linkers showed slightly increased potency in the IFN-α assay and slightly reduced potency in the IL-6 assay.

TABLE B10-1

Induction of IFN-α from Human pDC-enriched PBMC by [(D56-01)-PEG$_n$]$_x$-FICOLL Conjugates Produced with Different SM-PEG$_n$ Linkers as EC50 (mM)

| Donor # | (D56-01)-PEG$_6$-FICOLL[a] | (D56-01)-PEG$_6$-FICOLL | (D56-01)-PEG$_{24}$-FICOLL | (D56-01)-PEG$_{45}$-FICOLL | (D56-01)-PEG$_{70}$-FICOLL |
|---|---|---|---|---|---|
| Do 1 | 0.010 | 0.009 | 0.005 | 0.004 | 0.004 |
| Do 2 | 0.012 | 0.013 | 0.007 | 0.006 | 0.005 |
| Do 3 | 0.007 | 0.006 | 0.004 | 0.003 | 0.004 |
| Do 4 | 0.004 | 0.004 | 0.003 | 0.002 | 0.003 |
| Do 5 | 0.004 | 0.005 | 0.004 | 0.003 | 0.004 |
| Do 6 | 0.007 | 0.010 | 0.004 | 0.006 | 0.005 |
| Ave | 0.008 | 0.008 | 0.004 | 0.004 | 0.004 |
| SD | 0.003 | 0.003 | 0.001 | 0.001 | 0.001 |
| Count | 6 | 6 | 6 | 6 | 6 |
| SEM | 0.001 | 0.001 | 0.001 | 0.001 | 0.000 |
| Mean | 0.007 | 0.007 | 0.004 | 0.004 | 0.004 |

[a]Pilot lot 4.

TABLE B10-2

Induction of IL-6 from Human B Cells by [(D56-01)-PEG$_n$]$_x$-FICOLL Conjugates Produced with Various SM-PEG(n) Linkers as EC50 (mM)

| Donor # | (D56-01)-PEG$_6$-FICOLL[a] | (D56-01)-PEG$_6$-FICOLL | (D56-01)-PEG$_{24}$-FICOLL | (D56-01)-PEG$_{45}$-FICOLL | (D56-01)-PEG$_{70}$-FICOLL |
|---|---|---|---|---|---|
| Do 7 | 0.019 | 0.003 | 0.004 | 0.007 | 0.007 |
| Do 8 | 0.016 | 0.004 | 0.008 | 0.008 | 0.006 |
| Do 9 | 0.013 | 0.002 | 0.003 | 0.003 | 0.009 |
| Do 10 | 0.014 | 0.002 | 0.002 | 0.005 | 0.011 |
| Do 11 | 0.016 | 0.003 | 0.005 | 0.006 | 0.007 |
| Ave | 0.016 | 0.003 | 0.005 | 0.006 | 0.008 |
| SD | 0.002 | 0.001 | 0.002 | 0.002 | 0.002 |
| Count | 5 | 5 | 5 | 5 | 5 |
| SEM | 0.001 | 0.000 | 0.001 | 0.001 | 0.001 |
| Mean | 0.016 | 0.003 | 0.004 | 0.005 | 0.008 |

[a]Pilot lot 4.

We claim:

1. A linear chimeric compound comprising:
three nucleic acid moieties and two hexaethylene glycol (HEG) spacers as 5'-TCGGCGC-3'-HEG-5'-AACGTTC-3'-HEG-5'-TCGGCGC-3' (SEQ ID NO:2), wherein the linear chimeric compound contains fewer than 50 nucleotides, and wherein one or more linkages between the nucleotides and between the nucleotides and the HEG spacers are phosphorothioate ester linkages.

2. The linear chimeric compound of claim 1, wherein the linear chimeric compound consists of 5'-TCGGCGC-3'-HEG-5'-AACGTTC-3'-HEG-5'-TCGGCGC-3' (SEQ ID NO:2).

3. The linear chimeric compound of claim 1, wherein the nucleic acid moieties are 2'-deoxyribopolynucleotides.

4. The linear chimeric compound of claim 1, wherein all of the linkages are phosphorothioate ester linkages.

5. A pharmaceutical composition comprising (i) a pharmaceutically acceptable excipient, and (ii) the linear chimeric compound of claim 1.

6. The pharmaceutical composition of claim 5, wherein the linear chimeric compound is capable of stimulating cytokine production by mammalian leukocytes, comprising one or more of the group consisting of:
stimulating production of IFN-alpha by human peripheral blood mononuclear cells;
stimulating production of IL-6 by human B lymphocytes; and
stimulating production of one or both of IL-12p40 and IL-6 by mouse splenocytes.

7. The pharmaceutical composition of claim 5, wherein the linear chimeric compound is capable of stimulating proliferation of mammalian B lymphocytes.

8. The pharmaceutical composition of claim 5, wherein the composition is a sterile solution.

9. The pharmaceutical composition of claim 5, wherein the composition further comprises an antigen that is not covalently-linked to the linear chimeric compound.

10. The pharmaceutical composition of claim 9, wherein the antigen is a microbial antigen, an allergen or a tumor antigen.

11. The pharmaceutical composition of claim 5, wherein the composition is essentially endotoxin-free.

12. A method of stimulating an immune response in a mammalian subject, comprising administering to a mammalian subject a pharmaceutical composition of claim 5 in an amount sufficient to stimulate an immune response in the mammalian subject.

13. The method of claim 12, wherein stimulating an immune response comprises one or more of the group consisting of:
stimulating IFN-alpha production;
stimulating IL-6 production;
stimulating B lymphocyte proliferation;
stimulating interferon pathway-associated gene expression;
stimulating chemoattractant-associated gene expression; and
stimulating plasmacytoid dendritic cell (pDC) maturation.

14. The method of claim 12, wherein when the pharmaceutical composition further comprises an antigen, stimulating an immune response comprises inducing an antigen-specific antibody response, wherein titer of the antigen-specific antibody response is higher when the antigen is administered in combination with the linear chimeric compound than when the antigen is administered without the linear chimeric compound.

15. A method of inducing an antigen-specific antibody response in a mammalian subject, comprising administering to a mammalian subject the pharmaceutical composition of claim 9 in an amount sufficient to induce an antigen-specific antibody response in the mammalian subject.

16. The method of claim 15, wherein the mammalian subject is a human.

17. The linear chimeric compound of claim 1, wherein the linear chimeric compound contains fewer than 30 nucleotides.

18. The pharmaceutical composition of claim 10, wherein the microbial antigen is a viral antigen.

* * * * *

SEQUENCE LISTING

<160> NUMBER OF SEQ ID NOS: 19

<210> SEQ ID NO 1
<211> LENGTH: 21
<212> TYPE: DNA
<213> ORGANISM: Artificial Sequence
<220> FEATURE:

```
<223> OTHER INFORMATION: Synthetic Construct

<400> SEQUENCE: 1
tcggcgcaac gttctcggcg c                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 2
tcggcgcaac gttctcggcg c                                              21

<210> SEQ ID NO 3
<211> LENGTH: 14
<212> TYPE: DNA
<213> ORGANISM: Artificial Sequence
<220> FEATURE:
<223> OTHER INFORMATION: Synthetic Construct

<400> SEQUENCE: 3
tcggcgcaac gttc                                                      14

<210> SEQ ID NO 4
<211> LENGTH: 14
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety

<400> SEQUENCE: 4
tcggcgcaac gttc                                                      14

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct

<400> SEQUENCE: 5
tgactgtgaa ccttagagat ga                                             22

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
tgactgtgaa cgttcgagat ga                                             22
```

```
<210> SEQ ID NO 7
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 7
tcgtcgaacg ttcgagatga t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 8
tcgacgttcg acgtaacgtt c                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 9
tcgttcgtcg ttcgaacgtt c                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 10
tcgttcgaac gttctcgttc g                                              21
```

```
<210> SEQ ID NO 11
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 11
tcggcgctcg gcgcaacgtt c                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 12
tcgccggtcg ccggaacgtt c                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 13
tcgccggaac gttctcgccg g                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 14
tcgatcgtcg atcgaacgtt c                                              21
```

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 15
tcgtcgttcg tcgtaacgtt c                                          21

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 16
tcgtcgtaac gttctcgtcg t                                          21

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (7)...(8)
<223> OTHER INFORMATION: positions 7 and 8 are linked by a
      hexa-(ethylene glycol) moiety
<221> NAME/KEY: misc_feature
<222> LOCATION: (14)...(15)
<223> OTHER INFORMATION: positions 14 and 15 are linked by a
      hexa-(ethylene glycol) moiety

<400> SEQUENCE: 17
tcgacgtaac gttctcgacg t                                          21

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
gcgccgagaa cgttgcgccg a                                          21

<210> SEQ ID NO 19
<211> LENGTH: 33
<212> TYPE: DNA
<213> ORGANISM: Artificial Sequence
<220> FEATURE:

```
<223> OTHER INFORMATION: Synthetic Construct

<400> SEQUENCE: 19
agccgcgttg caagagaagc gatgcgcggc tcg                                    33
```